(12) United States Patent
Cheon et al.

(10) Patent No.: US 7,741,323 B2
(45) Date of Patent: Jun. 22, 2010

(54) INDENE DERIVATIVES AND PROCESS FOR THE PREPARATION THEREOF

(75) Inventors: Hyae Gyeong Cheon, Daejeon (KR); Sung-Eun Yoo, Kongju-si (KR); Sung Soo Kim, Daejeon (KR); Sung-Don Yang, Daejeon (KR); Kwang-Rok Kim, Daejeon (KR); Sang Dal Rhee, Daejeon (KR); Jin Hee Ahn, Daejeon (KR); Seung Kyu Kang, Daejeon (KR); Won Hoon Jung, Daejeon (KR); Sung Dae Park, Seoul (KR); Nam Gee Kim, Seoul (KR); Jang Hyuk Lee, Yongin-si (KR); Sun Chul Huh, Koyang-si (KR); Jae Mok Lee, Seoul (KR); Seog Beom Song, Suwon-si (KR); Soon Ji Kwon, Yongin-si (KR); Jong Hoon Kim, Anyang-si (KR); Jeong-Hyung Lee, Daejeon (KR); Seung Jun Kim, Daejeon (KR)

(73) Assignees: Korea Research Institute of Chemical Technology (KR); Jeil Pharm. Co., Ltd. (KR); Korea Research Institute of Bioscience and Biotechnology (KR); CJ Corp. (KR)

( * ) Notice: Subject to any disclaimer, the term of this patent is extended or adjusted under 35 U.S.C. 154(b) by 799 days.

(21) Appl. No.: 10/599,911

(22) PCT Filed: Apr. 13, 2005

(86) PCT No.: PCT/KR2005/001066

§ 371 (c)(1),
(2), (4) Date: Oct. 23, 2006

(87) PCT Pub. No.: WO2005/100303

PCT Pub. Date: Oct. 27, 2005

(65) Prior Publication Data

US 2007/0185109 A1  Aug. 9, 2007

(30) Foreign Application Priority Data

Apr. 13, 2004  (KR) .................. 10-2004-0025217

(51) Int. Cl.
| | | |
|---|---|---|
| C07C 255/47 | (2006.01) |
| C07C 251/32 | (2006.01) |
| C07C 237/24 | (2006.01) |
| C07C 69/74  | (2006.01) |
| C07D 413/12 | (2006.01) |
| C07D 333/28 | (2006.01) |
| C07D 333/22 | (2006.01) |
| C07D 333/24 | (2006.01) |
| C07D 333/60 | (2006.01) |
| C07D 317/60 | (2006.01) |
| C07D 317/70 | (2006.01) |
| C07D 307/54 | (2006.01) |
| C07D 277/30 | (2006.01) |
| C07D 265/30 | (2006.01) |
| C07D 295/135 | (2006.01) |
| C07D 233/64 | (2006.01) |
| C07D 213/53 | (2006.01) |
| C07D 213/64 | (2006.01) |
| A61K 31/5377 | (2006.01) |
| A61K 31/495 | (2006.01) |
| A61K 31/4402 | (2006.01) |
| A61K 31/44 | (2006.01) |
| A61K 31/426 | (2006.01) |
| A61K 31/4164 | (2006.01) |
| A61K 31/381 | (2006.01) |
| A61K 31/36 | (2006.01) |
| A61K 31/277 | (2006.01) |
| A61K 31/216 | (2006.01) |
| A61K 31/165 | (2006.01) |

(52) U.S. Cl. .................... 514/238.2; 564/300; 564/301; 544/177; 544/399; 544/165; 544/159; 549/496; 549/433; 549/65; 549/77; 549/442; 549/58; 548/204; 548/336.1; 546/337; 546/338; 546/335; 546/300; 558/426; 514/510; 514/619; 514/640; 514/644; 514/471; 514/365; 514/463; 514/357; 514/438; 514/466; 514/231.5; 514/443; 514/400; 514/351

(58) Field of Classification Search ................ 564/300, 564/301

See application file for complete search history.

(56) References Cited

U.S. PATENT DOCUMENTS

2007/0225288 A1* 9/2007 Cheon et al. ............ 514/239.2

OTHER PUBLICATIONS

Golub et al., Science, vol. 286, Oct. 15, 1999, pp. 531-537.*
Shearer and Billin, Biochimica et Biophysica Acta 2007, 1771, 1082-1093.*
Hussain et al., Diabetes Research and Clinical Practice 2007, 76, 317-326.*
Mugnier et al. J. Org. Chem. 1993, 58, 5329-5334.*
Ahn et al. J. Med. Chem. 2006, 49, 4781-4784.*
Jordan, V. C. Nature Reviews: Drug Discovery, 2, 2003, pp. 205-213.*

* cited by examiner

*Primary Examiner*—Rebecca L Anderson
*Assistant Examiner*—Matthew P Coughlin
(74) *Attorney, Agent, or Firm*—Baker & Hostetler, LLP

(57) ABSTRACT

An indene derivative for selectively modulating the activities of peroxisome proliferator activated receptors (PPARs) having the following formula (I):

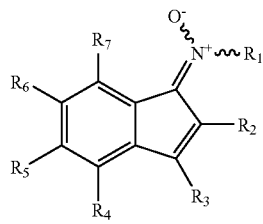

(I)

wherein,
R₁ is $C_{1-6}$ alkyl, $C_{1-6}$ alkenyl, or $C_{3-6}$ cycloalkyl, each of which is unsubstituted or substituted with one or more phenyl groups;

R₂ is H, CN, $CO_2R^a$, $CH_2CO_2R^a$, $CONR^bR^c$,

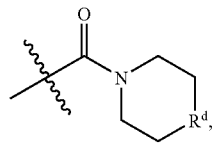

or phenyl;

R₃ is $C_{1-6}$ alkyl, $C_{3-6}$ cycloalkyl, naphthyl, phenyl,

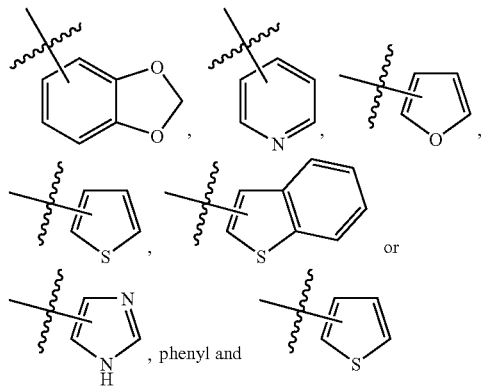

, phenyl and being each unsubstituted or substituted with one or more substituents selected from the group consisting of halogen, CN, $NH_2$, $NO_2$, $OR^a$, phenyloxy, $C_{1-6}$ alkyl, and $C_{3-6}$ cycloalkyl; and R₄, R₅, R₆, and R₇ are each independently H, OH, $OSO_2CH_3$, $O(CH_2)_mR^e$, $CH_2R^f$, $OCOCH_2OR^g$, $OCH_2CH_2OR^g$, $OCH_2CH{=}CHR^g$, or pyridine-2-yloxy, or R₅ and R₆ together form $OCH_2O$.

12 Claims, No Drawings

INDENE DERIVATIVES AND PROCESS FOR THE PREPARATION THEREOF

This application is a 35 U.S.C. 371 National Stage Filing of International Application No. PCT/KR05/01066, filed Apr. 13, 2005, which claims priority under 35 U.S.C. 119(a-d) to Korean Application No. 10-2004-0025217, filed Apr. 13, 2004.

FIELD OF THE INVENTION

The present invention relates to a novel indene derivative, which is useful as a modulator of peroxisome proliferator activated receptors (PPARs), a process for the preparation thereof and a pharmaceutical composition containing same as an active ingredient.

BACKGROUND OF THE INVENTION

Peroxisome proliferator activated receptors (PPARs) are members of the nuclear hormone receptor superfamily and function as transcription factors regulating gene expression in the form of heterodimers with retinoid X receptors (RXRs). The PPARs are divided into three subtypes, "PPAR α", "PPAR γ" and "PPAR δ", and are generally involved in maintaining energy homeostasis in vertebrates through the control of fat and glucose metabolisms.

Accordingly, many attempts have been made to develop PPAR α and PPAR γ full agonists which are useful for the treatment and prevention of disorders modulated by PPARs, e.g., metabolic syndromes such as diabetes, obesity, arteriosclerosis, hyperlipidemia, hyperinsulinism and hypertension; inflammatory diseases such as osteoporosis, liver cirrhosis and asthma; and cancer.

For example, it has been reported that thiazolidine-2,4-dione (TZD) and non-TZD-based full agonists on PPAR γ exhibit excellent blood glucose level-lowering effect in non-insulin dependent diabetes mellitus (NIDDM) mammal models (*J. Med. Chem.*, 1999, 42, 3785; *Bioorg. Med. Chem. Lett.*, 2000, 2453; *Chem. Pharm. Bull.*, 2002, 50, 1349; *Bioorg. Med. Chem. Lett.*, 2002, 77; *J. Med. Chem.*, 2003, 46, 3581.).

However, such PPAR γ full agonists are also known to cause adverse side effects including weight gain due to facilitation of fat cell differentiation, cardiac hypertrophy, edema and liver damage.

Therefore, there exists a need to develop selective PPAR modulators (SPPARMs), which are capable of selectively controlling the activities of the PPARs without causing side effects (*Molecular Cell*, 2001, 8, 737; *Molecular Endocrinology*, 2003, 17, 662; *Molecular Endocrinology*, 2002, 16, 2628).

SUMMARY OF THE INVENTION

Accordingly, it is a primary object of the present invention to provide a novel compound, which is capable of selectively modulating the activities of peroxisome proliferator activated receptors (PPARs), causing no adverse side effects.

It is another object of the present invention to provide a process for the preparation of said compound.

It is a further object of the present invention to provide a pharmaceutical composition containing said compound as an active ingredient.

In accordance with one aspect of the present invention, there is provided a novel indene derivative of formula (I) or a pharmaceutically acceptable salt thereof:

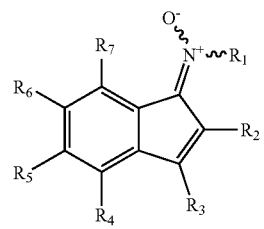

(I)

wherein, $R_1$ is $C_{1-6}$ alkyl, $C_{1-6}$ alkenyl or $C_{3-6}$ cycloalkyl, which is unsubstituted or substituted with one or more phenyl groups;

$R_2$ is H, CN, $CO_2R^a$, $CH_2CO_2R^a$, $CONR^bR^c$,

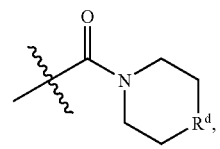

or phenyl;

$R_3$ is $C_{1-6}$ alkyl, $C_{3-6}$ cycloalkyl, or naphthyl, phenyl,

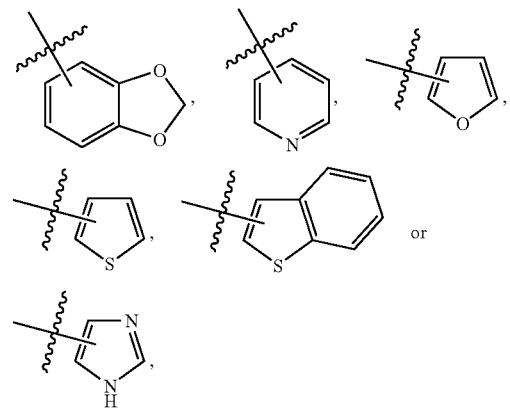

or which is unsubstituted or substituted with one or more substituents selected from the group consisting of halogen, CN, $NH_2$, $NO_2$, $OR^a$, phenyloxy, $C_{1-6}$ alkyl and $C_{3-6}$ cycloalkyl; and $R_4$, $R_5$, $R_6$ and $R_7$ are each independently H, OH, $OSO_2CH_3$, $O(CH_2)_mR^e$, $CH_2R^f$, $OCOCH_2OR^g$, $OCH_2CH_2OR^g$ or $OCH_2CH=CHR^g$, or $R_5$ and $R_6$ together form $OCH_2O$;

in which $R^a$ is H, or $C_{1-6}$ alkyl or $C_{3-6}$ cycloalkyl, which is unsubstituted or substituted with one or more halogens;

$R^b$ and $R^c$ are each independently H, $C_{1-6}$ alkyl or $C_{3-6}$ cycloalkyl;

$R^d$ is O, S or $NR^a$;

$R^e$ is H, halogen, $C_{3-6}$ cycloalkyl, naphthyl,

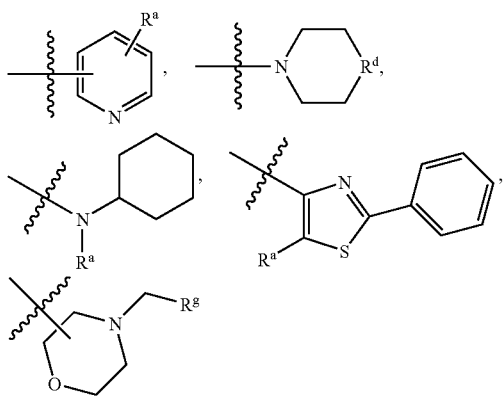

or phenyl, which is unsubstituted or substituted with one or more substituents selected from the group consisting of halogen, CN, $NH_2$, $NO_2$, $OR^a$, $CF_3$ and $COOR^a$;

$R^f$ is $OCH_2CH_2R^g$ or

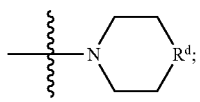

$R^g$ is phenyl, which is unsubstituted or substituted with one or more substituents selected from the group consisting of halogen, CN, $NH_2$, $NO_2$ and $OR^a$; and m is an integer in the range of 1 to 5.

DETAILED DESCRIPTION OF THE INVENTION

The indene derivatives of the present invention may include optical isomers of the compound of formula (I).

The pharmaceutically acceptable salt of the inventive indene derivative is a non-toxic addition salt generated from an inorganic acid such as hydrochloric acid, an organic acid such as trifluoroacetic acid, citric acid, lactic acid, maleic acid and fumaric acid, an inorganic base such as an alkali or alkaline earth metal (e.g., sodium, potassium, magnesium and calcium) hydroxides, bicarbonates and carbonates, or an organic base such as amines.

Among the compounds of formula (I) of the present invention, preferred are those wherein $R_1$ is $C_{1-6}$ alkyl, which is unsubstituted or substituted with a phenyl group; $R_2$ is H, CN, $CO_2R^a$, $CH_2CO_2R^a$, $CONR^bR^c$ or phenyl; $R_3$ is $C_{1-6}$ alkyl, $C_{3-6}$ cycloalkyl, or phenyl,

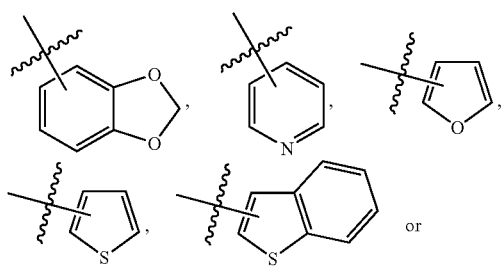

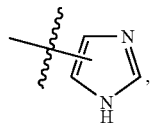

which is unsubstituted or substituted with one or more substituents selected from the group consisting of halogen, $C_{1-6}$ alkyl and $C_{3-6}$ cycloalkyl; $R_4$ and $R_7$ are H; $R_5$ and $R_6$ are each independently OH, $OSO_2CH_3$, $O(CH_2)_mR^e$, $CH_2R^f$, $OCOCH_2OR^g$, $OCH_2CH_2OR^g$ or $OCH_2CH=CHR^g$, or together form $OCH_2O$; $R^a$ is H, or $C_{1-6}$ alkyl; $R^d$ is O or $NCH_3$; $R^e$ is H, halogen, $C_{3-6}$ cycloalkyl, naphthyl,

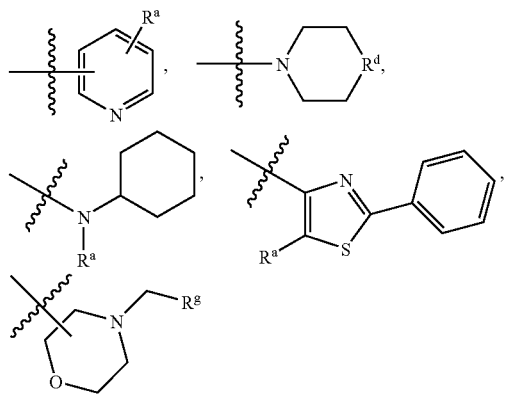

or phenyl, which is unsubstituted or substituted with one or more substituents selected from the group consisting of halogen, OH, methoxy, $CF_3$ and $COOR^a$; $R^f$ is $OCH_2CH_2R^g$ or

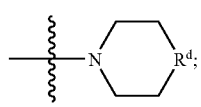

and $R^g$ is phenyl.

More preferred are those wherein $R_1$ is $CH_3$; $R_2$ is H, CN, $CO_2R^a$ or $CONR^bR^c$; $R_3$ is $C_{1-6}$ alkyl, or phenyl,

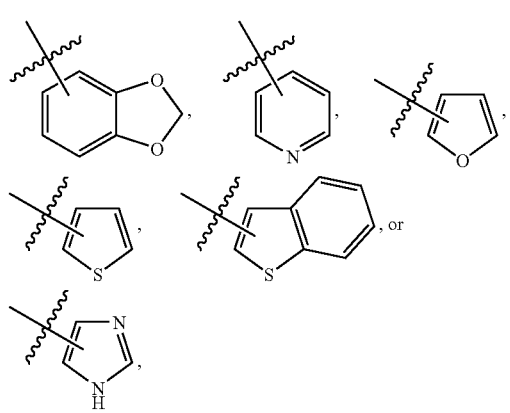

which is unsubstituted or substituted with one or more halogens or $C_{1-6}$ alkyl groups; and $R_5$ and $R_6$ are each independently $O(CH_2)_m R^e$ or $CH_2 R^f$, or together form $OCH_2O$.

The present invention also provides processes for preparing indene derivatives of formula (I).

The inventive compound of formula (I) may be prepared, for example, as shown in Reaction Scheme (I):

In case the compound of formula (I) is synthesized according to Reaction Scheme (I), a mixture of geometric isomers comprising cis and trans compounds about the imine double bond is obtained, and each pure isomer can be isolated by column chromatography. Each of the cis and trans isomer can be converted to the other isomer under suitable reaction condition. For example, the cis or trans compound is converted

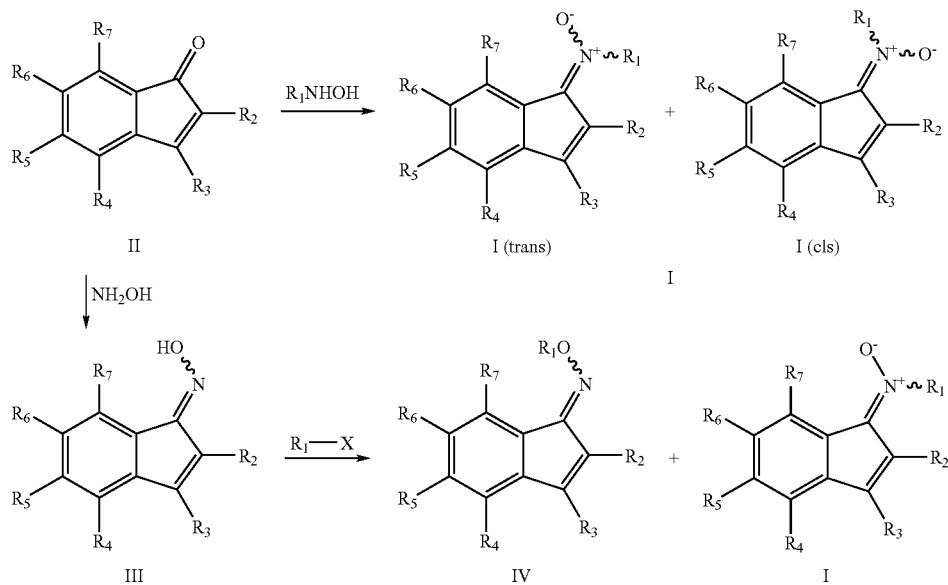

Reaction Scheme (I)

wherein, $R_1$ to $R_7$ have the same meanings as defined in formula (I), and X is halogen.

In Reaction Scheme (I), a compound of formula (II) may be stirred with alkyl hydroxylamine having various substituents or its hydrochloride salt in the presence of a suitable base under a nitrogen atmosphere to obtain a compound of formula (I) until the compound of formula (II) is entirely consumed. At this time, 2 to 10 equivalents of alkyl hydroxylamine or its hydrochloride is used, and cis and trans compounds (geometric isomers) of formula (I) are obtained together. Examples of the desirable reaction solvent that can be used in this reaction are dimethylformamide, nitroethane, methanol or ethanol, and 2 to 10 equivalents of amines such as 2,6-lutidine or pyridine is used at a temperature in the range of 50 to 120° C. for 12 to 36 hours, preferably in a pressure reactor.

Alternatively, a compound of formula (II) can be stirred with hydroxylamine or its hydrochloride salt under in the presence of a suitable base to obtain a compound of formula (III) until the compound of formula (II) is entirely consumed. In this reaction, 2 to 10 equivalents of hydroxylamine or its hydrochloride salt is used. Examples of the desirable reaction solvent can be used in this reaction are methanol and ethanol, and 2 to 10 equivalents of amines such as pyridine is used at a temperature of 20 to 100° C. for 3 to 12 hours.

Also, a compound of formula (III) can be reacted with 1 to 3 equivalents of alkyl halide in a solvent such as dimethyl formamide or acetone in the presence of an inorganic base such as potassium carbonate to obtain a compound of formula (I). At this time, the alkoxy imine form of the compound of formula (IV) is synthesized together.

partly to the other isomer when it is stirred for a long period of time in the presence of an inorganic base such as lithium hydroxide in an alcohol solvent such as methanol or ethanol. Most of the cis isomer is converted to the trans isomer in 1-2 hours when it is heated at 110° C. in an organic solvent such as benzene, toluene or xylene. A similar isomer conversion reaction can be carried out photochemically when an isomer is irradiated with intense visible or ultraviolet light.

The compound of formula (II) may be obtained by the method described in *Tetrahedron*, 1995, 51, 12179; *J. Org. Chem.*, 1993, 58, 4579; *J. Chem. Soc., Perkin Trans I.*, 1992, 2985; *Synthesis*, 1991, 115 & 176; *J. Med. Chem.*, 1998, 31, 1316 & 1754, as shown in Reaction Schemes (II) to (VII).

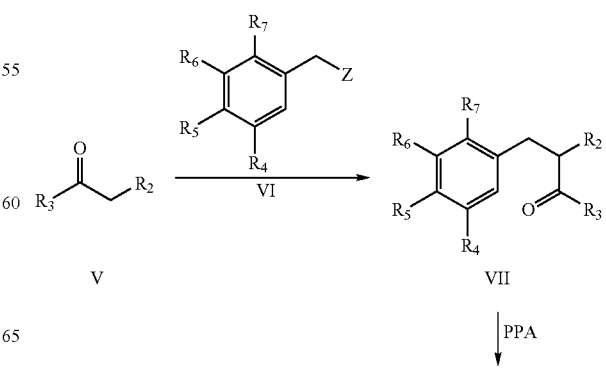

Reaction scheme (II)

-continued

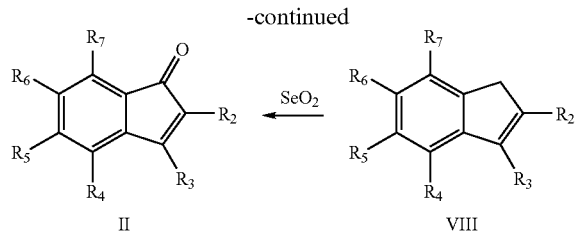

wherein,

R$_2$ to R$_7$ have the same meanings as defined in formula (I), and Z is halogen or an activated leaving group.

1) The compounds of formula (V) and (VI), which are commercially available or easily prepared in accordance with the conventional procedures, may be reacted with each other to obtain the compound of formula (VII). Z of the compound of formula (VI) is halogen or an activated leaving group such as methane sulfonate. 2 to 10 equivalents of an inorganic base such as potassium carbonate, and a polar solvent such as acetone or dimethyl formamide are preferably used. If necessary, 1-3 equivalents of sodium iodide or potassium iodide are added to facilitate the reaction. Desirably, the reaction is carried out at 20 to 50° C. for 3 to 15 hours.

2) The compound of formula (VII) may be reacted with polyphosphoric acid (PPA) which also acts as a solvent (5-10 equivalents) at 30 to 50° C. for a period of 3 to 12 hours to obtain the cyclized compound of formula (VIII). Xylene may be used as a co-solvent, and methane sulfonic acid (MSA) or pyridium toluene sulfonate (PPTS) may be used in place of polyphosphoric acid under different conditions.

3) The compound of formula (VIII) may be oxidized to the compound of formula (II) by using a common oxidant. For example, an excess amount (5-15 equivalents) of selenium dioxide as the most preferable oxidant may be used in a solvent such as 1,4-dioxane or tetrahydrofuran at 50-120° C. for 7-15 hours to obtain the oxidized compound of formula (II).

wherein,

R$_2$ to R$_7$ have the same meanings as defined in formula (I).

In the first step of Reaction Scheme (III), equivalent amounts of compounds of formula (IX) and (X), which are commercially available or easily prepared in accordance with the conventional procedures, may be subjected to a condensation reaction to obtain the compound of formula (XI) in the presence of 2 to 5 equivalents of an amine base such as piperidine or an inorganic base such as sodium hydroxide using a polar solvent such as dimethylformamide, ethanol or nitroethane. Desirably, the reaction is carried out at 20 to 80° C. for 3 to 15 hours.

In the second step, the compound of formula (XI) is reacted with an excess amount of methane sulfonic acid (MSA), pyridinium toluene sulfonate (PPTS) or polyphosphoric acid (PPA) at 20 to 50° C. for 3 to 12 hours in a solvent such as dichloromethane, chloroform, carbon tetrachloride or xylene, to obtain the cyclized compound of formula (XII). In case the compound of formula (XI) is reacted with aluminum chloride in anhydrous nitroethane under a nitrogen gas, it is subjected to the both condensation and cyclization reactions to obtain the compound of formula (XII).

In the third step, the compound of formula (XII) is oxidized to the compound of formula (II) using a common oxidants such as phenyl selenium chloride and hydrogen peroxide. The compound of formula (XII) is reacted with 1-3 equivalents of selenium dioxide in the presence of an amine base such as 1-5 equivalents of pyridine. An excess amount of 30% hydrogen peroxide may be added to obtain the compound of formula (II) in a high yield. The reaction may be carried out in a solvent such as dichloromethane, chloroform, carbon tetrachloride or 1,4-dioxane at 20-70° C. for 3-15 hours.

Reaction Scheme (III)

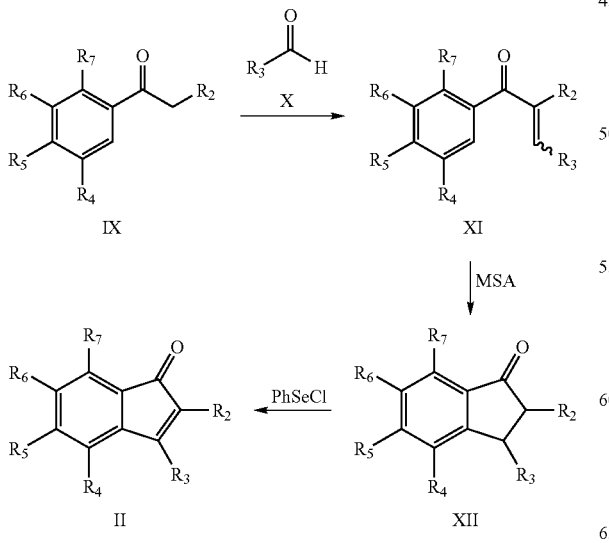

Reaction Scheme (IV)

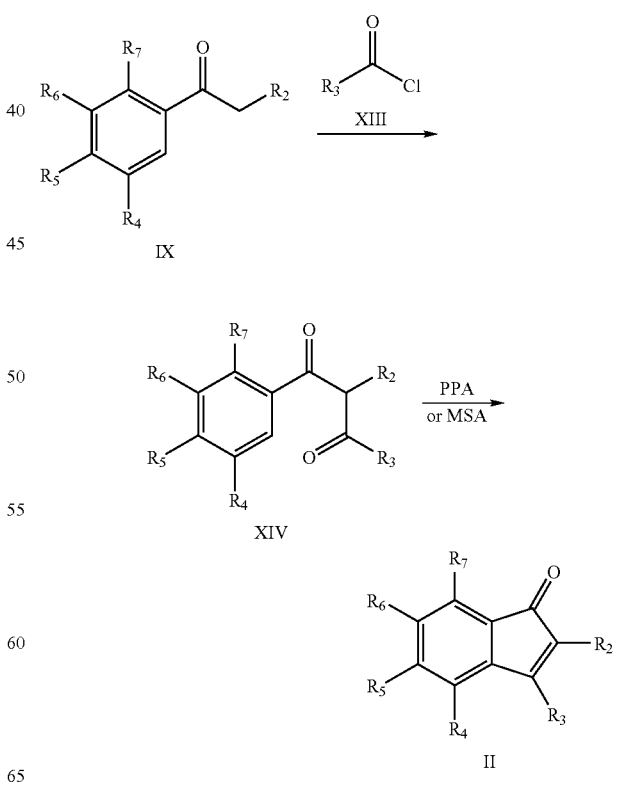

wherein,

R$_2$ to R$_7$ have the same meanings as defined in formula (I).

In the first step of Reaction Scheme (IV), equivalent amount of compounds of formula (IX) and (XIII), which are commercially available or easily prepared in accordance with the conventional procedures, are subjected to a condensation reaction to obtain the compound of formula (XIV). 2 to 5 equivalents of an amine base such as piperidine and an inorganic base such as sodium hydroxide, and a solvent such as tetrahydrofuran or dimethyl formamide may be used in the reaction which is preferably carried out at 20 to 70° C. for 3 to 15 hours.

In the second step, the compound of formula (XIV) is reacted with an excess amount of methanesufonic acid (MSA), pyridinium toluene sulfonate (PPTS) or polyphosphoric acid (PPA) at 20 to 50° C. to obtain the cyclized compound of formula (II). The reaction may be carried out in dichloromethane, chloroform, carbon tetrachloride or xylene for 3 to 12 hours.

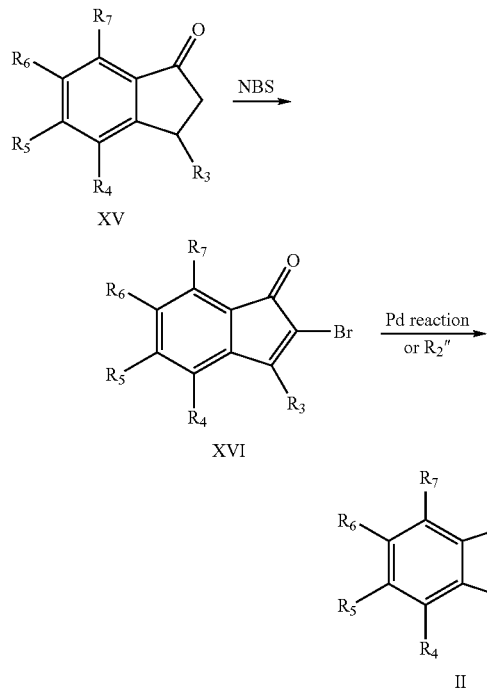

wherein,

R$_2$ to R$_7$ have the same meanings as defined in formula (I).

In the first step of Reaction Scheme (V), the compound of formula (XV), which is commercially available or easily prepared in accordance with the conventional procedures is subjected to bromination to obtain the compound of formula (XVI) by treating with 1 to 3 equivalents of N-bromosuccinimide (NBS) in carbon tetrachloride under infrared irradiation at 50 to 100° C., for 0.5 to 3 hours. The compound of formula (XVI) can also be obtained by using a catalytic amount of a radical reaction initiator (e.g., azobisisobutyronitrile) instead of infrared irradiation.

In the second step, the compound of formula (XVI) is subjected to a carbon-carbon coupling reaction in the presence of a palladium catalyst to obtain the compound of formula (II) according to the procedure of the well-known Suzuki reaction or Heck reaction.

Also, the bromine substituent of the compound of formula (XVI) may be replaced with R$_3$ using a suitable nucleophilic agent. The compound of formula (XVI) may be reacted with 1-5 equivalents of copper (I) cyanide or sodium methane sulfonate at 70-150° C. in a polar solvent such as nitroethane or dimethylformamide for 3-15 hours to obtain the compound of formula (II)

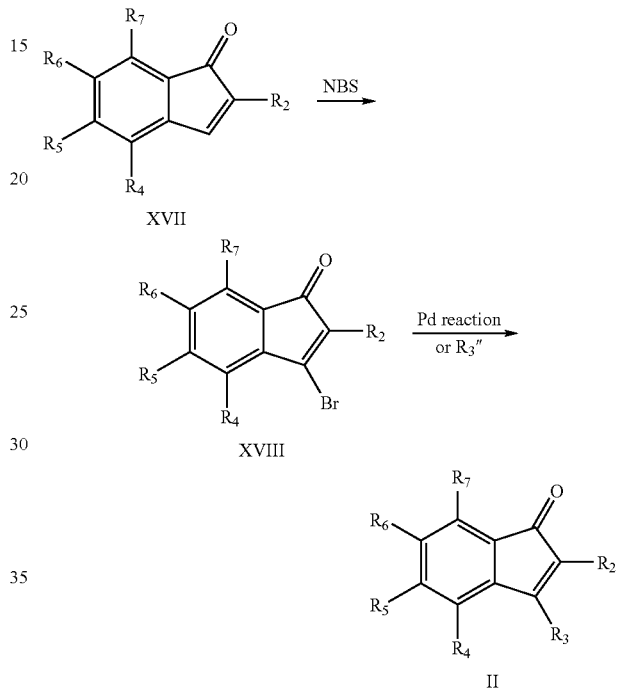

wherein,

R$_2$ to R$_7$ have the same meanings as defined in formula (I).

In the first step of Reaction Scheme (VI), the compound of formula (XVII), which is synthesized as an intermediate in Reaction Schemes (II) to (V) or easily prepared in accordance with the conventional procedures, is brominated to obtain the compound of formula (XVIII) using 1-3 equivalents of N-bromosuccinimide (NBS) in carbon tetrachloride under infrared irradiation. This reaction may be carried out at 50 to 100° C. for 0.5 to 3 hours. The compound of formula (XVIII) can also be obtained by using a catalytic amount of a radical reaction initiator (e.g., azobisisobutyronitrile) instead of infrared irradiation.

In the second step, the compound of formula (XVIII) may be subjected to a carbon-carbon coupling reaction using a palladium catalyst according to the procedure of Suzuki reaction, Heck reaction or Stille reaction to obtain the compound of formula (II) having various substituents at R$_3$.

Also, the bromine substituents of the compound of formula (XVIII) may be replaced with R$_3$ using a suitable nucleophilic agent. The compound of formula (XVII) may be reacted with 1-5 equivalents of copper cyanide, sodium methane sulfonate, amine or alkoxide in a polar solvent such as nitroethane or dimethylformamide at 70-150° C. for 3-15 hours to obtain the compound of formula (II).

In case the benzene ring of indene of formula (II) obtained in Reaction Schemes (II) to (VI) has a hydroxy, thiol, amino, alkyl, halogen or alkyl hydroxy substituents, various substituents can be further introduced to the benzene ring of the indene according to Reaction Scheme (VII).

Reaction Scheme (VII)

[Structure XIX: indenone with Y—(CH₂)n— substituent, R₂, R₃]

→

[Structure II: indenone with R₄, R₅, R₆, R₇ on benzene ring, R₂, R₃]

wherein, $R_2$ to $R_7$ have the same meanings as defined in formula (I), Y is hydroxy, thiol, amino, $C_{1-6}$ alkyl or halogen, and n is an integer in the range of 0 to 5.

In case that Y of the compound of formula (XIX) is hydroxy, thiol or amino, the compound may be acylated with various carboxylic acids or derivatives thereof to obtain the compound of formula (II) having various substituents. When a carboxylic acid is used in the acylation, the compound of formula (XIX) is reacted with equal amounts of a carboxylic acid and a condensation reagent such as dicyclohexylcarbodiimide (DCC) in dichloromethane at room temperature for 1-12 hours to obtain the compound of formula (II).

When an acid chloride is used, an equivalent amount of an acid chloride and 1-2 equivalents of an amine base such as triethylamine and pyridine are used to carry out the reaction in dichloromethane at 0-30° C. for 1-5 hours to obtain the compound of formula (II).

Also, the compound of formula (II) having an introduced sulfide, ether or alkylamino group may be obtained easily by a conventional alkylation reaction such as Mitsunobu reaction. In Mitsunobu reaction, 1-3 equivalents of an alcohol, triphenyl phosphine, and DEAD (diethyl azodicarboxylate) or DIAD (diisopropyl azodicarboxylate) are stirred in tetrahydrofuran or benzene at 0-30° C. for 1-12 hours to obtain the compound of formula (II).

In addition, the compound of formula (II) may be obtained by alkylating with haloalkyl substituted with an alkyl or aryl group in the presence of a base such as sodium hydride, potassium carbonate and sodium hydroxide, in acetone or N,N-dimethylformamide at 20-100° C. for 3-12 hours.

2) In case that Y of the indene compound of formula (XIX) is $C_{1-6}$ alkyl, a halogen substituents may be introduced by halogenation, and then substituting the halogen with a suitable nucleophile to obtain the compound of formula (II). The halogenation may be conducted in a conventional way. For example, bromination may be conducted using 1-3 equivalents of NBS in carbon tetrachloride under infrared irradiation at 50 to 100° C. for 0.5 to 3 hours. The bromination can also be conducted using a catalytic amount of a radical reaction initiator (e.g., azobisisobutyronitrile) instead of infrared irradiation.

The intermediate obtained by halogenation may be subjected to a substitution reaction an alkyl, aryl or heterocycle compound having various substituents such as hydroxy, amino, thiol, or carboxylic acid substituents under conventional reaction conditions to obtain the title compound of formula (II). Generally, the reaction is conducted with 1-2 equivalents of the nucleophile in a solvent such as dichloromethane, tetrahydrofuran or dimethylformamide in the presence of 1-3 equivalents of an inorganic base such as potassium carbonate or amine base such as triethylamine at 0-70° C. for 1-7 hours. 1-3 equivalents of sodium iodide may be added to enhance the reaction.

The compound of formula (XIX) may also be subjected to a carbon-carbon coupling reaction using a palladium catalyst according to the procedure of Suzuki reaction, Heck reaction or Stille reaction to obtain the compound of formula (II) having various substituents such as alkyl, aryl or heterocycle, when n and Y of the indene of formula (XIX) are 0 and halogen, respectively.

Exemplary compounds of formula (I) of the present invention, which can be prepared in accordance with the methods described above, are listed in Table 1:

TABLE 1

| No. | structure | ¹H-NMR(CDCl₃, 300 M Hz) δ |
|---|---|---|
| 1 | [Structure of indene derivative with methoxy, N⁺-O⁻, ethyl ester, phenyl groups] | 8.28(d, J=2.4 Hz, 1H), 7.44-7.42 (m, 5H), 7.16 (d, J=8.4 Hz, 1H), 6.86 (dd, J=8.4 Hz, J=2.4 Hz, 1H), 4.16 (q, J=7.1 Hz, 2H), 4.13 (s, 3H), 3.89 (s, 3H), 1.05 (t, J=7.1 Hz, 3H) |

TABLE 1-continued

| No. | structure | $^1$H-NMR(CDCl$_3$, 300 M Hz) δ |
|---|---|---|
| 2 | 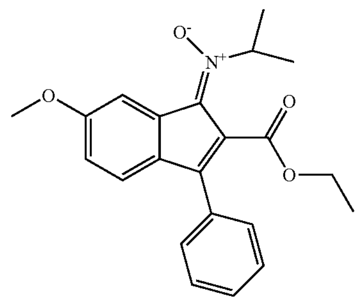 | 8.41(d, J=2.2 Hz, 1H), 7.45(s, 5H), 7.17(d, J=8.4 Hz, 1H), 6.89(dd, J=8.4, 2.4 Hz, 1H), 4.90 4.80(m, 1H), 4.15(q, J=7.0 Hz, 2H), 3.91(s, 3H), 1.53(d, J=6.3 Hz, 6H), 1.06(t, J=7.1 Hz, 3H) |
| 3 | 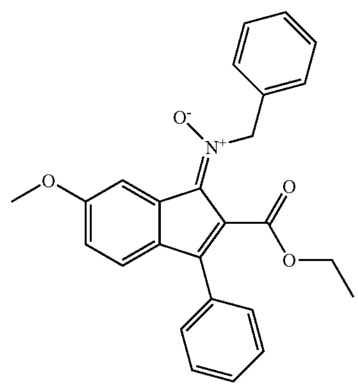 | 8.38(d, J=2.2 Hz, 1H), 7.43-7.34(m, 10H), 7.16(d, J=8.6 Hz, 1H), 6.80(dd, J=8.3, 2.2 Hz, 1H), 5.55(s, 2H), 4.01(q, J=7.1 Hz, 2H), 3.86(s, 3H), 0.89(t, J=7.1 Hz, 3H) |
| 4 | 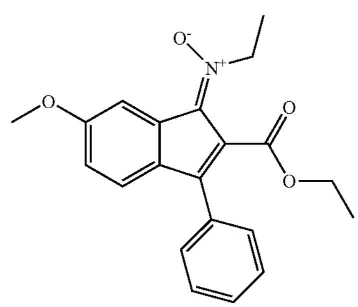 | 8.35(d, J=2.2 Hz, 1H), 7.43(s, 5H), 7.16(d, J=8.2 Hz, 1H), 6.86(dd, J=8.4, 2.2 Hz, 1H), 4.28(q, J=7.0 Hz, 2H), 4.12(q, J=7.0 Hz, 2H), 3.89(s, 3H), 1.25(t, J=7.0 Hz, 3H), 1.03(t, J=7.1 Hz, 3H) |
| 5 | 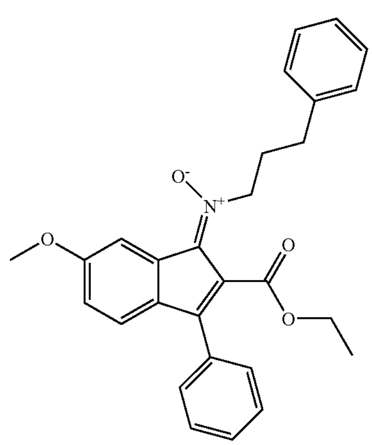 | 8.34(d, J=2.2 Hz, 1H), 7.43(s, 5H), 7.27-7.13(m, 6 H), 6.87(dd, J=8.3, 2.2 Hz, 1H), 4.27(t, J=6.4 Hz, 2H), 4.03(q, J=7.0 Hz, 2H), 3.89(s, 3H), 2.73(t, 3 =6.4 Hz, 2H), 2.42-2.36(m, 2H), 0.97(t, 3 =7.0 Hz, 3H) |

TABLE 1-continued

| No. | structure | ¹H-NMR(CDCl₃, 300 M Hz) δ |
|---|---|---|
| 6 | 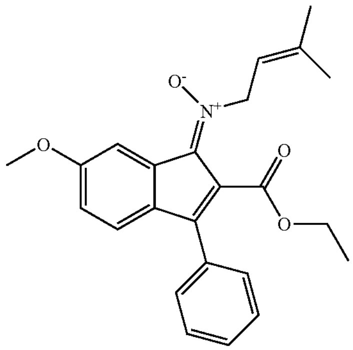 | 8.33(d, J=2.6 Hz, 1H), 7.43(s, 5H), 7.15(d, 38.4 Hz, 1H), 6.83(q, J=8.4, 2.6 Hz, 1H), 5.50(t, J=6.5 Hz, 1H), 4.92(d, J=6.5 Hz, 2H), 4.09(q, J=7.0 Hz, 2H), 3.87(s, 3H), 1.79(d, J=2.2 Hz, 6H), 1.00(t, J=7.0 Hz, 3H) |
| 7 | 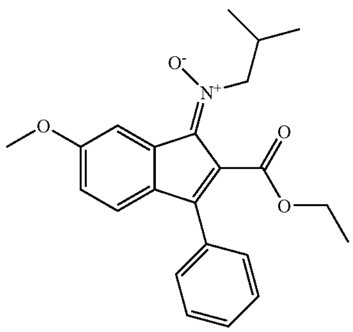 | 8.37(d, J=2.6 Hz, 1H), 7.43(s, 5H), 7.17(d, J=8.4 Hz, 1H), 6.86(dd, J=8.4, J=2.6 Hz, 1H), 4.35-4.04(m, 4H), 3.89(s, 3H), 2.45(m, 1H), 1.05-0.97(m, 9H) |
| 8 | 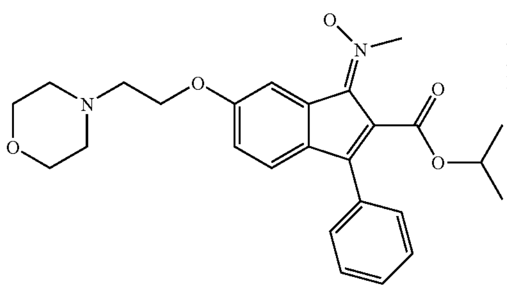 | 8.27(d, J=2.6 Hz, 1H), 7.49-7.31(m, 5H), 7.13(d, J=8.2 Hz, 1H), 6.85(dd, J=8.2, 2.6 Hz, 1H), 5.02(sept, J=6.6 Hz, 1H), 4.27-4.10(m, 5H), 3.74(t, J=4.6 Hz, 4H), 2.83(t, J=5.6 Hz, 2H), 2.59(t, J=4.6 Hz, 4H), 1.05(d, J=6.6 Hz, 6H), mp 79-81° C. |
| 9 | 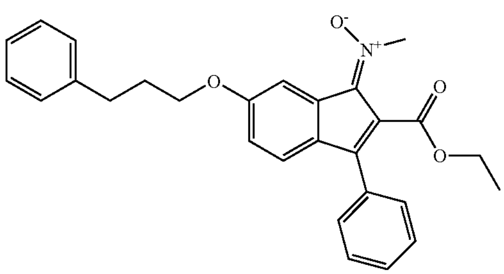 | 8.27(d, J=2.2 Hz, 1H), 7.43(s, 5H), 7.31-7.17(m, 5H), 7.15(d, J=8.1 Hz, 1H), 6.84(dd, J=8.2, 2.2 Hz, 1H), 4.16-4.03(m, 7H), 2.82(t, J=7.1 Hz, 2H), 2.20-2.10(m, 2H), 1.04(t, J=7.1 Hz, 3H) |
| 10 | 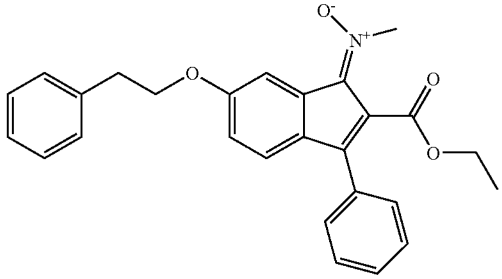 | 8.30(d, J=2.4 Hz, 1H), 7.51-7.24(m, 10H), 7.16(d, J=8.3 Hz, 1H), 6.85(dd, J=8.3, 2.4 Hz, 1H), 4.31-4.08(m, 7H), 3.13(t, J=7.1 Hz, 2H), 1.05(t, J=7.1 Hz, 3H) |

TABLE 1-continued

| No. | structure | $^1$H-NMR(CDCl$_3$, 300 M Hz) δ |
|---|---|---|
| 11 | 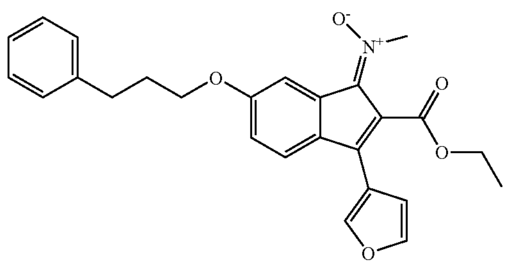 | 8.28(d, J=2.4 Hz, 1H), 7.86(dd, J=1.4, 0.8 Hz, 1H), 7.54(dd, J=1.8, 1.4 Hz, 1H), 7.38-7.19(m, 6H), 6.90(dd, J=8.4, 2.4 Hz, 1H), 6.68(dd, J=1.8, 0.8 Hz, 1H), 4.31(q, J=7.1 Hz, 2H), 4.1-4.01(m, 5H), 2.84(t, 2H), 2.20-2.10(m, 2H), 1.28(t, J=7.1 Hz, 3H) |
| 12 | 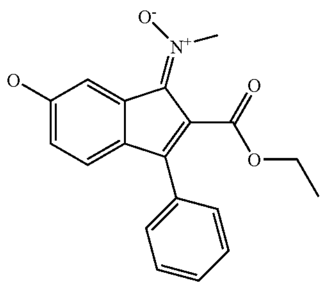 | 9.42(brs, 1H), 8.60(d, J=2.2 Hz, 1H), 7.44(s, 5H), 7.11(d, J=8.2 Hz, 1H), 6.85(dd, J=8.2, 2.2 Hz, 1H), 4.14(q, J=7.1 Hz, 2H), 1.03(t, J=7.1 Hz, 3H) |
| 13 | 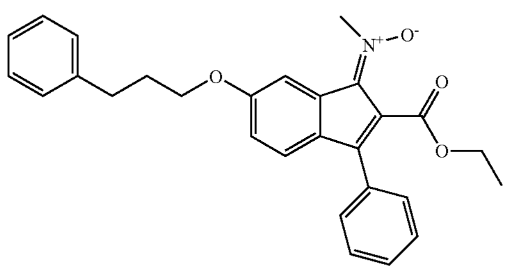 | 7.57-7.53(m, 2H), 7.47-7.40(m, 3H), 7.32-7.20(m, 6H), 7.08(d, J=1.9 Hz, 1H), 6.74(dd, 1 8.6, 1.9 Hz, 1H), 4.27(q, J=7.1 Hz, 2H), 4.24(s, 3H), 4.01(t, J=6.4 Hz, 2H), 2.84(t, J=7.5 Hz, 2H), 2.84(t, J=7.5 Hz, 2H), 2.20-2.10(m, 2H), 1.24(t, J=7.1 Hz, 3H) |
| 14 | 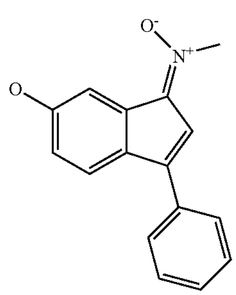 | 9.69(br, 1H), 8.59(s, 1H), 7.64-7.36(m, 5H), 7.38(d, J=8.2 Hz, 1H), 6.85(dd, J=8.2, 2.2 Hz, 1H), 6.29(s, 1H), 4.13(s, 1H) |
| 15 | 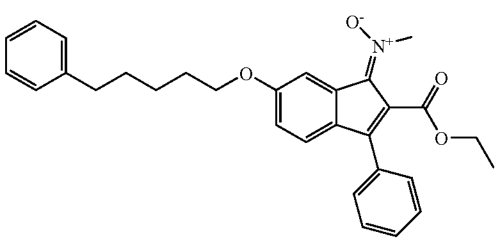 | 8.26(d, J=2.4 Hz, 1H), 7.44-7.42(m, 5H), 7.28-7.13(m, 6H), 6.83(dd, J=8.4, 2.4 Hz, 1H), 4.16-4.08(m, 5H), 4.04(t, J=6.6 Hz, 2H), 2.65(t, J=7.2 Hz, 2H), 1.90-1.80(m, 2H), 1.70-1.64(m, 2H), 1.60-1.50(m, 2H), 1.04(t, J=7.1 Hz, 3H) |

TABLE 1-continued

| No. | structure | $^1$H-NMR(CDCl$_3$, 300 M Hz) δ |
|---|---|---|
| 16 | 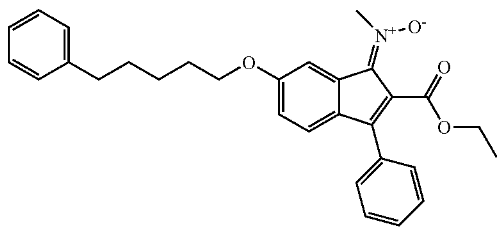 | 7.57-7.54(m, 2H), 7.43-7.41(m, 3H), 7.31-7.07(m, 6H), 7.07(d, J=2.1 Hz, 1H), 6.77(dd, J=8.4, 2.1 Hz, 1H), 4.30-4.28(m, 5H), 3.99(t, J=6.6 Hz, 2H), 2.66(t, J=7.2 Hz, 2H), 1.90-1.80(m, 2H), 1.73-1.66(m, 2H), 1.59-1.51(m, 2H), 1.25(t, J=7.1 Hz, 3H) |
| 17 | 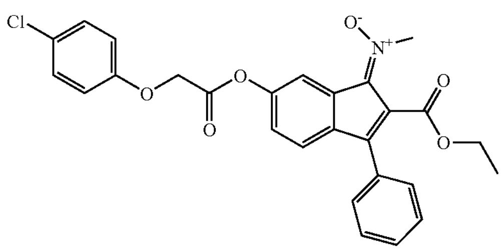 | 8.37(d, J=2.1 Hz, 1H), 7.45-7.42(m, 5H), 7.30-7.26(m, 3H), 7.11(dd, J=8.1, 2.1 Hz, 1H), 6.93(d, J=8.7 Hz, 2H), 4.88(s, 2H), 4.19-4.09(m, 5H), 1.06(t, J=7.1 Hz, 3H) |
| 18 | 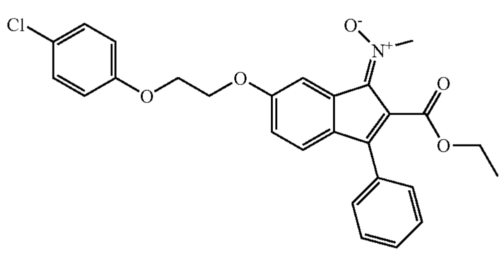 | 8.32(d, J=2.4 Hz, 1H), 7.44(s, 5H), 7.29-7.16(m, 3H), 6.94-6.87(m, 3H), 4.44-4.19(m, 4H), 4.17-4.07(m, 5H), 1.05(t, J=7.1 Hz, 3H) |
| 19 | 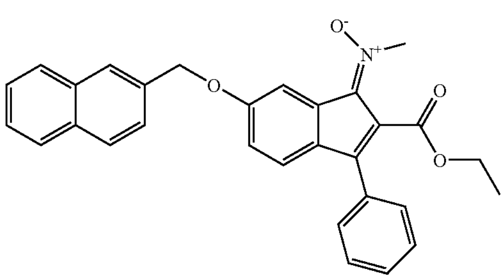 | 8.44(d, J=2.8 Hz, 1H), 7.92-7.82(m, 4H), 7.59-7.44(m, 8H), 7.18(d, J=8.3 Hz, 1H), 6.96(dd, J=8.4, 2.6 Hz, 1H), 5.32(s, 2H), 4.19-4.07(m, 5H), 1.05(t, J=7.0 Hz, 3H) |
| 20 | 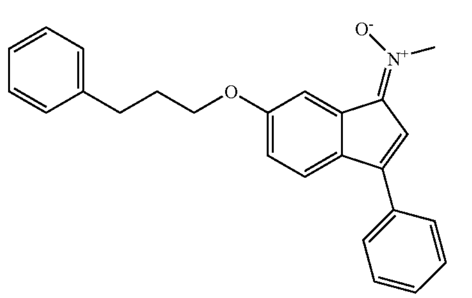 | 8.22(d, J=2.4 Hz, 1H), 7.65-7.18(m, J=1H), 6.87(dd, J=8.3, 2.4 Hz, 1H), 6.41(s, 1H), 4.12(s, 3H), 4.07(t, J=6.2 Hz, 2H), 2.83(t, J=7.2 Hz, 2H), 2.12(m, 2H) |
| 21 | 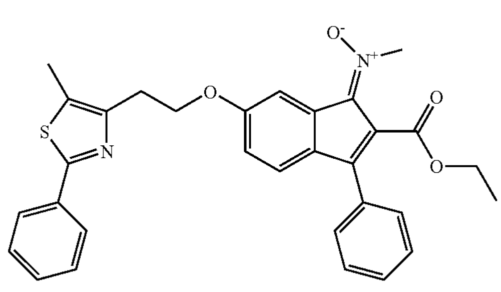 | 8.28(d, J=2.4 Hz, 1H), 7.88-7.85(m, 2H), 7.43-7.36(m, 8H), 7.14(d, J=8.1 Hz, 1H), 6.85(dd, J=8.1, 2.4 Hz, 1H), 4.41(t, J=6.9 Hz, 2H), 4.12(q, J=7.1 Hz, 2H), 4.11(s, 3H), 3.22(t, J=6.6 Hz, 3H), 2.47(s, 3H), 1.04(t, J=7.1 Hz, 3H) |

TABLE 1-continued

| No. | structure | $^1$H-NMR(CDCl$_3$, 300 M Hz) δ |
|---|---|---|
| 22 | 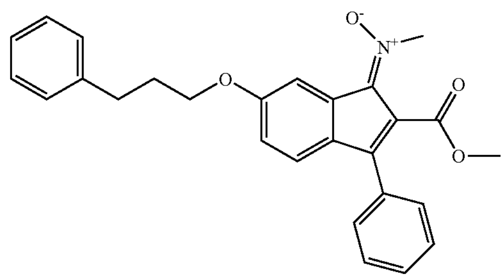 | 8.27(d, J=2.0 Hz, 1H), 8.27(s, 5H), 7.29-6.81(m, 7H), 4.11(s, 3H), 4.06(t, J=6.3 Hz, 2H), 3.67(s, 3H), 2.83(t, J=7.1 Hz, 2H), 2.13(quint, J=6.5 Hz, 2H) |
| 23 | 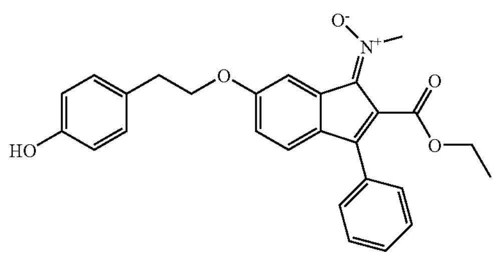 | 8.28(d, J=2.4 Hz, 1H), 7.43(s, 5H), 7.25-7.07(m, 3H), 6.86-6.76(m, 3H), 5.09(brs, 1H), 4.27-4.03(m, 7H), 3.04(t, J=7.0 Hz, 2H), 1.04(t, J=7.1 Hz, 3H) |
| 24 | 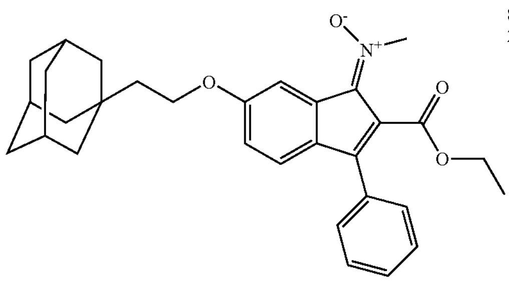 | 8.26(d, J=2.4 Hz, 1H), 7.43(m, 5H), 7.18(d, J=8.2 Hz, 1H), 6.83(dd, J=8.2, 2.4 Hz, 1H), 4.29-4.04(m, 7H), 1.96-1.50(m, 15H), 1.04(t, J=7.1 Hz, 3H) |
| 25 | 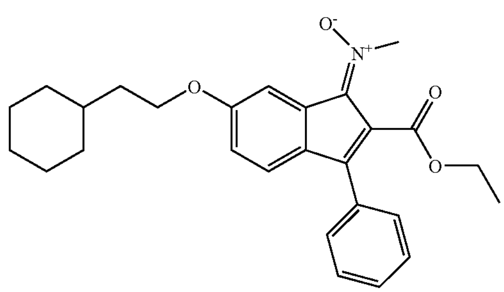 | 8.26(d, J=2.2 Hz, 1H), 7.43(m, 5H), 7,25(d, J=8.2 Hz, 1H), 6.84(dd, J=8.2, 2.2 Hz, 1H), 4.28-4.04(m, 7H), 1.79-0.76(m, 13H) |
| 26 | 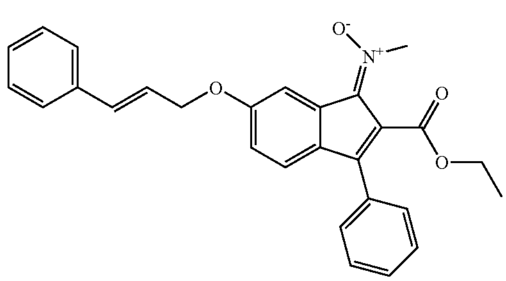 | 8.35(d, J=2.4 Hz, 1H), 7.44-7.12(m, 11H), 6.91(dd, J=8.4, 2.4 Hz, 1H), 6.77(d, J=15.8 Hz, 1H), 6.47-6.41(m, 1H), 4.82-4.76(m, 2H), 4.29-4.08(m, 5H), 1.05(t, J=7.2 Hz, 3H) |

TABLE 1-continued

| No. | structure | $^1$H-NMR(CDCl$_3$, 300 M Hz) δ |
|---|---|---|
| 27 | 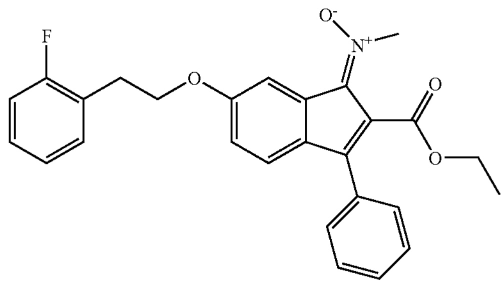 | 8.27(d, J=2.4 Hz, 1H), 7.43(s, 5H), 7.3-7.04(m, 5H), 6.84(dd, J=1H), 4.27 (t, J=6.8 Hz, 2H), 4.16 -4.09(m, 7H), 3.16(t, J=6.8 Hz. 2H), 1.04 Ct, J=7.1 Hz, 3H) |
| 28 | 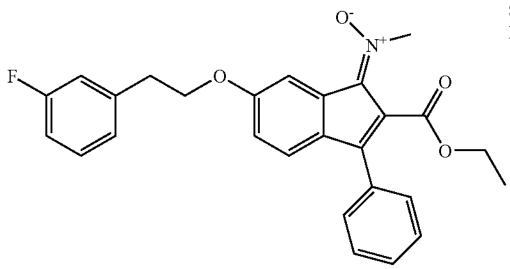 | 8.27(d, J=2.1 Hz, 1H), 7.43(s, 5H), 7.31-6.93(m, 5H), 6.84(dd, J=8.4, 2.4 Hz, 1H), 4.26(t, J=6.9 Hz, 2H), 4.16-4.09(m, 5H), 3.16(t, J=6.9 Hz. 2H), 1.04(t, J=7.0 Hz, 3H) |
| 29 | 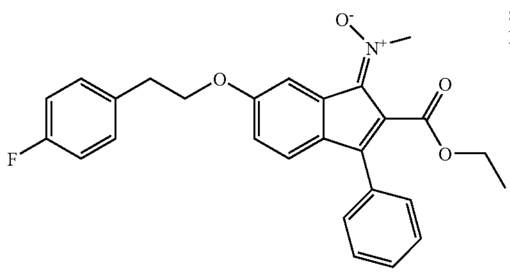 | 8.27(d, J=2.4 Hz, 1H), 7.43(s, 5H), 7.31-6.95(m, 5H), 6.83(dd, J=8.4, 2.2 Hz, 1H), 4.21(t, J=6.8 Hz, 2H), 4.14-4.09(m, 5H), 3.11(t, J=6.8 Hz, 2H), 1.04(t, J=7.1 Hz, 3H) |
| 30 | 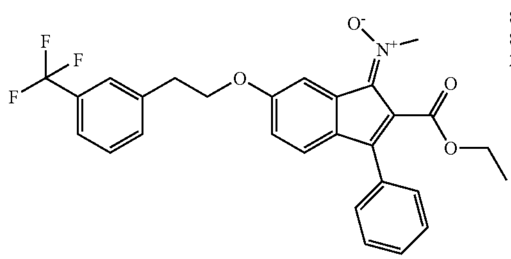 | 8.27(d, J=2.6 Hz, 1H), 7.55-7.44(m, 9H), 7.15(d, J=8.4 Hz, 1H), 6.84(dd, J= 8.4, 2.4 Hz, 1H), 4.29(t, J=6.6 Hz, 2H), 4.18-4.03(m, 5H), 3.18(t, J=6.8 Hz, 2H), 1.04(t, J=7.1 Hz, 3H) |
| 31 | 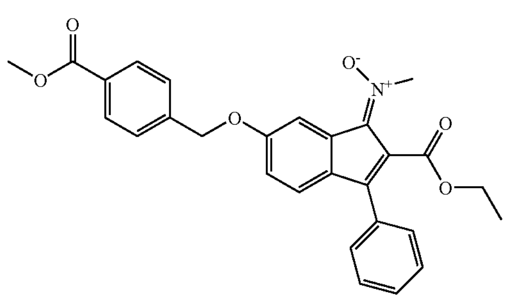 | 8.37(d, J=2.2 Hz, 1H), 8.07(m, 2H), 7.55-7.15(m, 8H), 6.93(dd, J=8.4, 2.2 Hz, 1H), 5.12(s, 2H), 4.28-4.03(m, 5H), 3,92(s, 3H), 1.05(t, J=7.1 Hz, 3H) |

TABLE 1-continued

| No. | structure | $^1$H-NMR(CDCl$_3$, 300 M Hz) δ |
| --- | --- | --- |
| 32 | 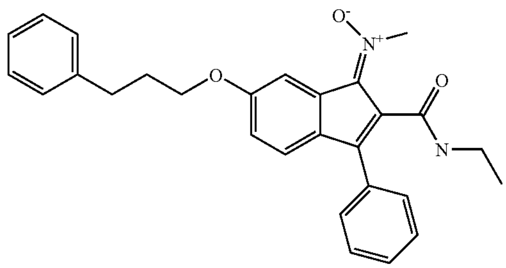 | 8.27(d, J=2.4 Hz, 1H), 7.69-6.90(m, 12H), 5.57(t, J=4.5 Hz, 1H), 4.19(s, 3H), 4.05(t, J=6.3 Hz, 2H), 3.22(t, J=7.2 Hz, 1H), 2.82(t, J=7.1 Hz, 2H), 2.14 (quint, J=6.5 Hz, 2H), 0.88(t, J=7.2 Hz, 3H) |
| 33 | 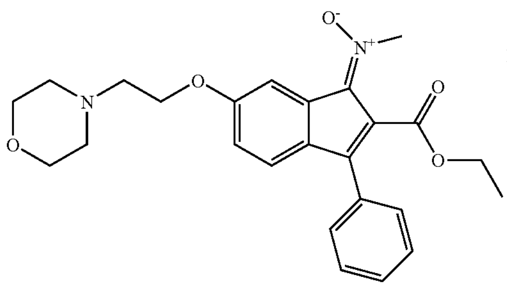 | 8.28(d, J=2.6 Hz, 1H), 7.43(s, 5H), 7.16(d, J=8.2 Hz, 1H), 6.86(dd, J=8.2, 2.6 Hz, 1H), 4.22 -4.09(m, 7H), 3.74(t, J=4.5 Hz, 4H), 2.82(t, J=5.6 Hz, 2H), 2.59(t, J=4.5 Hz, 4H), 1.04(t, J=7.1 Hz, 3H), mp 102-104° C. |
| 34 | 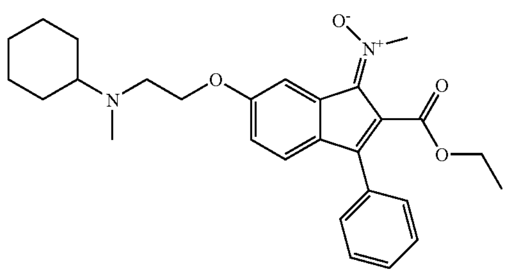 | 8.27(d, J=2.4 Hz, 1H), 7.44(s, 5H), 7.15(d, J=8.4 Hz, 1H), 6.86(dd, J=8.4, 2.4 Hz, 1H), 4.26(m, 1H), 4.16 -4.10(m, 7H), 2.91(t, J=5.9 Hz, 2H), 2.47-2.40(m, 4H), 1.92-1.72(m, 8H), 1.70-1.60(m, 2H), 1.04(t, J=7.2 Hz, 3H) |
| 35 | 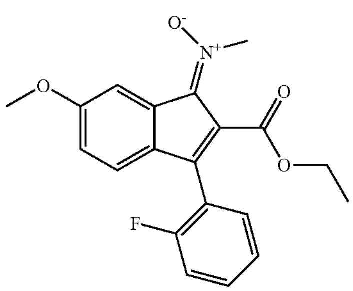 | 8.28(d, J=2.7 Hz, 1H), 7.41-7.14(m, 4H), 7.05(d, J=8.1 Hz, 1H), 6.86 (dd, J=8.1, 2.7 Hz, 1H), 4.17(s, 3H), 4.13(q, J=7.1 Hz, 2H), 3.89(s, 3H), 1.01(t, J=7.1 Hz, 3H) |
| 36 | 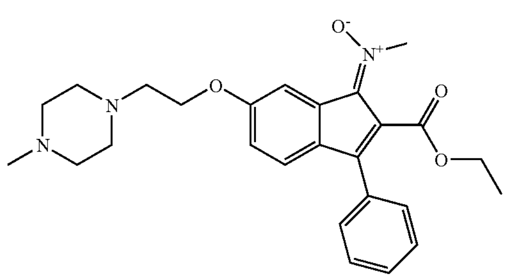 | 8.28(d, J=2.4 Hz, 1H), 7.44(s, 5H), 7.15(d, J=8.2 Hz, 1H), 6.86(dd, J=8.4, 2.4 Hz, 1H), 4.29-4.08(m, 7H), 2.86(t, J=5.7 Hz, 2H), 2.80-2.55(m, 8H), 2.34(s, 3H), 1.05(t, J=7.2 Hz, 3H) |

TABLE 1-continued

| No. | structure | ¹H-NMR(CDCl₃, 300 M Hz) δ |
|---|---|---|
| 37 | 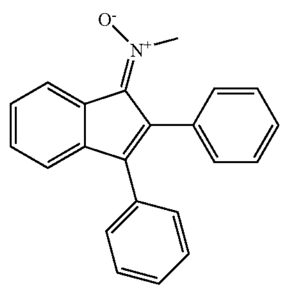 | 8.30(m, 1H), 7.36-7.26(m, 14H), 3.59(s, 3H) |
| 38 | 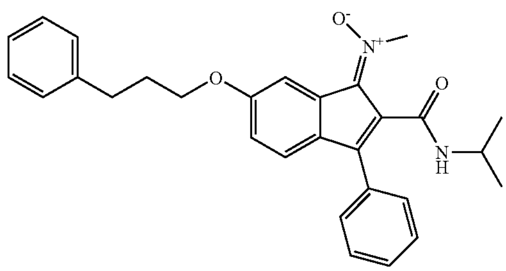 | 7.68-6.85(m, 13H), 5.40(d, J=7.8 Hz, 1H), 4.19(s, 3H), 4.03(t, J=6.3 Hz, 2H), 2.82(t, J=7.1 Hz, 2H), 2.12(quint, J=6.5 Hz, 2H), 0.90(d, J=6.5 Hz, 6H) |
| 39 | 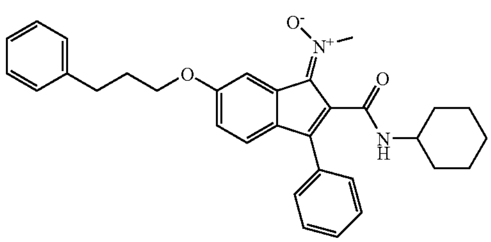 | 7.75-6.79(m, 13H), 5.51(d, J=7.8 Hz, 1H), 4.19(s, 3H), 4.04(t, J=6.3 Hz, 2H), 3.77-3.73(m, 1H), 2.82(t, J=7.1 Hz, 2H), 2.13(quint, J=6.5 Hz, 2H), 1.34-1.21(m, 10H) |
| 40 | 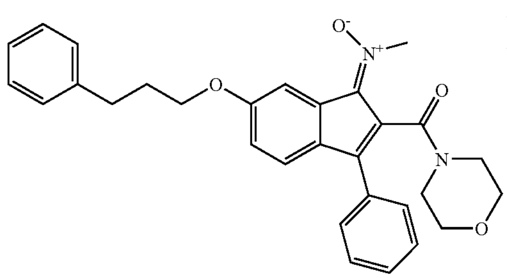 | 7.82-6.87(m, 13H), 4.11(s, 3H), 4.06(t, J=6.3 Hz, 2H), 3.66 3.26(m, 8H), 2.85(t, J=7.1 Hz, 2H), 2.16(quint, J=6.5 Hz, 2H) |
| 41 | 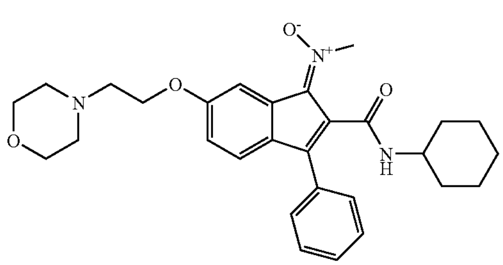 | 7.89-6.80(m, 8H), 4.21(s, 3H), 4.16(t, J5.4 Hz, 2H), 3.86(m, 1H), 3.75 (t, J=4.8 Hz, 4H), 2.83(t, J=5.4 Hz, 2H), 2.60(t, J=4.8 Hz, 4H), 1.63-1.18(m, 10H) |

TABLE 1-continued

| No. | structure | ¹H-NMR(CDCl₃, 300 M Hz) δ |
|---|---|---|
| 42 | 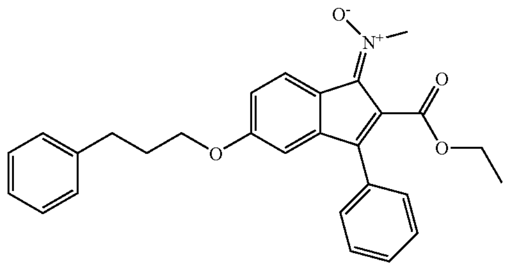 | 8.51(d, J=8.4 Hz, 1H), 7.45(s, 5H), 7.29-7.14(m, 5H), 6.88-6.80(m, 2H), 4.27-4.11(m, 5H), 3.96(t, J=6.3 Hz, 2H), 2.78(t, J=6.3 Hz, 2H), 2.10(m, 2H), 1.06(t, J=7.1 Hz, 3H) |
| 43 | 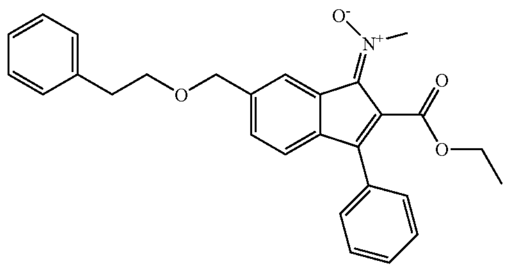 | 8.57(s, 1H), 7.45-7.15(m, 12H), 4.60(s, 2H), 4.17-4.13(m, 5H), 3.75-3.63(m, 2H), 2.99-2.84(m, 2H), 1.25-1.10(m, 3H) |
| 44 | 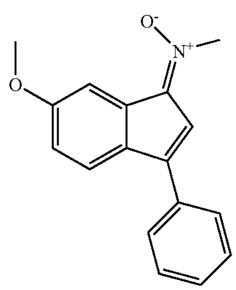 | 8.22(d, J=2.5 Hz, 1H), 7.63 7.60(m, 2H), 7.47 7.39(m, 4H), 6.85(dd, J=8.3, 2.5 Hz, 1H), 6.39(s, 1H), 4.07(s, 3H), 3.86(s, 3H) |
| 45 | 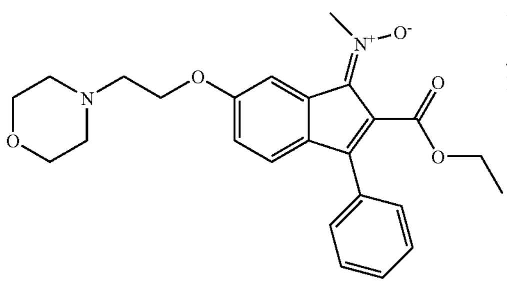 | 7.56-7.53(m, 2H), 7.44-7.41(m, 3H), 7.31(d, J=8.6 Hz, 1H), 7.12(d, J=1.9 Hz, 1H), 6.78(dd, J=8.2, 2.2 Hz, 1H), 4.31 -4.11(m, 7H), 3.75(t, J=4.5 Hz, 4H), 2.83(t, J=5.6 Hz, 2H), 2.59(t, J=4.5 Hz, 4H), 1.24(t, J=7.1 Hz, 3H), mp 151-152° C. |
| 46 | 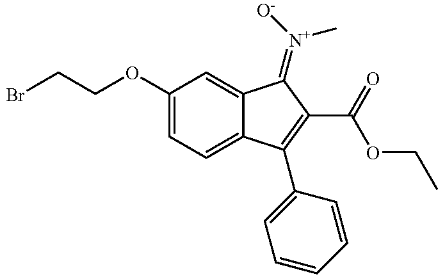 | 8.27(d, J=2.6 Hz, 1H), 7.44(s, 5H), 7.17(d, J=8.6 Hz, 1H), 6.89(dd, J=8.2, 2.4 Hz, 1H), 4.38(t, J=6.2 Hz, 2H), 419-4.08(m, 5H), 3.66(t, J=6.2 Hz, 2H), 1.05(t, J=7.2 Hz, 3H) |

TABLE 1-continued

| No. | structure | $^1$H-NMR(CDCl$_3$, 300 M Hz) δ |
|---|---|---|
| 47 | 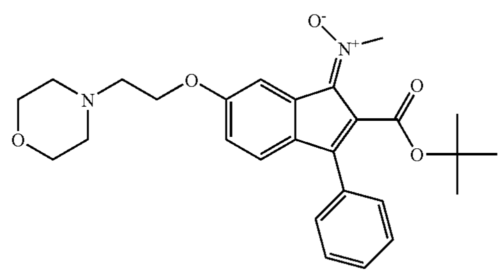 | 8.26(d, J=2.4 Hz, 1H), 7.33-7.30(m, 2H), 7.29-7.27(m, 4H), 6.84(dd, J= 8.3, 2.4 Hz, 1H), 4.19(t, J=5.5 Hz, 2H), 3.74(t, J=4.7 Hz, 4H), 1.39(s, 9H) |
| 48 | 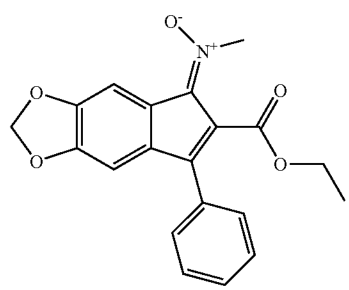 | 8.18(s, 1H), 7.43(s, 5H), 6.72(s, 1H), 6.02(s, 2H), 4.14(q, J=7.0 Hz, 2H), 4.12(s,3H), 1.04(t, J=7.0 Hz, 3H),mp 119-121° C. |
| 49 | 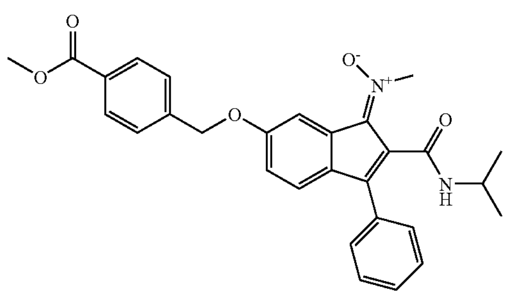 | 8.26(s, 1H), 8.06-8.00(m, 2H), 7.52-7.14(m, 9H), 5.17(s, 2H), 4.18(s, 3H), 4.12-4.00(m, 1H), 3.90(s, 3H), 0.92(d, J=6.5 Hz, 6H) |
| 50 | 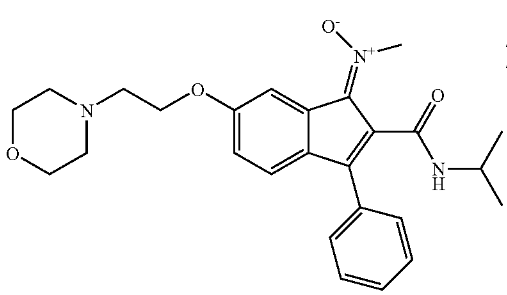 | 8.26(s, 1H), 7.46-7.41(m, 5H), 7.19-7.15(m, 1H), 6.87-6.81(m, 1H), 4.18-4.04(m, 6H), 3.76-3.71(m, 4H), 2.85-2.80(m, 2H), 2.62-2.57(m, 4H), 0.91(s, 3H), 0.88(s, 3H), mp 123-125° C. |
| 51 | 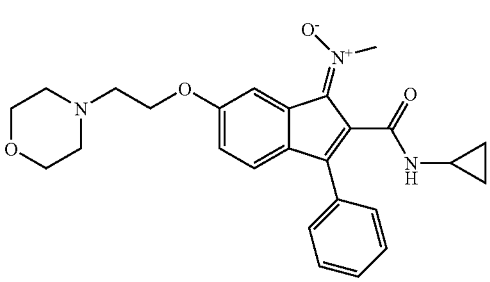 | 8.27(d, J=2.2 Hz, 1H), 7.50-7.40(m, 5H), 7.18(d, J=8.2 Hz, 1H), 6.86(dd, J=8.2, 2.2 Hz, 1H), 5.60(brs, 1H), 4.19(s, 4H), 4.18(t, J=5.6 Hz, 2H), 3.73(t, J=4.8 Hz, 4H), 2.81(t, J=5.6 Hz, 2H), 2.73-2.65(m, 1H), 2.58(t, J=4.8 Hz, 4H), 0.75-0.50(m, 4H) |

TABLE 1-continued

| No. | structure | ¹H-NMR(CDCl₃, 300 M Hz) δ |
|---|---|---|
| 52 | 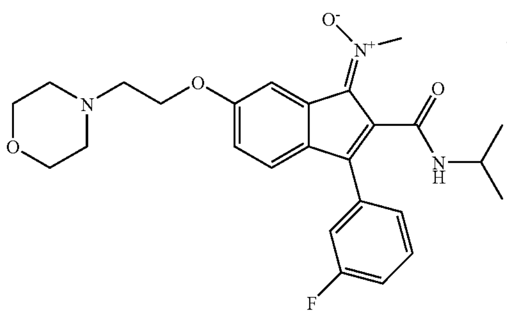 | 8.27(s, 1H), 7.46-6.81(m, 7H), 5.42(m, 1H), 4.19(t, J=5.4 Hz, 2H), 3.74(t, J=4.8 Hz, 4H), 2.83(t, J=5.4 Hz, 2H), 2.59(t, J=4.8 Hz, 4H), 0.97(s, 3H), 0.94 (s, 3H) |
| 53 | 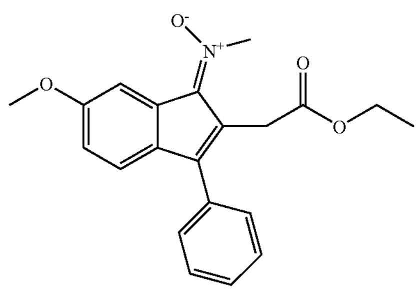 | 8.66-7.00(m, 8H), 4.17(s, 3H), 4.15(q, J=7.2 Hz, 2H), 3.89(s, 3H), 3.70(s, 2H), 1.26(t, J=7.2 Hz, 3H) |
| 54 | 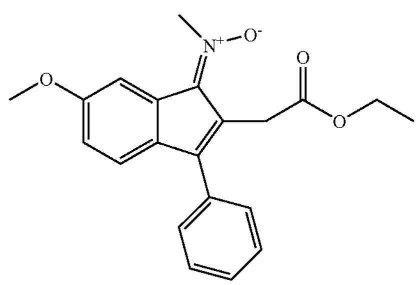 | 7.56-6.98(m, 8H), 4.31(s, 3H), 4.22(q, J=7.2 Hz, 2H), 3.87(s, 3H), 3.68(s, 2H), 1.28(t, J=7.2 Hz, 3H) |
| 55 | 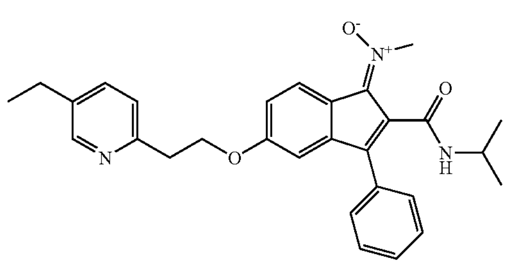 | 8.47(d, J=8.0 Hz, 1H), 8.37(d, J=2.0 Hz, 1H), 7.50-7.43(m, 6H), 7.15(d, J=8.1 Hz, 1H), 6.86-6.81(m, 2H), 5.43(brd, 1H), 4.35(t, J=6.6 Hz, 2H), 4.15(s, 3H), 4.02(m, 1H), 3.20(t, J=6.6 Hz, 2H), 2.60(q, J=7.4 Hz, 2H), 1.24(t, J=7.4 Hz, 3H), 0.90(d, J=6.7 Hz, 6H) |
| 56 | 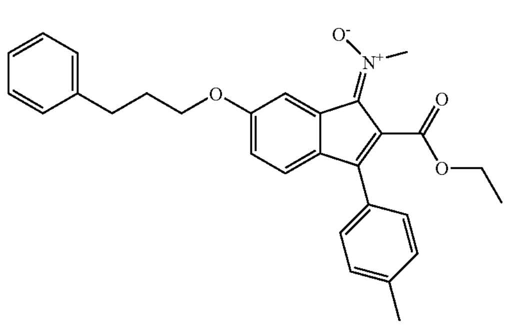 | 8.27(s, 1H), 7.36-7.16(m, 10H), 6.85(dd, J=8.0, 2.4 Hz, 1H), 4.15(q, J=7.1 Hz, 2H), 4.11(s, 3H), 4.05(t, J=6.2 Hz, 2H), 2.82(t, J=7.8 Hz, 2H), 2.42(s, 3H), 2.05-2.15(m, 2H), 1.10(t, J=7.1 Hz, 3H) |

TABLE 1-continued

| No. | structure | ¹H-NMR(CDCl₃, 300 M Hz) δ |
|---|---|---|
| 57 | 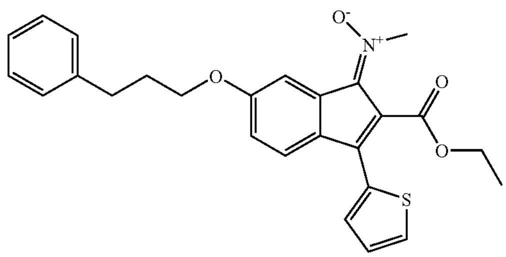 | 8.26(d, J=2.4 Hz, 1H), 7.52-7.49(m, 2H), 7.41(d, J=2.4 Hz, 1H), 7.30-7.15 (m, 6H), 6.89(dd, J=8.4, 2.4 Hz, 1H), 4.28(q, J=7.2 Hz, 2H), 4.09(s, 3H), 4.05(t, J=6.0 Hz, 2H), 2.82(t, J=7.2 Hz, 2H), 2.15-2.11(m, 2H), 1.26(t, J= 7.2, 3H) |
| 58 | 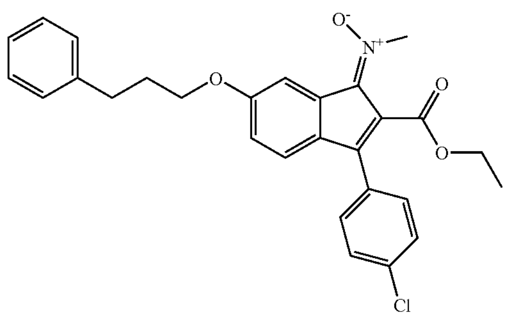 | 8.26(s, 1H), 7.44-7.09(m, 10H), 6.82(dd, J=8.0, 2.4 Hz, 1H), 4.13(q, J=7.4 Hz, 2H), 4.12(s, 3H), 4.04(t, J=6.2 Hz, 2H), 2.82(t, J=7.4 Hz, 2H), 2.15-2.12(m, 2H), 1.10(t, J=7.2 Hz, 3H) |
| 59 | 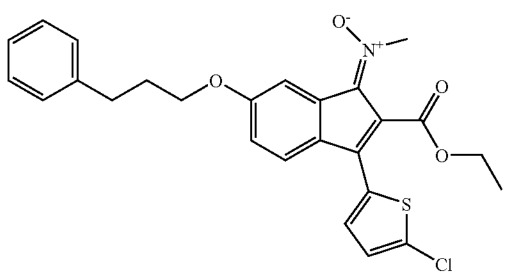 | 8.25(d, J=2.4 Hz, 1H), 7.47(d, J=8.4 Hz, 1H), 6.97(d, J=4.0 Hz, 1H), 6.90 (dd, J=8.4, 2.8 Hz, 1H), 4.31(q, J=7.2 Hz, 1H, 2H), 4.08-4.03(m, 5H), 2.82 (t, J=7.2 Hz, 2H), 2.15-2.11(m, 2H), 1.30(t, J=7.2 Hz, 3H) |
| 60 | 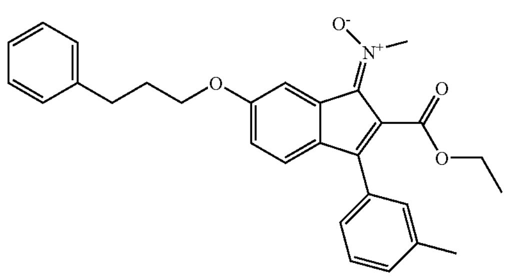 | 8.26(d, J=2.8 Hz, 1H), 7.35-7.15(m, 8H), 7.03(d, J=7.6 Hz, 1H), 6.92(d, J= 8.8 Hz, 1H), 6.84(dd, J=8.4, 2.8 Hz, 1H), 4.16-4.01(m, 7H), 2.82(t, J=8.0 Hz, 2H), 2.40(s, 3H), 2.15-2.11(m, 2H), 1.06(t,J=7.6 Hz, 3H) |
| 61 | 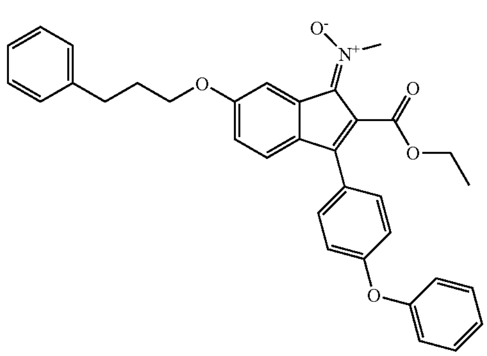 | 8.27(d, J=2.4 Hz, 1H), 7.71-7.70(m, 1H), 7.54-7.52(m, 1H), 7.44-6.84(m, 14H), 7.30-4.01(m, 7H), 2.82(t, J=7.6 Hz, 2H), 2.16-2.09(m, 2H), 1.43(t, J= 6.8 Hz, 3H) |

| No. | structure | $^1$H-NMR(CDCl$_3$, 300 M Hz) δ |
|---|---|---|
| 62 | 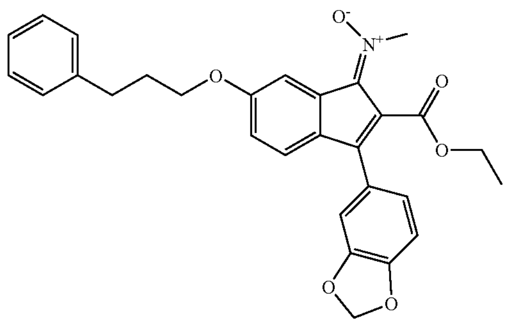 | 8.26(s, 1H), 7.32-7.15(m, 6H), 7.00-6.83(m, 4H), 6.02(s, 2H), 4.21(q, J=7.2 Hz, 2H), 4.09(s, 3H), 4.03(t, 2H), 2.82(t, J=7.2 Hz, 2H), 2.12(m, 2H), 1.16(t, J=7.2 Hz, 3H) |
| 63 | 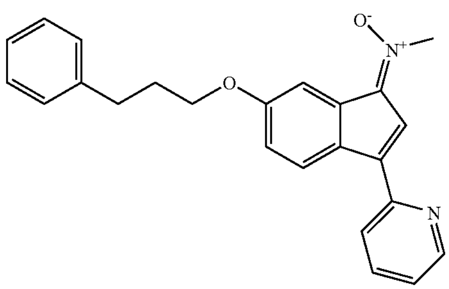 | 8.74-8.72(m, 1H), 8.20(d, J=2.8 Hz, 1H), 7.97(d, J=8.4 Hz, 1H), 7.77-7.76 (m, 2H), 7.31-7.26(m, 3H), 7.23-7.17(m, 3H), 6.90(dd, J=8.4, 2.4 Hz, 1H), 6.86(s, 1H), 4.14(s, 3H), 4.06(t, J=6.4 Hz, 2H), 2.83(t, J=8.0 Hz, 2H), 2.10-2.17(m, 2H) |
| 64 | 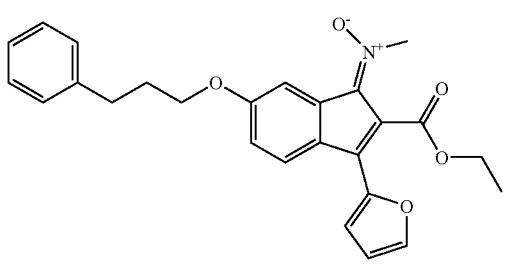 | 8.28(d, J=2.8 Hz, 1H), 7.74(d, J=8.4 Hz, 1H), 7.59(d, J=1.6 Hz, 1H), 0.29-7.19(m, 5H), 7.00(d, J=4.0 Hz, 1H), 6.92(dd, J=8.4, 2.4 Hz, 1H), 6.69-6.57(m, 1H), 4.40(q, J=7.2 Hz, 2H), 4.08(s, 3H), 4.05(t, J=6.4 Hz, 2H), 2.83(t, J=7.6 Hz, 2H), 2.16-2.13(m, 2H), 1.37(t, J=7.2 Hz, 3H) |
| 65 | 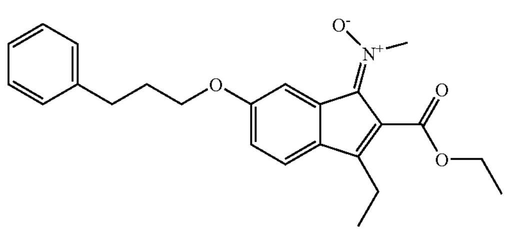 | 8.22(d, J=2.4 Hz, 1H), 7.30-7.17(m, 6H), 6.89(dd, J=8.4, 2.8 Hz, 1H), 4.37 (q, J=7.2 Hz, 2H), 4.10-4.00(m, 5H), 2.81(t, J=7.2 Hz, 2H), 2.74(t, J=7.2 Hz, 2H), 2.15-2.09(m, 2H), 1.40(t, J=7.2 Hz, 3H) 1.24(t, J=7.2 Hz, 3H) |
| 66 | 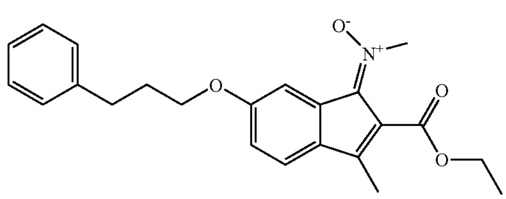 | 8.20(d, J=2.4 Hz, 1H), 7.30-7.17(m, 6H), 6.89(dd, J=8.0, 2.4 Hz, 1H), 3.97 (q, J=7.2 Hz, 2H), 4.06-4.03(m, 5H), 2.82(t, J=7.2 Hz, 2H), 2.33(s, 3H), 2.12-2.10(m, 2H), 1.40(t, J=7.2 Hz, 3H) |
| 67 | 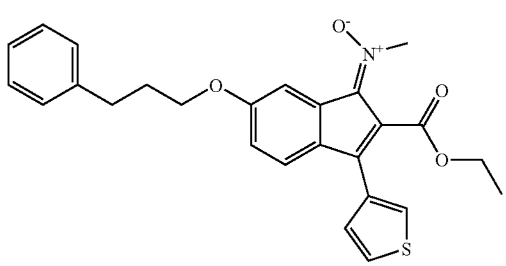 | 8.26(d, J=2.4 Hz, 1H), 7.58(dd, J=2.4, 1.6 Hz, 1H), 7.42(m, 1H), 7.30-7.26 (m, 4H), 7.23-7.19(m, 3H), 6.87(d, J=2.8 Hz, 1H), 4.22(q, J=7.2 Hz, 2H), 4.07(s, 3H), 4.05(t, J=6.4 Hz, 2H), 2.82(t, J=7.6 Hz, 2H), 2.15-2.13(m, 2H), 1.20(t, J=7.2 Hz, 3H) |

TABLE 1-continued

| No. | structure | $^1$H-NMR(CDCl$_3$, 300 M Hz) δ |
|---|---|---|
| 68 | 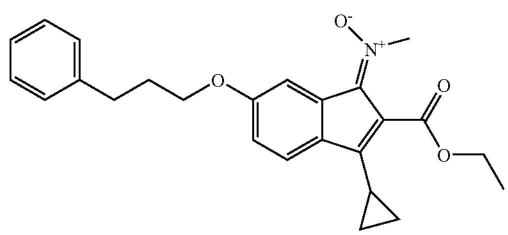 | 8.22(d, J=2.4 Hz, 1H), 7.31-7.17(m, 6H), 6.83(dd, J=8.4, 2.4 Hz, 1H), 4.38 (q, J=7.2 Hz, 2H), 4.02(t, J=6.4 Hz, 2H), 4.00(s, 3H), 2.81(t, J=7.8 Hz, 2H), 2.14-2.05(m, 2H), 1.40(t, J=7.2 Hz, 3H), 1.08-1.03(m, 4H) |
| 69 | 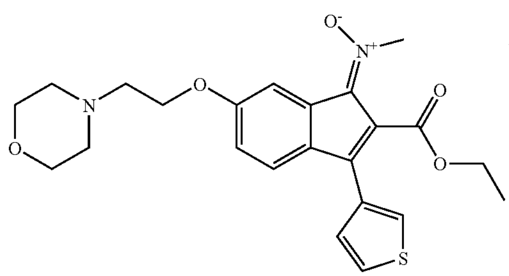 | 8.27(d, J=2.0 Hz, 1H), 7.58-7.57(m, 1H), 7.43-7.41(m, 1H), 7.31-7.27(m, 2H), 6.89(dd, J=8.2, 2.0 Hz, 1H), 4.26-4.19(m, 4H), 4.10(s, 3H), 3.76-3.74 (m, 4H), 2.84(t, J=5.2 Hz, 2H), 2.61-2.59(m, 4H), 1.20(t, J=7.6 Hz, 3H) |
| 70 | 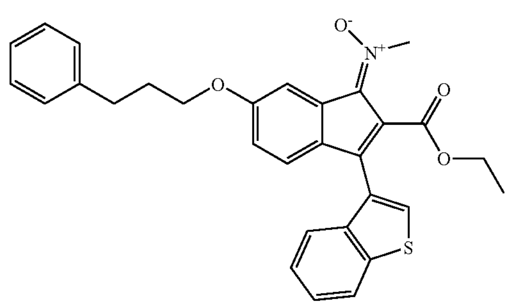 | 8.29(d, J=2.4 Hz, 1H), 7.90(d, J=8.0 Hz, 1H), 7.62(d, J=8.0 Hz, 1H), 7.54 (s, 1H), 7.40-7.30(m, 2H), 7.28-7.24(m, 2H), 7.22-7.18(m, 3H), 7.05(d, J= 8.4 Hz, 1H), 6.82-6.78(m, 1H), 4.17(s, 3H), 4.07-3.97(m, 4H), 2.82(t, J=7.2 Hz, 2H), 2.12(t, J=7.2 Hz, 2H), 0.78(t, J=7.2 Hz, 3H) |
| 71 | 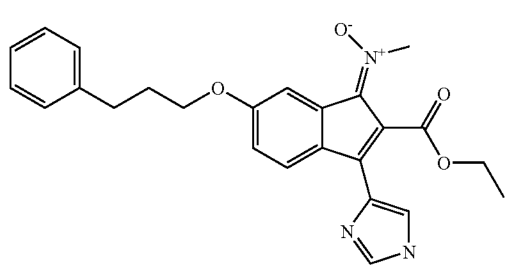 | 8.26(d, J=2.4 Hz, 1H), 7.93(d, J=8.4 Hz, 1H), 7.54(d, J=4.0 Hz, 2H), 7.29-7.26(m, 2H), 7.22-7.16(m, 3H), 6.90(dd, J=8.4, 2.4 Hz, 1H), 4.34(q, J= 7.2 Hz, 2H), 4.05(s, 3H), 3.77-3.75(m, 2H), 2.82(t, J=7.2 Hz, 2H), 2.14-2.10(m, 2H), 1.36(t, J=7.2 Hz, 3H) |
| 72 | 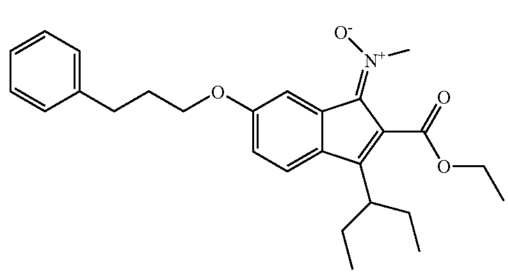 | 8.26(d, J=2.4 Hz, 1H), 7.40(d, J=8.4 Hz, 1H), 7.31-7.18(m, 5H), 6.83(d, J= 8.4, 2.8 Hz, 1H), 4.36(q, J=7.2 Hz, 2H), 4.03(t, J=6.2 Hz, 2H), 4.00(s, 3H), 2.81(t, J=7.8 Hz, 2H), 2.76-2.68(m, 1H), 2.15-2.08(m, 2H), 1.85-1.72 (m, 4H), 1.38(t, J=7.0 Hz, 3H), 0.85(t, J=7.4 Hz, 6H) |

TABLE 1-continued

| No. | structure | $^1$H-NMR(CDCl$_3$, 300 M Hz) δ |
|---|---|---|
| 73 | 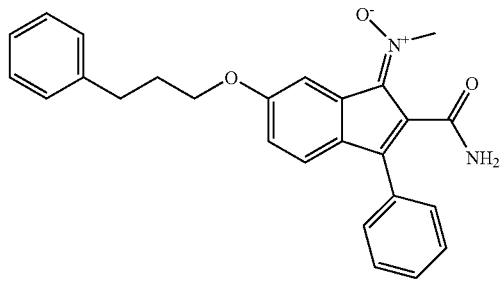 | 8.28-6.82(m, 13H), 5.57(brs, 2H), 4.23(s, 3H), 4.05(t, J=6.0 Hz, 2H), 2.83(t, J=7.2, 2H), 2.16-2.05(m, 2H) |
| 74 | 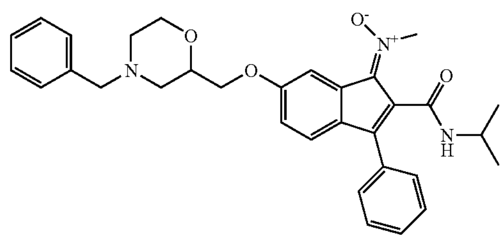 | 8.25(s, 1H), 7.49-6.84(m, 12H), 5.39(d, J=8.5 Hz, 1H), 4.19(s, 3H), 4.01 (m, 1H), 3.96(d, J=5.3 Hz, 2H), 3.92(d, J=6.5 Hz, 2H), 3.75(t, J=8.9 Hz, 2H), 3.55(s, 2H), 2.84(t, J=8.9 Hz, 2H), 0.92(s, 3H), 0.88(s, 3H) |
| 75 | 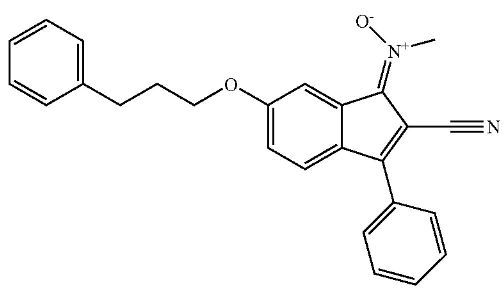 | 8.29(d, J=2.3 Hz, 1H), 7.72-7.55(m, 5H), 7.44(d, J=8.3 Hz, 1H), 7.31-7.17(m, 5H), 6.96(dd, J=8.3, 2.3 Hz, 1H), 4.47(s, 3H), 4.08(t, J=6.2 Hz, 2H), 2.83(t, J=6.2 Hz, 2H), 2.12(m, 2H), mp 126-128° C. |
| 76 | 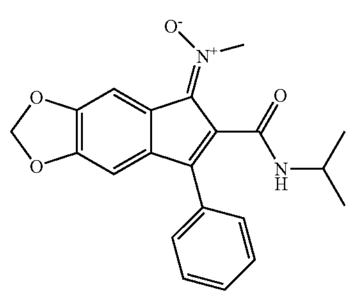 | 8.08(s, 1H), 7.45(s, 5H), 6.71(s, 1H), 5.97(s, 2H), 5.65(brs, 1H), 4.15(s, 3H), 4.13-3.96(m, 1H), 0.92(d, J=7.6 Hz, 6H) |
| 77 | 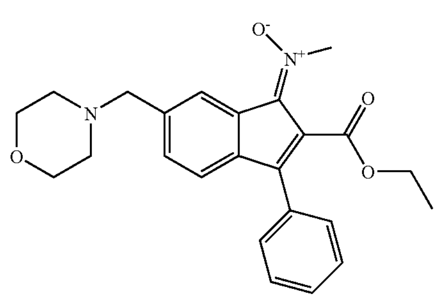 | 8.55(s, 1H), 7.45(s, 5H), 7.44-7.15(m, 3H), 4.17(q, J=7.1 Hz, 2H), 4.13 (s, 3H), 3.70(t, J=4.8 Hz, 4H), 3.57(s, 2H), 2.46(t, J=4.8 Hz, 4H), 1.07(t, J=7.1 Hz, 3H) |

TABLE 1-continued

| No. | structure | $^1$H-NMR(CDCl$_3$, 300 M Hz) δ |
|---|---|---|
| 78 | 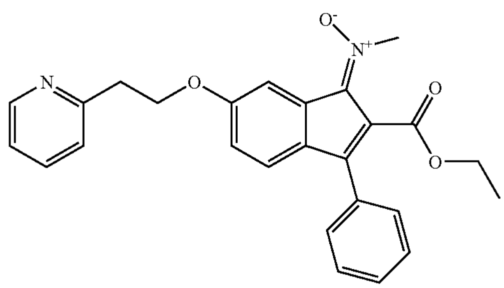 | 8.55(d, J=4.4 Hz, 1H), 8.28(d, 2.3 Hz, 1H), 7.53-7.43(m, 4H), 7.34-7.26 (m, 2H), 7.17-7.12(m, 2H), 6.84(dd, J=8.3 Hz, J=2.3 Hz, 1H), 4.44(t, J=6.6 Hz, 2H), 4.15-4.08(m, 5H), 3.29(t, J=6.6 Hz, 2H), 1.02(t, J=7.1 Hz, 3H) |
| 79 | 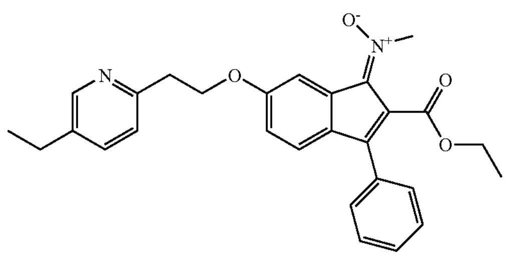 | 8.39(d, J=3.3 Hz, 1H), 8.27(d, J=2.4 Hz, 1H), 7.43(s, 5H), 7.26(m, 1H), 7.21-7.11(m, 2H), 6.86(d, J=2.4 Hz, 1H), 4.43(t, J=6.5 Hz, 2H), 4.39-4.07 (m, 5H), 3.25(t, J=6.5 Hz, 2H), 2.62(q, J=7.3 Hz, 2H), 1.04(t, J=6.1 Hz, 3H) |
| 80 | 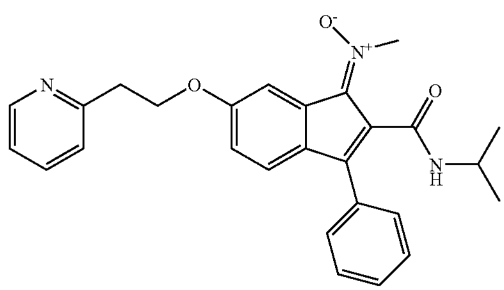 | 8.55(m, 1H), 8.26(d, J=2.6 Hz, 1H), 7.63(m, 1H), 7.49-7.43(m, 4H), 7.27 (m, 2H), 7.15(m, 2H), 6.83(dd, J=8.3 Hz, J=2.6 Hz, 1H), 4.43(t, J=6.7 Hz, 2H), 4.18(s, 3H), 3.28(t, J=6.5 Hz, 2H), 0.90(d, J=5.3 Hz, 6H), mp 124-126° C. |
| 81 | 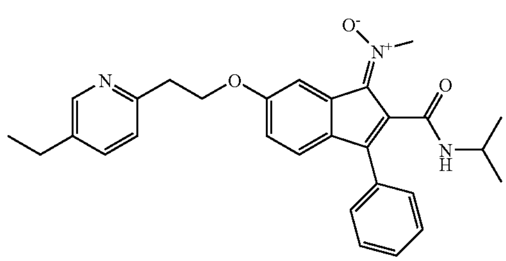 | 8.39(s, 1H), 8.25(d, J=1.8 Hz, 1H), 7.47-7.45(m, 7H), 7.21-7.14(m, 2H), 6.82(dd, J=8.2 Hz, J=2.0 Hz, 1H), 4.39(t, J=6.6 Hz, 2H), 4.17(s, 3H), 4.06(m, 1H), 3.25(t, J=6.2S Hz, 2H), 2.63(q, J=7.4 Hz, 2H), 0.90(d, J=6.5 Hz, 3H) |
| 82 | 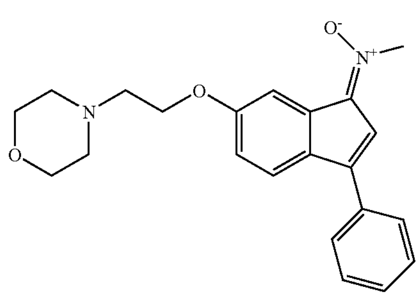 | 8.22(d, J=2.4 Hz, 1H), 7.64-7.35(m, 6H), 6.88(dd, J=8.3, 2.4 Hz, 1H), 6.42(s, 1H), 4.18(t, J=6.4 Hz, 2 H), 4.10(s, 3 H), 3.74(t, J=4.5 Hz, 4H), 2.83(t, J=5.6 Hz, 2H), 2.59(t, J=4.5 Hz, 4H), mp 122-123° C. |

TABLE 1-continued

| No. | structure | $^1$H-NMR(CDCl$_3$, 300 M Hz) δ |
|---|---|---|
| 83 | 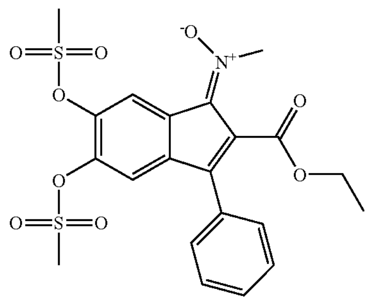 | 8.13(s, 1H), 7.57-7.30(m, 5H), 6.85(s, 1H), 4.21(q, J=7.2 Hz, 2H), 3.92(s, 3H), 3.36(s, 3H), 3.30(s, 3H), 1.15(t, J=7.2 Hz, 3H) |
| 84 | 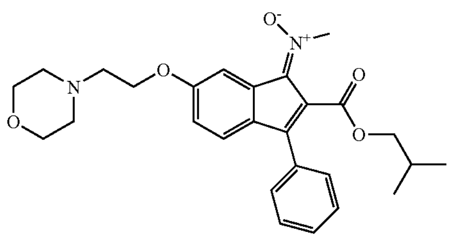 | 8.26(d, J=2.6 Hz, 1H), 7.26-7.23(m, 5H), 7.15(d, J=8.2 Hz, 1H), 6.86(dd, J=8.2, 2.6 Hz, 1H), 4.18(t, J=5.2 Hz), 4.11(s, 3H), 3.82(d, J=6.6 Hz, 2H), 3.72(t, J=4.6 Hz, 4H), 2.84(t, J=5.2 Hz, 2H), 2.57(t, J=4.6 Hz, 4H), 1.65 (sept, J=6.6 Hz), 0.68(d, J=6.6 Hz, 6H) |
| 85 | 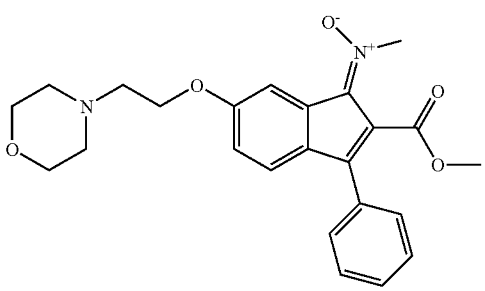 | 8.28-6.85(m, 8H), 4.28-4.10(m, 2H), 4.10(s, 3H), 3.73(t, J=4.8 Hz, 4H), 3.66(s, 3H), 2.82(t, J=5.4 Hz, 2H), 2.58(t, J=4.8 Hz, 4H) |
| 86 | 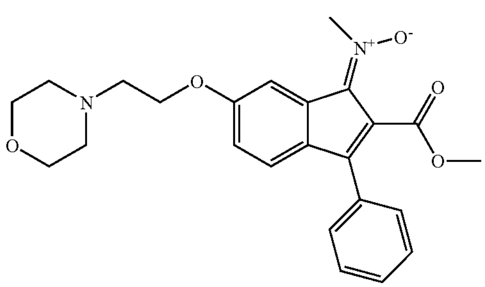 | 7.53-6.76(m, 8H), 4.24-4.10(m, 2H), 4.24(s, 3H), 3.79(s, 3H), 3.75(t, J=4.8 Hz, 4H), 2.83(t, J=5.4 Hz, 2H), 2.59(t, J=4.8 Hz, 4H) |
| 87 | 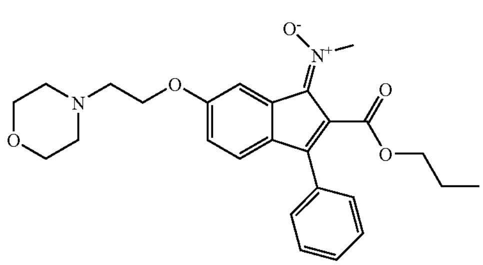 | 8.28-6.82(m, 8H), 4.20(t, J=5.6 Hz, 2H), 4.12(s, 3H), 4.02(t, J=6.5 Hz, 2H), 3.74(t, J=4.8 Hz, 4H), 2.85(t, J=5.6 Hz, 2H), 2.61(t, J=4.8 Hz, 4H), 1.48-1.25(m, 2H), 0.87(t, J=5.4 Hz, 3H) |

TABLE 1-continued

| No. | structure | $^1$H-NMR(CDCl$_3$, 300 M Hz) δ |
|---|---|---|
| 88 | 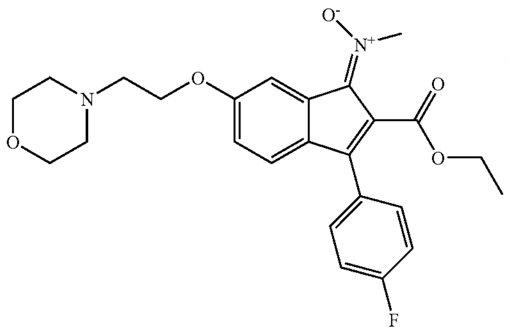 | 8.27(d, J=2.4 Hz, 1H), 7.45-7.42(m, 2H), 7.17-7.11(m, 3H), 6.87(dd, J= 8.0, 2.4 Hz, 1H), 4.23-4.12(m, 7H), 3.77-3.75(m, 4H), 2.86(t, J=5.6 Hz, 2H), 2.65-2.60(m, 4H), 1.10(t, J=7.2 Hz, 3H) |
| 89 | 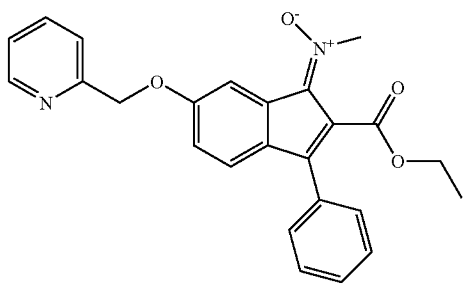 | 8.61(d, J=4.8 Hz, 1H), 8.39(d, J=2.4 Hz, 1H), 7.73(t, J=7.6 Hz, 1H), 7.55 (d J=7.6, 1H), 7.55(d, J=7.6, 1H), 7.48-7.21(m, 6H), 7.17(d, J=8.4 Hz, 1H), 6.94(dd, J=2.4, 1H), 5.28(s, 2H), 4.12(s, 3H) 4.12(q, J=6.8 Hz, 2H), 1.04(t, J=6.8 Hz, 3H) |
| 90 | 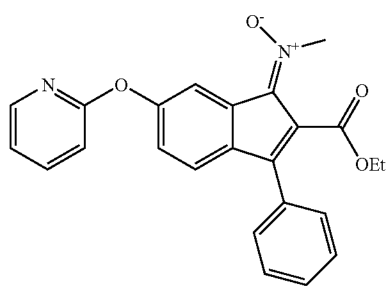 | 8.41(s, J=2.4 Hz, 1H), 8.19(dd, J=2.0 Hz, 1H), 7.69(t, 1H), 7.15(s, 5H), 7.28(d, J=8.4 Hz, 1H), 7.13(dd, J=2.0 Hz, 1H), 7.01-6.95(m, 2H), 4.13(q, J=7.2 Hz, 2H), 4.11(s, 3H), 1.05(t, J=7.2 Hz, 3H) |
| 91 | 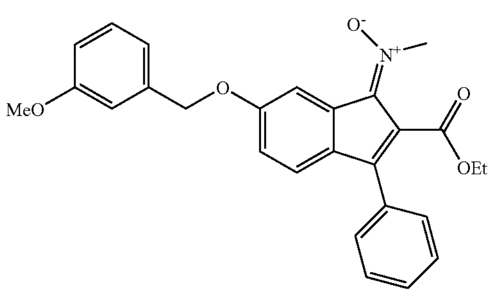 | 8.38(s, 1H), 7.44(s, 5H) 7.28(t, J=8.0 Hz, 1H), 7.05-6.91(m, 4H), 5.13(s, 2H), 4.12(s, 3H), 4.13(q, J=7.2 Hz, 2H), 1.04(t, J=7.2 Hz, 3H) |
| 92 | 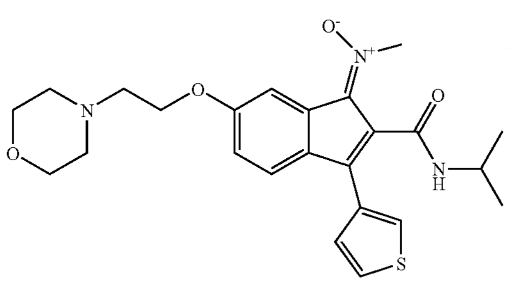 | 8.23(d, J=2.4 Hz, 1H), 7.59-7.58(m, 1H), 7.44-7.43(m, 1H), 7.31-7.27(m, 2H), 6.86(dd, J=7.6, 2.4 Hz, 1H), 5.68(d, J=8.0 Hz, 1H), 4.18-4.10(m, 6H), 3.75-3.72(m, 4H), 2.81(t, J=5.6 Hz, 2H), 2.60-2.57(m, 4H), 1.03(d, J= 6.4 Hz, 6H) |

TABLE 1-continued

| No. | structure | ¹H-NMR(CDCl₃, 300 M Hz) δ |
|---|---|---|
| 93 | 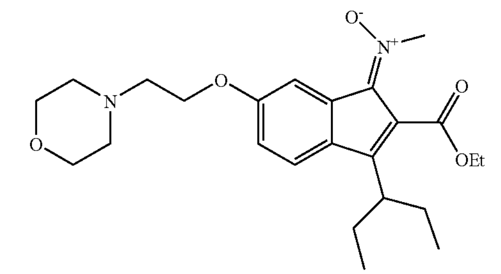 | 8.27(d, J=2.4 Hz, 1H), 7.41(d, J=8.0 Hz, 1H), 6.85(dd, J=8.4, 2.8 Hz, 1H), 4.36(q, J=7.2 Hz, 2H), 4.18(t, J=5.8 Hz, 2H), 4.00(s, 3H), 3.74(t, J= 4.6 Hz, 4H), 2.82(t, J=5.6 Hz, 2H), 2.73-2.68(m, 1H), 2.58(t, J=4.6 Hz, 4H), 1.82-1.75(m, 4H), 1.39(t, J=7.2 Hz, 3H), 0.85(t, J=7.2 Hz, 6H) |
| 94 | 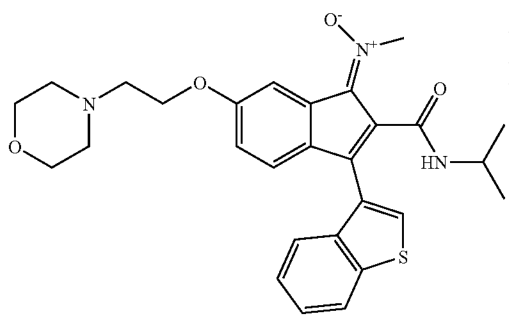 | 8.28(s, J=2.4 Hz, 1H), 7.92(d, J=6.4 Hz, 1H), 7.70(d, .1 6.4 Hz, 1H), 7.43-7.35(m, 2H), 7.04(d, J=8.8 Hz, 1H), 6.81(dd, J=2.4 Hz, 1H) 4.21(s, 3H), 4.17(t, J=5.6 Hz, 2H), 3.85(m, 1H), 3.73(t, J=4.4 Hz, 4H), 2.82(t, J= 5.6 Hz, 2H), 2.58(t, J=4.4 Hz, 4H), 0.74(d, 3H), 0.59(d, 3H), mp 77-79° C. |
| 95 | 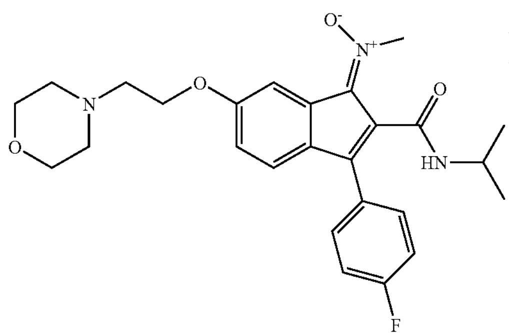 | 8.24(d, J=2.4 Hz, 1H), 7.51-7.48(m, 2H), 7.18-7.13(m, 3H), 6.84(dd, J= 7.6, 2.4 Hz, 1H), 5.53(d, J=8.0 Hz, 1H), 4.19-4.16(m, 5H), 4.12-4.01(m, 3.75-3.72(m, 4H), 2.81(t, J=5.6 Hz, 2H), 2.59-2.57(m, 4H), 0.95(d, J= 6.4 Hz, 6H) |
| 96 | 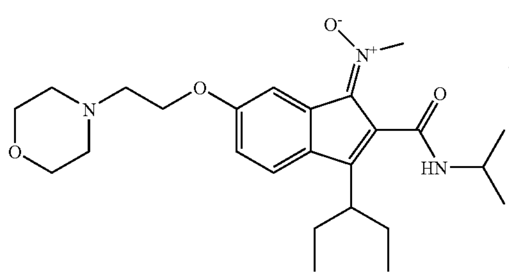 | 8.25(d, J=2.4 Hz, 1H), 7.33(d, J=8.4 Hz, 1H), 6.28(dd, J=8.4, 2.4 Hz, 1H), 4.27(m, 1H), 4.17(t, J=5.6 Hz, 2H), 4.08(s, 3H), 3.73(m, 4H), 2.81(t, J=5.6 Hz, 2H), 2.59-2.51(m, 5H), 1.80(m, 4H) 1.27(d, J=6.4 Hz, 6H), 0.88 (t, J=7.2 Hz, 6H) |
| 97 | 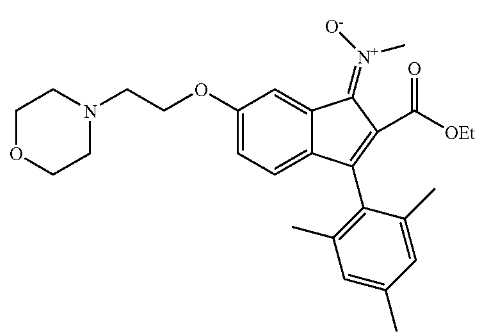 | 8.27(d, J=2.4 Hz, 1H), 6.89(s, 2H), 6.82-6.76(m, 2H), 4.15-4.09(m, 5H), 4.01(q, J=6.8 Hz, 2H), 3.74-3.72(m, 4H), 2.82(t, J=5.6 Hz, 2H), 2.59-2.57 (m, 4H), 2.32(s, 3H), 2.04(s, 6H), 1.26(t, J=6.8 Hz, 3H) |

TABLE 1-continued

| No. | structure | $^1$H-NMR(CDCl$_3$, 300 M Hz) δ |
|---|---|---|
| 98 | 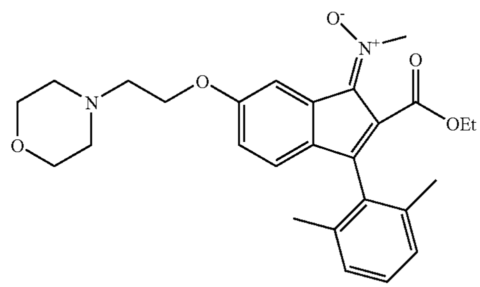 | 8.28(d, J=2.4 Hz, 1H), 7.20-7.16(m, 1H), 7.07(d, J=7.6 Hz, 2H), 6.83(dd, J=7.8, 2.4 Hz, 1H), 6.76(J=8.4 Hz, 1H), 4.21-4.17(m, 5H), 3.99(q, J=7.2 Hz, 2H), 3.74=3.72(m, 4H), 2.82(t, J=5.6 Hz, 2H), 2.60-2.57(m, 4H), 2.09(s, 6H), 0.81(t, J=7.2 Hz, 3H) |
| 99 | 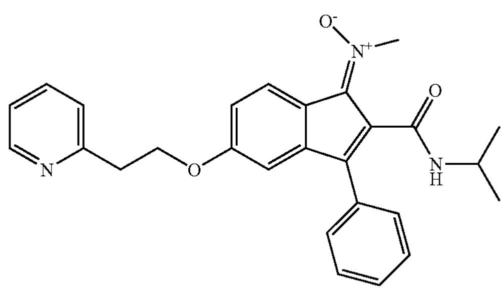 | 8.53(d, J=4.9 Hz, 1H), 8.48(d, J=8.3 Hz, 1H), 7.60(m, 1H), 7.48-7.43(m, 5H), 7.24-7.13(m, 2H), 6.87-6.81(m, 2H), 5.42(brs, 1H), 4.37(t, J=6.6 Hz, 2H), 4.15(s, 3H), 4.08(m, 1H), 3.24 (t, J=6.6 Hz, 2H), 0.90(d, J=6.7 Hz, 6H), mp 158-159° C. |
| 100 | 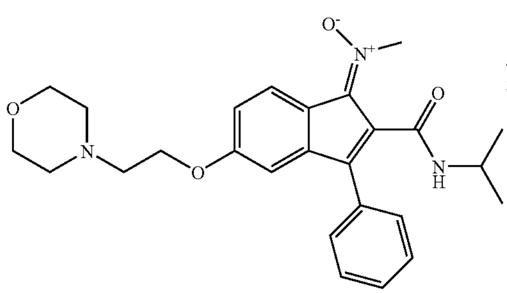 | 8.49(d, J=9.0 Hz, 1H), 7.48-7.44(m, 5H), 6.84-6.82(m, 2H), 5.47(brd, 1H), 4.15(s, 3H), 4.10(t, J=5.6 Hz, 2H), 4.05(m, 1H), 3.71(t, J=4.3 Hz, 4H), 2.77(t, J=5.6 Hz, 2H), 2.55(t, J=4.3 Hz, 4H), 0.90(d, J=6.5 Hz, 6H), mp 134-137° C. |
| 101 | 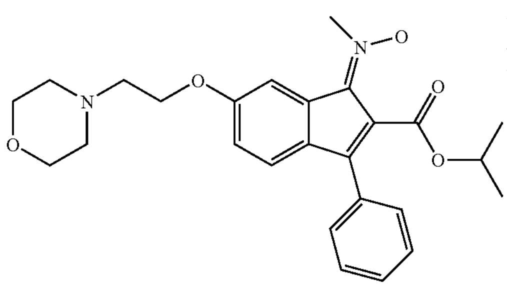 | 7.57-7.54(m, 2H), 7.43-7.41(m, 3H), 7.30(d, J=8.4 Hz, 1H), 7.12(d, J=1.8 Hz, 1H), 6.78(dd, J=8.4, 1.8 Hz, 1H), 5.17(quin, J=6.2 Hz, 1H), 4.25(s, 3H), 4.15(t, J=5.6 Hz, 2H), 3.76(t, J=4.4 Hz, 4H), 2.83(t, J=5.6 Hz, 2H), 2.59 (t, J=4.4 Hz, 4H), 1.23(d, J=6.2 Hz, 6H), mp 153-155° C. |
| 102 | 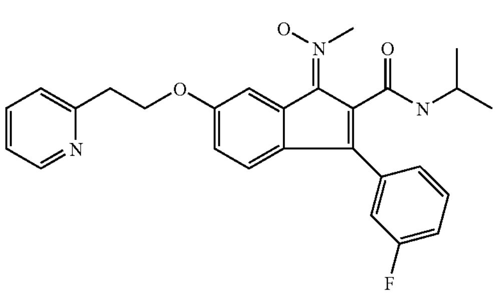 | 8.63(d, J=2 Hz, 1H), 8.25(d, J=2 Hz, 1H), 7.63(m, 1H), 7.40(m, 1H), 7.29(m, 2H), 7.15(m, 1H), 7.19(m, 3H), 6.87(m, 1H), 5.44(d, J=8.5 Hz, 1H), 4.46(t, J=6.6 Hz, 2H), 4.22(s, 3H), 4.09(m, 1H), 3.31(t, J=6.6 Hz, 2H), 0.97(d, J=6.6 Hz, 6H) |

TABLE 1-continued

| No. | structure | $^1$H-NMR(CDCl$_3$, 300 M Hz) δ |
|---|---|---|
| 103 | 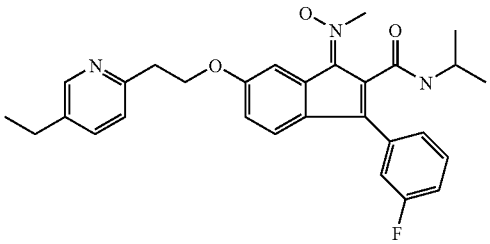 | 8.40(d, J=2 Hz, 1H), 8.28(d, J=2 Hz, 1H), 7.47(m, 2H), 7.3(m, 1H), 7.23(m, 2H), 7.19(m, 2H), 6.86(m, 1H), 5.3(d, J=7 Hz, 1H), 4.43(t, J=6.6 Hz, 2H), 4.2 (s, 3H), 4.05(m, 1H), 3.27(t, J=6.6 Hz, 2H), 2.64(q, J=7.6 Hz, 2H), 1.24(t, J=7.6 Hz, 3H), 0.97(d, J=6.7 Hz, 6H) |
| 104 | 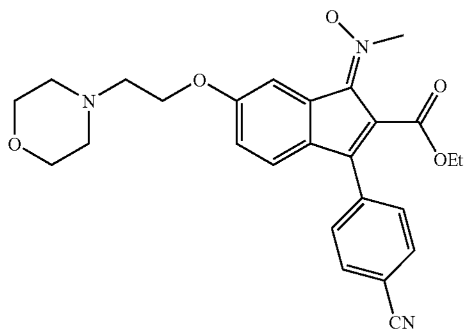 | 8.28(d, J=2.4 Hz, 1H), 7.91(d, J=8.0 Hz, 2H), 7.53(d, J=8.0 Hz, 2H), 7.10 (d, J=8.4 Hz, 1H), 6.88(dd, J=2.4, 6.0 Hz, 1H), 4.13-4.21(m, 7H), 3.74(t, J= 4.8 Hz, 4H), 2.83(t, J=5.6 Hz, 2H), 2.59(t, J=4.4 Hz, 4H), 1.07(t, J=7.2 Hz, 3H) |
| 105 | 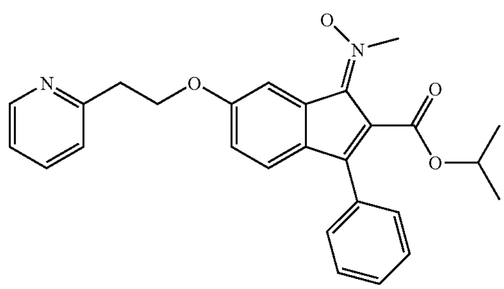 | 8.55(d, J=5.2 Hz, 1H), 8.26(d, J=2.4 Hz, 1H), 7.61-7.65(m, 1H), 7.42(s, 5H), 7.29(d, J=7.6 Hz, 1H), 7.14-7.17(m, 1H), 7.10(d, J=8.4 Hz, 1H), 6.82(dd, J=2.4, 8.4 Hz, 1H), 4.96-5.02(m, 1H), 4.43(t, J= 6.4 Hz, 2H), 4.12(s, 3H), 3.29(t, J=6.4 Hz, 2H), 1.04(d, J=6.4 Hz, 6H) |

1) 6-methoxy-1-(trans-methylimino-N-oxy)-3-phenyl-1H-indene-2-carboxylate ethyl ester
2) 1-(trans-isopropylimino-N-oxy)-6-methoxy-3-phenyl-1H-indene-2-carboxylate ethyl ester
3) 1-(trans-benzylimino-N-oxy)-6-methoxy-3-phenyl-1H-indene-2-carboxylate ethyl ester
4) 1-(trans-ethylimino-N-oxy)-6-methoxy-3-phenyl-1H-indene-2-carboxylate ethyl ester
5) 6-methoxy-1-(trans-phenylpropylimino-N-oxy)-3-phenyl-1H-indene-2-carboxylate ethyl ester
6) 6-methoxy-1-(trans-(2-methylbuteneylimino-N-oxy)-3-phenyl-1H-indene-2-carboxylate ethyl ester
7) 1-(trans-isobutylimino-N-oxy)-6-methoxy-3-phenyl-1H-indene-2-carboxylate ethyl ester
8) 1-(trans-methylimino-N-oxy)-6-(2-morpholine-4-ylethoxy)-3-phenyl-1H-indene-2-carboxylate ethyl ester
9) 1-(trans-methylimino-N-oxy)-3-phenyl-6-(3-phenylpropoxy)-1H-indene-2-carboxylate ethyl ester
10) 1-(trans-methylimino-N-oxy)-6-phenetyloxy-3-phenyl-1H-indene-2-carboxylate ethyl ester
11) 3-furan-3-yl-1-(trans-methylimino-N-oxy)-6-(3-phenylpropoxy)-1H-indene-2-carboxylate ethyl ester
12) 6-hydroxy-1-(trans-methylimino-N-oxy)-3-phenyl-1H-indene-2-carboxylate ethyl ester
13) 1-(cis-methylimino-N-oxy)-3-phenyl-6-(3-phenylpropoxy)-1H-indene-2-carboxylate ethyl ester
14) 3-(trans-methylimino-N-oxy)-1-phenyl-3H-indene-5-ol
15) 1-(trans-methylimino-N-oxy)-3-phenyl-6-(5-phenylpentyloxy)-1H-indene-2-carboxylate ethyl ester
16) 1-(cis-methylimino-N-oxy)-3-phenyl-6-(5-phenylpentyloxy)-1H-indene-2-carboxylate ethyl ester
17) 6-[2-(4-chlorophenoxy)acetoxy]-1-(trans-methylimino-N-oxy)-3-phenyl-1H-indene-2-carboxylate ethyl ester
18) 6-[2-(4-chlorophenoxy)ethoxy]-1-(trans-methylimino-N-oxy)-3-phenyl-1H-indene-2-carboxylate ethyl ester
19) 1-(trans-methylimino-N-oxy)-6-(naphthalene-2-ylmethoxy)-3-phenyl-1H-indene-2-carboxylate ethyl ester
20) methyl-[3-phenyl-6-(3-phenylpropoxy)indene-1-yllidene]amine-N-oxide
21) 1-(trans-methylimino-N-oxy)-6-[2-(5-methyl-2-phenylthiazol-4-yl)ethoxy]-3-phenyl-1H-indene-2-carboxylate ethyl ester
22) 1-(trans-methylimino-N-oxy)-3-(3-phenylpropoxy)-1H-indene-2-carboxylate ethyl ester
23) 6-[2-(4-hydroxyphenyl)ethoxy]-1-(trans-methylimino-N-oxy)-3-phenyl-1H-indene-2-carboxylate ethyl ester
24) 6-(2-adaman-1-ylethoxy)-1-(trans-methylimino-N-oxy)-3-phenyl-1H-indene-2-carboxylate ethyl ester
25) 6-(2-cyclohexylethoxy)-1-(trans-methylimino-N-oxy)-3-phenyl-1H-indene-2-carboxylate ethyl ester
26) 1-(trans-methylimino-N-oxy)-3-phenyl-6-(3-phenylpropoxy)-1H-indene-2-carboxylate ethyl ester
27) 6-[2-(2-fluorophenyl)ethoxy]-1-(trans-methylimino-N-oxy)-3-phenyl-1H-indene-2-carboxylate ethyl ester
28) 6-[2-(3-fluorophenyl)ethoxy]-1-(trans-methylimino-N-oxy)-3-phenyl-1H-indene-2-carboxylate ethyl ester
29) 6-[2-(4-fluorophenyl)ethoxy]-1-(trans-methylimino-N-oxy)-3-phenyl-1H-indene-2-carboxylate ethyl ester
30) 1-(trans-methylimino-N-oxy)-3-phenyl-6-[2-(3-trifluoromethylphenyl)ethoxy]-1H-indene-2-carboxylate ethyl ester
31) 6-(4-methoxycarbonylbenzyloxy)-1-(trans-methylimino-N-oxy)-3-phenyl-1H-indene-2-carboxylate ethyl ester
32) 1-(trans-methylimino-N-oxy)-3-phenyl-6-(3-phenylpropoxy)-1H-indene-2-carboxylate ethyl amide
33) 1-(trans-methylimino-N-oxy)-6-(2-morpholine-4-ylethoxy)-3-phenyl-1H-indene-2-carboxylate ethyl ester
34) 6-[2-(cyclohexylmethylamino)ethoxy]-1-(trans-methylimino-N-oxy)-3-phenyl-1H-indene-2-carboxylate ethyl ester TABLE 1-continued

| No. | structure | $^1$H-NMR(CDCl$_3$, 300 M Hz) δ |
|---|---|---|

35) 3-(2-fluorophenyl)-6-methoxy-1-(trans-methylimino-N-oxy)-1H-indene-2-carboxylate ethyl ester
36) 1-(trans-methylimino-N-oxy)-6-[2-(4-methylpiperazine-1-yl)ethoxy]-3-phenyl-1H-indene-2-carboxylate ethyl ester
37) (2,3-diphenyl indene-1-yllindene)methylamine-N-oxide
38) 1-(trans-methylimino-N-oxy)-3-phenyl-6-(3-phenylpropoxy)-1H-indene-2-carboxylate isopropyl amide
39) 1-(trans-methylimino-N-oxy)-3-phenyl-6-(3-phenylpropoxy)-1H-indene-2-carboxylate cyclohexyl amide
40) [1-(trans-methylimino-N-oxy)-3-phenyl-6-(3-phenylpropoxy)-1H-indene-2-yl]morpholine-4-yl-methanone
41) 1-(trans-methylimino-N-oxy)-6-(2-morpholine -4-yl-ethoxy)-3-phenyl-1H-indene-2-carboxylate cyclohexyl amide
42) 1-(trans-methylimino-N-oxy)-3-phenyl-5-(3-phenylpropoxy)-1H-indene-2-carboxylate ethyl ester
43) 1-(trans-methylimino-N-oxy)-6-phenethyloxymethyl-3-phenyl-1H-indene-2-carboxylate ethyl ester
44) (6-methoxy-3-phenylindene-1-yllindene)methylamine-N-oxide
45) 1-(cis-methylimino-N-oxy)-6-(2-morpholine-4-ylethoxy)-3-phenyl-1H-indene-2-carboxylate ethyl ester
46) 6-(2-bromoethoxy)-1-(trans-methylimino-N-oxy)-3-phenyl-1H-indene-2-carboxylate ethyl ester
47) 1-(trans-methylimino-N-oxy)-6-(2-morpholine-4-ylethoxy)-3-phenyl-1H-indene-2-carboxylate tert-buthyl ester
48) 1-(trans-methylimino-N-oxy)-5,6-methylenedioxy-1-oxo-3-phenyl-1H-indene-2-carboxylate ethyl ester
49) 4-[2-isopropylcarbamoyl-3-(trans-methylimino-N-oxy)-1-phenyl-3H-indene-5-yl-oxylmethyl]benzoate methyl ester
50) 1-(trans-methylimino-N-oxy)-6-(2-morpholine-4-ylethoxy)-3-phenyl-1H-indene-2-carboxylate isopropyl amide
51) 1-(trans-methylimino-N-oxy)-6-(2-morpholine-4-ylethoxy)-3-phenyl-1H-indene-2-carboxylate cyclopropyl amide
52) 3-(3-fluorophenyl)-1-(trans-methylimino-N-oxy)-6-(2-morpholine-4-ylethoxy)-1H-indene-2-carboxylate isopropyl amide
53) (6-methoxy-1-(trans-methylimino-N-oxy)-3-phenyl-1H-indene-2-yl)acetate ethyl ester
54) (6-methoxy-1-(cis-methylimino-N-oxy)-3-phenyl-1H-indene-2-yl)acetate ethyl ester
55) 5-[2-(5-ethylpyridine-2-yl)ethoxy]-1-(trans-methylimino-N-oxy)-3-phenyl-1H-indene-2-carboxylate isopropyl amide
56) 1-(trans-methylimino-N-oxy)-6-(3-phenylpropoxy)-3-p-tolyl-1H-indene-2-carboxylate ethyl ester
57) 1-(trans-methylimino-N-oxy)-6-(3-phenylpropoxy)-3-thiophene-2-yl-1H-indene-2-carboxylate ethyl ester
58) 3-(4-chlorophenyl)-1-(trans-methylimino-N-oxy)-6-(3-phenylpropoxy)-1H-indene-2-carboxylate ethyl ester
59) 3-(5-chlorothiophene-2-yl)-1-(trans-methylimino-N-oxy)-6-(3-phenylpropoxy)-1H-indene-2-carboxylate ethyl ester
60) 1-(trans-methylimino-N-oxy)-6-(3-phenylpropoxy)-3-m-tolyl-1H-indene-2-carboxylate ethyl ester
61) 1-(trans-methylimino-N-oxy)-3-(4-phenoxyphenyl)-6-(3-phenylpropoxy)-1H-indene-2-carboxylate ethyl ester
62) 3-benzo-[1,3]-dioxol-5-1-(trans-methylimino-N-oxy)-6-(3-phenylpropoxy)-1H-indene-2-carboxylate ethyl ester
63) methyl-[6-(3-phenylpropoxy)-3-pyridine-2-yl-indene-1-yllidene]amine-N-oxide
64) 3-furan-2-yl-1-(trans-methylimino-N-oxy)-6-(3-phenylpropoxy)-1H-indene-2-carboxylate ethyl ester
65) 3-ethyl-1-(trans-methylimino-N-oxy)-6-(3-phenylpropoxy)-1H-indene-2-carboxylate ethyl ester
66) 3-methyl-1-(trans-methylimino-N-oxy)-6-(3-phenylpropoxy)-1H-indene-2-carboxylate ethyl ester
67) 1-(trans-methylimino-N-oxy)-6-(3-phenylpropoxy)-3-thiophene-3-yl-1H-indene-2-carboxylate ethyl ester
68) 3-cyclopropyl-1-(trans-methylimino-N-oxy)-6-(3-phenylpropoxy)-1H-indene-2-carboxylate ethyl ester
69) 1-(trans-methylimino-N-oxy)-6-(2-morpholine-4-ylethoxy)-3-thiophene-3-yl-1H-indene-2-carboxylate ethyl ester
70) 3-benzo-[b]-thiophene-3-yl-1-(trans-methylimino-N-oxy)-6-(3-phenylpropoxy)-1H-indene-2-carboxylate ethyl ester
71) 3-(1H-imidazol-4-yl)-1-(trans-methylimino-N-oxy)-6-(3-phenylpropoxy)-1H-indene-2-carboxylate ethyl ester
72) 3-(1-ethyl propyl)-1-(trans-methylimino-N-oxy)-6-(3-phenylpropoxy)-1H-indene-2-carboxylate ethyl ester
73) 1-(trans-methylimino-N-oxy)-3-phenyl-6-(3-phenylpropoxy)-1H-indene-2-carboxylate amide
74) 6-(4-benzylmorpholine-2-ylmethoxy)-1-(trans-methylimino-N-oxy)-3-phenyl-1H-indene-2-carboxylate isopropyl amide
75) 1-(trans-methylimino-N-oxy)-3-phenyl-6-(3-phenylpropoxy)-1H-indene-2-carbonitrile
76) 1-(trans-methylimino-N-oxy)-5,6-methylenedioxy-1-oxo-3-phenyl-1H-phenyl-2-carboxylate isopropyl amide
77) 1-(trans-methylimino-N-oxy)-6-morpholine-4-ylmethyl-3-phenyl-1H-indene-2-carboxylate ethyl ester
78) 1-(trans-methylimino-N-oxy)-3-phenyl-6-(2-pyridine-2-ylethoxy)-1H-indene-2-carboxylate ethyl ester
79) 6-[2-(5-ethylpyridine-2-yl)ethoxy]-1-(trans-methylimino-N-oxy)-3-phenyl-1H-indene-2-carboxylate ethyl ester
80) 1-(trans-methylimino-N-oxy)-3-phenyl-6-(2-pyridine-2-ylethoxy)-1H-indene-2-carboxylate isopropyl amide
81) 6-[2-(5-ethylpyridine-2-yl)ethoxy]-1-(trans-methylimino-N-oxy)-3-phenyl-1H-indene-2-carboxylate isopropyl amide
82) methyl-[6-(2-morpholine-4-ylethoxy)-3-phenylindene-1-yllidene]amine-N-oxide
83) 5,6-bis-methanesulfonyloxy-1-(trans-methylimino-N-oxy)-3-phenyl-1H-indene-2-carboxylate ethyl ester
84) 1-(trans-methylimino-N-oxy)-6-(2-morpholine-4-ylethoxy)-3-phenyl-1H-indene-2-carboxylate isobutyl ester
85) 1-(trans-methylimino-N-oxy)-6-(2-morpholine-4-ylethoxy)-3-phenyl-1H-indene-2-carboxylate methyl ester
86) 1-(cis-methylimino-N-oxy)-6-(2-morpholine-4-ylethoxy)-3-phenyl-1H-indene-2-carboxylate methyl ester
87) 1-(trans-methylimino-N-oxy)-6-(2-morpholine-4-ylethoxy)-3-phenyl-1H-indene-2-carboxylate propyl ester
88) 3-(4-fluorophenyl)-1-(trans-methylimino-N-oxy)-6-(2-morpholine-4-ylethoxy)-1H-indene-2-carboxylate methyl ester
89) 1-(trans-methylimino-N-oxy)-3-phenyl-6-(pyridine-2-yletoxy)-1H-indene-2-carboxylate ethyl ester
90) 1-(trans-methylimino-N-oxy)-3-phenyl-6-(pyridine-2-yloxy)-1H-indene-2-carboxylate ethyl ester
91) 6-(3-methoxybenzyloxy)-1-(trans-methylimino-N-oxy)-3-phenyl-1H-indene-2-carboxylate ethyl ester
92) 1-(trans-methylimino-N-oxy)-6-(2-morpholine-4-ylethoxy)-3-thiophene-3-yl-1H-indene-2-carboxylate isopropyl amide
93) 3-(1-ethylpropyl)-1-(trans-methylimino-N-oxy)-6-(2-morpholine-4-ylethoxy)-1H-indene-2-carboxylate ethyl ester
94) 3-benzo-[b]-thiophene-3-yl-1-(trans-methylimino-N-oxy)-6-(2-morpholine-4-ylethoxy)-1H-indene-2-carboxylate isopropyl amide
95) 3-(4-fluorophenyl)-1-(trans-methylimino-N-oxy)-6-(2-morpholine-4-ylethoxy)-1H-indene-2-carboxylate isopropyl amide
96) 3-(1-ethylpropyl)-1-(trans-methylimino-N-oxy)-6-(2-morpholine-4-ylethoxy)-1H-indene-2-carboxylate isopropyl amide
97) 1-(trans-methylimino-N-oxy)-6-(2-morpholine-4-ylethoxy)-3-(2,4,6-trimethylphenyl)-1H-indene-2-carboxylate ethyl ester
98) 3-(2,6-dimethylphenyl)-1-(trans-methylimino-N-oxy)-6-(2-morpholine-4-ylethoxy)-1H-indene-2-carboxylate ethyl ester
99) 1-(trans-methylimino-N-oxy)-3-phenyl-5-(2-pyridine-2-ylethoxy)-1H-indene-2-carboxylate isopropyl amide
100) 1-(trans-methylimino-N-oxy)-5-(2-morpholine-4-ylethoxy)-3-phenyl-1H-indene-2-carboxylate isopropyl amide
101) 1-(cis-methylimino-N-oxy)-6-(2-morpholine-4-ylethoxy)-3-phenyl-1H-indene-2-carboxylate isopropyl amide
102) 3-(3-fluorophenyl)-1-(trans-methylimino-N-oxy)-6-(2-pyridine-2-ylethoxy)-1H-indene-2-carboxylate isopropyl amide
103) 6-[2-(5-ethylpyridine-2-yl)ethoxy]-3-(3-fluorophenyl)-1-(trans-mehtylimino-N-oxy)-1H-indene-2-carboxylate isopropyl amide
104) 3-(4-cyanophenyl)-6-(2-morpholine-4-ylethoxy)-1-(trans-methylimino-N-oxy)-1H-indene-2-carboxylate ethyl ester
105) 1-(trans-methylimino-N-oxy)-3-phenyl-6-(2-pyridine-2-ylethoxy)-1H-indene-2-carboxylate isopropyl ester.

The inventive indene derivative of formula (I) and a pharmaceutically acceptable salt thereof is capable of selectively modulating activities of PPARs, and thus it causes no adverse side effects such as weight gain, cardiac hypertrophy, edema and liver damage.

The present invention also includes within its scope a pharmaceutical composition comprising a therapeutically effective amount of the novel compounds of formula (I), as defined above, or a pharmaceutically acceptable salt thereof as an active ingredient together with a pharmaceutically acceptable carrier.

The inventive pharmaceutical composition is useful for the treatment and prevention of disorders modulated by PPARs, i.e., metabolic syndromes such as diabetes, obesity, arteriosclerosis, hyperlipidemia, hyperinsulinism and hypertension; inflammatory diseases such as osteoporosis, liver cirrhosis and asthma; and cancer.

The pharmaceutical compositions of the invention may be formulated for administration orally or parenterally, including intravenous, intraperitoneal, subcutaneous, rectal and topical routes of administration. The composition for oral administration may take various forms such as tablets, soft and hard gelatin capsules, aqueous solutions, suspensions, emulsions, syrups, granules and elixirs, which may contain conventional additives such as a diluent (e.g., lactose, dextrose, sucrose, mannitol, sorbitol, cellulose and glycine), a lubricant (e.g., silica, talc, stearic acid or its magnesium and calcium salts and polyethylene glycol). In the case of the tablet form, the composition may further comprise a binder (e.g., magnesium aluminum silicate, starch paste, gelatin, tragacanth, methyl cellulose, sodium carboxymethyl cellulose and polyvinyl pyrrolidone) and optionally a disintegrant (e.g., starch, agar and alginic acid or its sodium salt), absorbent, colorant, flavor, sweetener and the like.

The composition may be sterilized and/or contain an adjuvant such as a preservative, stabilizer, wetting agent, emulsifier, a salt for controlling an osmotic pressure and/or a buffer solution, and other pharmaceutically effective materials.

The inventive compounds may be administered as an active ingredient in an effective amount ranging from about 0.1 to 500 mg/kg, preferably from about 0.5 to 100 mg/kg per day in a single dose or in divided doses.

The following Preparations and Examples are given for the purpose of illustration only and are not intended to limit the scope of the invention.

Synthesis of Compound of Formula (I) According to Reaction Scheme (II)

Example 1

Preparation of 1-(trans-methylimino-N-oxy)-3-phenyl-6-(3-phenylpropoxy)-1H-indene-2-carboxylate ethyl ester (No. 9 compound of Table 1)

(step 1) Preparation of 3-hydroxy benzyl chloride (formula (VI))

3-Hydroxybenzylalcohol (5 g, 40 mmol) and triethylamine (5.2 ml, 60 mmol) were dissolved in benzene (250 ml), and thionylchloride (5.2 ml) dissolved in benzene (50 ml) was added thereto at 0° C. The brownish reacting solution was stirred at room temperature for 6 hours. When the reaction was completed, the solution was washed with brine, and the water layer was extracted with methylene chloride. The organic extract was dried over anhydrous magnesium sulfate and concentrated under a reduced pressure to obtain the title compound (5.7 g, 99%).

$^1$H NMR (CDCl$_3$, 200 MHz) δ 7.22 (t, J=7.7 Hz, 1H), 6.96-6.78 (m, 3H), 5.73 (s, 1H), 4.52 (s, 2H) (step 2) Preparation of 2-(3-hydroxybenzyl)-3-oxo-3-phenylpropionate ethyl ester (Formula VII)

Ethyl benzoylacetate (8.7 ml, 50.2 mmol) and potassium carbonate (7.56 g, 54.7 mmol) were dissolved in dimethylformamide (500 ml) and stirred at room temperature for 1 hour, and then 3-hydroxybenzyl chloride (6.5 g, 45.6 mmol) dissolved in dimethylformamide (50 ml) was added thereto at 0° C. The brownish reacting solution was stirred at room temperature for 15 hours. When the reaction was completed, the solution was washed with saturated ammonium chloride, and extracted with diethyl ether. The organic layer was dried over anhydrous magnesium sulfate, concentrated under a reduced pressure, and the residue was subjected to silica gel column chromatography (ethyl acetate:hexane=1:5) to obtain the title compound (10.2 g, 75%) as pale yellow oil.

$^1$H NMR (CDCl$_3$, 200 MHz) δ 7.97-7.92 (m, 2H), 7.56-7.39 (m, 3H), 7.11 (t, J=7.7 Hz, 1H), 6.79-6.63 (m, 3H), 5.37 (brs, 1H), 4.62 (t, J=7.3 Hz, 1H), 4.13 (q, J=7.1 Hz, 2H), 3.27 (d, J=7.3 Hz, 2H), 1.11 (t, J=7.1, 3H) (step 3) Preparation of 6-hydroxy-3-phenyl-1H-indene-2-carboxylate ethyl ester (formula (VII))

2-(3-Hydroxybenzyl)-3-oxo-3-phenylpropionate ethyl ester (5 g, 16.7 mmol) and polyphosphoric acid (20 g) were mixed and stirred at room temperature for 1 hour. The reaction mixture was washed with water to remove polyphosphoric acid, and extracted with ethyl acetate. The organic layer was dried over anhydrous magnesium sulfate, concentrated under a reduced pressure. And the residue was subjected to silica gel column chromatography (ethyl acetate:hexane=1:4) to obtain the title compound (47%) as yellow sticky oil.

$^1$H NMR (CDCl$_3$, 200 MHz) δ 7.44-7.38 (m, 5H), 7.12 (d, J=8.4 Hz, 1H), 7.02 (d, J=2.0 Hz, 1H), 6.76 (dd, J=8.4, 2.0 Hz, 1H), 4.12 (q, J=7.1 Hz, 2H), 3.80 (s, 2H), 1.12 (t, J=7.1 Hz, 3H)

(step 4) Preparation of 6-hydroxy-1-oxo-3-phenyl-1H-indene-2-carboxylate ethyl ester (formula (II))

6-Hydroxy-3-phenyl-1H-indene-2-carboxylate ethyl ester (1 g, 3.57 mmol) was dissolved in 1,4-dioxane (50 ml), and then selenium dioxide (5.49 g, 53.55 mmol) was added thereto. The mixture was refluxed for 12 hour with vigorous stirring. The resulting mixture was filtered and concentrated, and the concentrate was extracted with ethyl acetate. The extract was washed with brine, and the organic layer was dried over anhydrous magnesium sulfate, concentrated under a reduced pressure, and the residue was subjected to silica gel column chromatography (ethyl acetate:hexane=1:4) to obtain the title compound (58%) as a rich red solid.

$^1$H NMR (CDCl$_3$, 200 MHz) δ 7.49 (5H, s), 7.15 (d, J=2.4 Hz, 1H), 7.01 (d, J=7.9 Hz, 1H), 6.91 (dd, J=8.2, 2.4 Hz, 1H), 4.17 (q, J=7.1 Hz, 2H), 1.13 (t, J=7.1, 3H)

(Step 5) Preparation of 3-phenyl-6-(3-phenylpropyloxy)-1-oxo-1H-indene-2-carboxylate ethyl ester [compound of formula (II)] (reaction scheme (VII))

(5-1)
6-Hydroxy-1-oxo-3-phenyl-1H-indene-2-carboxylate ethyl ester (1.7 g, 6.07 mmol), 3-phenylpropanol (1.65 g, 12.14 mmol) and triphenylphosphine (3.18 g, 12.14 mmol) were dissolved in tetrahydrofuran (100 ml). Diethyl azodicarboxylate (2 ml, 12.14 mmol) dissolved in tetrahydrofuran (20 ml) was added dropwise thereto at 0° C. After stirring for 6 hours at room temperature, the mixture was washed with brine, extracted with ethyl acetate, the extract was dried over anhydrous magnesium sulfate, the concentrated under a reduced pressure, and the residue was purified by silica gel column chromatography (diethyl ether:hexane=1:10) to obtain the title compound (yield 85%) as a dark red solid.

$^1$H NMR (300 MHz, CDCl$_3$): 7.50 (s, 5H), 7.47-7.16 (m, 6H), 7.06 (d, J=8.0 Hz, 1H), 6.80 (dd, J=8.1, 2.4 Hz, 1H), 4.18 (q, J=7.1 Hz, 2H), 4.00 (t, J=6.2 Hz, 2H), 2.81 (t, J=7.4 Hz, 1H), 1.15 (t, J=7.1 Hz, 3H).

(5-2)
6-Hydroxy-1-oxo-3-phenyl-1H-indene-2-carboxylate ethyl ester (2 g, 6.80 mmol), potassium carbonate (1.41 g, 10.194 mmol), and sodium iodide (200 mg, 1.359 mmol) were dissolved in dimethylformamide (100 ml). 1-Bromo-3-phenylpropane (2.01 ml, 13.59 mmol) was added thereto at room temperature, was stirred for 12 hours at 60° C., and washed with saturated ammonium chloride. The organic layer obtained by extracting the reaction mixture with ethyl acetate was dried over anhydrous magnesium sulfate, concentrated, and the residue was purified by silica gel column chromatography (ethyl acetate:hexane=1:4) to obtain the title compound (yield 85%) as a dark red solid.

(Step 6) Preparation of 1-(trans-methyl imino-N-oxy)-6-(3-phenylpropyloxy)-3-phenyl-1H-indene-2-carboxylate ethyl ester [No. 9 compound of Table 1] (reaction scheme (I))

(6-1)
3-Phenyl-6-(3-phenylpropyloxy)-1-oxo-1H-indene-2-carboxylate ethyl ester (2 g, 4.85 mmol) and hydroxyamine.hydrochloric acid (1.01 g, 14.6 mmol) were dissolved in pyridine (1.57 ml, 19.4 mmol). The reaction mixture was stirred for 1 hour at 70° C., and washed with saturated ammonium chloride. The organic layer obtained by extracting the reaction mixture with ethyl acetate was dried over anhydrous magnesium sulfate, concentrated, and the residue was purified by silica gel column chromatography (ethyl acetate:hexane=1:2) to obtain 1-hydroxyimino-3-phenyl-6-(3-phenylpropyloxy)-1H-indene-2-carboxylate ethyl ester (yield 9.5%) as a yellow solid.

$^1$H-NMR (CDCl$_3$, 200 MHz): δ 8.09 (d, J=2.3 Hz, 1H), 7.48-7.15 (m, 1H), 7.10 (d, J=8.4 Hz, 1H), 6.86 (dd, J=8.4, 2.3 Hz, 1H), 4.16 (q, J=7.1 Hz, 2H), 4.04 (t, J=6.3 Hz, 2H), 2.83 (t, J=6.3 Hz, 2H), 2.10 (m, 2H), 1.04 (t, J=7.1 Hz, 3H).

1-Hydroxyimino-3-phenyl-6-(3-phenylpropyloxy)-1H-indene-2-carboxylate ethyl ester (1.98 g, 4.63 mmol), methyl iodide (1.15 ml, 18.5 mmol) and potassium carbonate (1.92 g, 13.9 mmol) were dissolved in dimethylformamide (50 ml), stirred for 30 min at room temperature, and washed with saturated ammonium chloride. The organic layer obtained by extracting the reaction mixture with ethyl acetate was dried over anhydrous magnesium sulfate, concentrated, and the residue was purified by silica gel column chromatography (ethyl acetate:hexane=1:2) to obtain the title compound (yield 15%) as a red solid.

(6-2)
1-Oxo-3-phenyl-6-(3-phenylpropoxy)-1H-indene-2-carboxylate ethyl ester (0.75 g, 1.82 mmol) was dissolved in ethanol (30 ml). N-methyl hydroxylamine hydrochloride (0.46 g, 5.4 mmol) and 2,6-lutidine (0.584 g, 5.4 mmol) were added thereto, and stirred for 40 hours at 70° C. in a pressure-tube. Ethanol was removed from the reaction mixture under a reduced pressure, and the resulting residue was extracted with ethyl acetate. After washing with saturated ammonium chloride, the organic layer was dried over anhydrous magnesium sulfate and purified by silica gel column chromatography to obtain the title compound (407 mg, yield 40%) as a red solid.

Example 2

Preparation of 1-(trans-methylimino-N-oxy)-6-(2-morpholine-4-ylethoxy)-3-phenyl-1H-indene-2-carboxylate ethyl ester [No. 33 compound of Table 1]

(Step 1) Preparation of 3-phenyl-6-(2-morpholine-4-ylethoxy)-1-oxo-1H-indene-2-carboxylate ethyl ester [compound of formula (II)] (reaction scheme (VII))

6-Hydroxy-1-oxo-3-phenyl-1H-indene-2-carboxylate ethyl ester [compound of formula (II)] (10.90 g, 26.75 mmol) prepared in Step 4 of Example 1 was dissolved in tetrahydrofuran:benzene (270 ml:90 ml). Then, 4-(2-hydroxyethyl) morpholine (5.83 g, 44.45 mmol) and triphenylphosphine (11.66 g, 44.45 mmol) were added thereto. Diisopropylazodicarboxylate (8.99 g, 44.45 mmol) was added dropwise to the mixture at 0° C., and stirred for 2 hours at room temperature. The reaction mixture was washed with saturated sodium chloride and extracted with ethyl acetate. The organic layer was dried over anhydrous magnesium sulfate, concentrated, and the resulting residue was purified by column chromatography (ethyl acetate) to obtain the title compound (14 g, yield 93%) as a red solid.

$^1$H NMR (200 MHz, CDCl$_3$): δ 7.50 (s, 5H), 7.19 (d, J=2.0 Hz, 1H), 7.07 (d, J=8.2 Hz, 1H), 6.84 (dd, J=8.2, 2.2 Hz, 1H), 4.22-4.14 (m, 4H), 3.73 (t, J=4.5 Hz, 4H), 2.81 (t, J=5.6 Hz, 2H), 2.57 (t, J=4.5 Hz, 4H), 1.15 (t, J=7.1 Hz, 3H).

(Step 2) Preparation of 1-(trans-methylimino-N-oxy)-6-(2-morpholine-4-ylethoxy)-3-phenyl-1H-indene-2-carboxylate ethyl ester [No. 33 compound of Table 1] (reaction scheme (I))

3-Phenyl-6-(2-morpholine-4-ylethoxy)-1-oxo-1H-indene-2-carboxylate ethyl ester (14.6 g, 35.83 mmol) was dissolved in ethanol. N-methyl hydroxylamine hydrochloride (8.98 g, 107.49 mmol) and 2,6-lutidine (11.52 g, 107.49 mmol) were added thereto and the mixture was stirred for 3 days at 70° C. in a pressure-tube. Ethanol was removed under a reduced pressure and the resulting residue was extracted with ethyl acetate. After washing with saturated ammonium chloride, the organic layer was dried over anhydrous magnesium sulfate and purified by column chromatography to obtain the title compound (4.18 g, yield 27%, mp 102-104° C.) as a red solid.

Example 3

Preparation of 1-(trans-methylimino-N-oxy)-5,6-methylenedioxy-1-oxo-3-phenyl-1H-indene-2-carboxylate ethyl ester [No. 48 compound of Table 1]

(Step 1) Preparation of 5-chloromethylbenzo[1,3]dioxol [compound of chemical formula (VI)]

Piperonyl alcohol (10 g, 65.7 mmol) was dissolved in benzene. Triethylamine (11 ml, 78.8 mmol) and thionyl chloride (11 ml, 131.4 mmol) were added dropwise thereto and was stirred for 24 hours at 0° C. The reaction mixture was extracted with sodium bicarbonate and ethyl acetate, the organic layer was separated, and dried over anhydrous magnesium sulfate to obtain 5-chloromethyl benzo[1,3]dioxol (11.2 g, yield 100%).

$^1$H NMR (200 MHz, CDCl$_3$): δ 6.88-6.75 (m, 3H), 5.97 (s, 2H), 4.53 (s, 2H).

(Step 2) Preparation of 2-benzo[1,3]dioxol-5-ylmethyl-3-oxo-3-phenylpropionate ethyl ester [compound of formula (VII)]

5-Chloromethyl benzo[1,3]dioxol (11.2 g, 65.7 mmol) was dissolved in Dimethylformamide. Then, potassium carbonate (18.2 g, 131.4 mmol), sodium iodide (10.8 g, 72.27 mmol) and ethyl benzoylacetate (12.5 ml, 72.27 mmol) were added thereto and stirred for 5 hours at room temperature. The reaction mixture was extracted with ammonium chloride and ether, the organic layer was separated, dried over anhydrous magnesium sulfate, concentrated, and the resulting residue was purified by column chromatography to obtain 2-benzo[1,3]dioxol-5-ylmethyl-3-oxo-3-phenylpropionate ethyl ester (16.4 g, 76%).

$^1$H NMR (200 MHz, CDCl$_3$): δ 7.98-6.69 (m, 3H), 5.90 (s, 2H), 4.56 (t, J=7.4 Hz, 1H), 4.09 (q, J=7.2 Hz, 2H), 3.26 (d, J=7.4 Hz, 2H), 1.13 (t, J=7.2 Hz, 3H).

(Step 3) Preparation of 5,6-methylenedioxy-3-phenyl-1H-indene-2-carboxylate ethyl ester [compound of formula (VIII)]

2-Benzo[1,3]dioxol-5-ylmethyl-3-oxo-3-phenylpropionate ethyl ester (16 g, 49.03 mmol) and polyphosphoric acid (160 g) were mixed and stirred for 1 hour at room temperature. After the reaction was completed, the mixture was washed with water to remove polyphosphoric acid, and extracted with ethyl acetate. The organic layer was dried over anhydrous magnesium sulfate, concentrated, and the resulting residue was purified by column chromatography to obtain 5,6-methylenedioxy-3-phenyl-1H-indene-2-carboxylate ethyl ester (4.53 g, yield 30%) as a white solid.

$^1$H NMR (200 MHz, CDCl$_3$): δ 7.41 (m, 5H), 7.00 (s, 1H), 6.69 (s, 1H), 5.96 (s, 2H), 4.08 (q, J=7.2 Hz, 2H), 3.75 (s, 2H), 1.10 (t, J=7.2 Hz, 3H).

(Step 4) Preparation of 5,6-methylene dioxy-1-oxo-3-phenyl-1H-indene-2-carboxylate ethyl ester [compound of formula (II)]

5,6-Methylenedioxy-3-phenyl-1H-indene-2-carboxylate ethyl ester (3 g, 9.73 mmol) was dissolved in 1,4-dioxane. Selenium dioxide (10.8 g, 97.3 mmol) was added thereto and the reaction mixture was refluxed while stirring for 1 day, followed by cooling. The solution obtained after filtering residual solid selenium dioxide was combined with 1M sodium bicarbonate, and extracted with ether/water. The extract was dried over anhydrous magnesium sulfate, concentrated, and the resulting residue was purified by column chromatography to obtain 5,6-methylenedioxy-1-oxo-3-phenyl-1H-indene-2-carboxylate ethyl ester (2.18 g, yield 70%).

$^1$H NMR (200 MHz, CDCl$_3$): δ 7.51 (s, 5H), 7.11 (s, 1H), 6.67 (s, 1H), 6.07 (s, 2H), 4.17 (q, J=7.2 Hz, 2H), 1.17 (t, J=7.2 Hz, 3H).

(Step 5) Preparation of 1-(trans-methylimino-N-oxy)-5,6-methylene dioxy-1-oxo-3-phenyl-1H-indene-2-carboxylate ethyl ester [No. 48 compound of Table 1] (reaction scheme (I))

5,6-Methylenedioxy-1-oxo-3-phenyl-1H-indene-2-carboxylate ethyl ester (100 mg, 0.324 mmol) was dissolved in ethanol. 2,6-Lutidine (0.11 ml, 0.973 mmol) and methyl hydroxylamine (81.27 mg, 0.973 mmol) were added thereto and the mixture was stirred for 3 days at 70° C. in a pressure-tube. The reaction mixture was extracted with saturated sodium chloride and ethyl acetate, the organic layer was separated, dried over anhydrous magnesium sulfate, concentrated, and the resulting residue was purified by column chromatography (10~20% ethyl acetate/hexane) to obtain 1-(trans-methylimino-N-oxy)-5,6-methylenedioxy-1-oxo-3-phenyl-1H-indene-2-carboxylate ethyl ester (10 mg, yield 9%, mp 119-121° C.).

Preparation of Compound of Chemical Formula (I) According to Reaction Scheme (III)

Example 4

Preparation of 1-(trans-methylimino-N-oxy)-6-(2-morpholine-4-ylethoxy)-3-phenyl-1H-indene-2-carboxylate isopropyl amide [No. 50 compound of Table 1]

(Step 1) Preparation of 1-(3-benzyloxyphenyl)ethanone

3-Hydroxyacetophenone (136.15 g, 1 mol), potassium carbonate (414.63 g, 2 mol), KI (33.2 g, 0.2 mol), and benzyl bromide (171.04 g, 1 mol) were dissolved in acetone and the reaction mixture was refluxed while stirring for 24 hours, followed by washing with brine. The reaction mixture was extracted with ethyl acetate, the extract was dried over anhydrous magnesium sulfate, concentrated, and the resulting residue was purified by column chromatography (ethyl acetate:hexane=1:3) to obtain 1-(3-benzyloxyphenyl)ethanone (221.8 g, yield 98%) in an oil state.

$^1$H NMR (200 MHz, CDCl$_3$): δ 7.59-7.53 (m, 2H), 7.44-7.33 (m, 6H) 7.19 (m, 1H), 5.11 (s, 2H), 2.6 (s, 3H).

(Step 2) Preparation of 3-(3-benzyloxyphenyl)-3-oxo-propionate ethyl ester [compound of formula (IX)]

1-(3-Benzyloxyphenyl)ethanone (218 g, 966.10 mmol) was dissolved in diethyl carbonate and sodium hydride (60% oil) (46.37 g, 1.15 mmol) was slowly added thereto at 0° C., and then stirred for 3 hours at 60° C. After the reaction was completed, ice water and acetic acid were added to the reaction mixture, extracted with ethyl acetate/saturated sodium chloride, the organic layer was separated, and dried over anhydrous magnesium sulfate. The solvent was removed under a reduced pressure and the resulting residue was purified by column chromatography (ethyl acetate:hexane=1:10) to obtain 3-(3-benzyloxyphenyl)-3-oxopropionate ethyl ester (184.68 g, yield 84%) in an oil state.

$^1$H NMR (200 MHz, CDCl$_3$): δ 7.59-7.50 (m, 2H), 7.47-7.32 (m, 6H), 7.21 (m, 1H), 5.11 (s, 2H), 4.29-4.16 (m, 2H), 3.97 (s, 2H), 1.37-1.23 (m, 3H).

(Step 3) Preparation of 2-(3-benzyloxybenzoyl)-N-isopropyl-3-phenylacryl amide [compound of formula (IX)]

3-(3-Benzyloxyphenyl)-3-oxopropionate ethyl ester (174.42 g, 584.47 mmol) was dissolved in m-xylene and the reaction mixture was refluxed while stirring for 30 min at 150° C. Then, isopropylamine (38 g, 642.92 mmol) was added dropwise to the mixture. After stirring and refluxing for 24 hours at room temperature, the organic layer was extracted with saturated sodium chloride and ethyl acetate, dried over anhydrous magnesium sulfate, concentrated, and resulting residue was purified by column chromatography (ethyl acetate:hexane=1:2) to obtain 2-(3-benzyloxybenzoyl)-N-isopropyl-3-phenylacryl amide (127.13 g, yield 70%) as yellow oil.

$^1$H NMR (300 MHz, CDCl$_3$): δ 7.60-7.58 (m, 2H), 7.43-7.34 (m, 5H), 7.26-7.21 (m, 2H), 6.62 (b, 1H), 5.10 (s, 2H), 4.11 (m, 1H), 3.89 (s, 2H), 1.26-1.17 (m, 6H).

(Step 4) Preparation of 2-(3-benzyloxybenzoyl)-N-isopropyl-3-phenylacryl amide [compound of formula (XI)]

3-(3-Benzyloxyphenyl)-N-isopropyl-3-oxopropionamide (115.75 g, 371.744 mmol) was dissolved in benzene. Then, benzaldehyde [compound of formula (X)] (39.45 g, 371.74 mmol), piperidine (6.33 g, 74.34 mmol), and acetic acid (11.16 g, 185.87 mmol) were added thereto. The mixture was stirred and refluxed for 3 hours. After washing with saturated sodium chloride/sodium bicarbonate, the organic layer was extracted with ethyl acetate, dried over anhydrous magnesium sulfate, concentrated, recrystallized, and the resulting residue was purified by column chromatography (ethyl acetate:hexane=1:20) to obtain 2-(3-benzyl oxy benzoyl)-N-isopropyl-3-phenyl acryl amide (107.74 g, yield 73%) as a white solid.

$^1$H NMR (300 MHz, CDCl$_3$): δ 8.14 (s, 1H), 7.49-7.35 (m, 8H), 7.19-7.12 (m, 5H), 6.62 (b, 1H), 5.00 (s, 2H), 4.17 (m, 1H), 1.18 (d, J=6.6 Hz, 6H).

(Step 5) Preparation of 5-hydroxy-3-oxo-1-phenylindane-2-carboxylate isopropyl amide [compound of formula (XII)]

2-(3-Benzyloxybenzoyl)-N-isopropyl-3-phenylacryl amide (106.74 g, 267.19 mmol) was dissolved in dichloromethane. Methanesulfonic acid (256.78 g, 2.672 mmol) was added thereto and the mixture was stirred for 3 hours at room temperature. After the reaction was completed, the mixture was cooled to 0° C. followed by adding saturated sodium bicarbonate, and the organic layer extracted with dichloromethane. The extract was dried over anhydrous magnesium sulfate, concentrated, and the resulting residue was purified by column chromatography (ethyl acetate:hexane=1:2) to obtain 5-hydroxy-3-oxo-1-phenylindane-2-carboxylate isopropyl amide (36.086 g, yield 44%) as a white solid.

$^1$H NMR (300 MHz, CDCl$_3$): δ 7.33-7.10 (m, 7H), 6.71 (d, J=7.8 Hz, 1H), 5.74 (b, 1H), 5.16 (d, J=3.9 Hz, 1H), 4.10 (m, 1H), 3.41 (d, J=3.9 Hz, 1H), 1.28-1.16 (m, 6H).

(Step 6) Preparation of 6-hydroxy-1-oxo-3-phenyl-1H-indene-2-carboxylate isopropyl amide [compound of formula (II)]

Phenylselenylchloride (15.53 g, 81.07 mmol) was dissolved in dichloromethane and the temperature was adjusted to 0° C. Pyridine (7.00 g, 88.44 mmol) was added thereto. After 20 min, 5-hydroxy-3-oxo-1-phenyl indane-2-carboxylate isopropyl amide (22.8 g, 73.70 mmol) dissolved in dichloromethane was slowly added to the reaction mixture, which was further stirred for 3 hours. After the reaction was completed, the resultant was combined with 2N-hydrochloric acid and excess 30% hydrogen peroxide at 0° C. After adding water and saturated sodium bicarbonate to the mixture, the organic layer was extracted with dichloromethane, dried over anhydrous magnesium sulfate, concentrated, recrystallized, and filtered (ethyl acetate:hexane=1:2) to obtain 6-hydroxy-1-oxo-3-phenyl-1H-indene-2-carboxylate isopropyl amide (16.32 g, yield 72%) as a red solid.

$^1$H NMR (300 MHz, CDCl$_3$+DMSO-d$_6$): δ 9.76 (b, 1H), 7.76 (d, J=7.8 Hz, 1H), 7.56-7.44 (m, 4H), 6.88 (d, J=8.1 Hz, 1H), 6.76 (dd, J=8.1 Hz, J=2.1 Hz, 1H), 4.11 (m, 1H), 1.18 (d, J=6.3 Hz, 6H).

(Step 7) Preparation of 6-(2-morpholine-4-ylethoxy)-1-oxo-3-phenyl-1H-indene-2-carboxylate isopropyl amide [compound of formula (II)] (reaction scheme (VI))

6-Hydroxy-1-oxo-3-phenyl-1H-indene-2-carboxylate isopropyl amide (7.0 g, 22.78 mmol) was dissolved in tetrahydrofuran:benzene (150 ml:50 ml). Then, hydroxyethylmorpholine (3.59 g, 27.33 mmol) and triphenyl phosphine (7.17 g, 27.33 mmol) were added thereto. When the temperature was adjusted to 0° C., diisopropyl azodicarboxylate (5.53 g, 27.33 mmol) was added dropwise to the mixture followed by stirring for 2 hours at room temperature. The mixture was washed with brine and extracted with ethyl acetate. The separated organic layer was dried over anhydrous magnesium sulfate, concentrated, and the resulting residue was purified by column chromatography to obtain 6-(2-morpholine-4-yl ethoxy)-1-oxo-3-phenyl-1H-indene-2-carboxylate isopropyl amide (9.5 g, yield 99%).

$^1$H NMR (300 MHz, CDCl$_3$): δ 7.8 (m, 1H), 7.57-7.47 (m, 4H), 7.12 (d, J=2.4 Hz, 1H), 6.98 (d, J=8.1 Hz, 1H), 6.79 (dd, J=8.1 Hz, J=2.4 Hz, 1H), 4.18 (t, J=5.4 Hz, 2H), 3.74 (t, J=4.5 Hz, 4H), 2.81 (t, J=5.4 Hz, 2H), 2.57 (t, J=4.5 Hz, 4H), 1.19 (d, J=6.6 Hz, 6H).

(Step 8) Preparation of 1-(trans-methylimino-N-oxy)-6-(2-morpholine-4-ylethoxy)-3-phenyl-1H-indene-2-carboxylate isopropyl amide [No. 50 compound of Table 1] (reaction scheme (I))

6-(2-Morpholine-4-ylethoxy)-1-oxo-3-phenyl-1H-indene-2-carboxylate isopropyl amide (9.30 g, 22.11 mmol) was dissolved in ethanol. N-methyl hydroxylamine hydrochloride (5.54 g, 66.35 mmol) and 2,6-lutidine (7.11 g, 66.35 mmol) were added thereto and the mixture was stirred for 3 days at 75° C. in a pressure reactor. After removed ethanol under reduced pressure, the resultant was washed with saturated sodium chloride. Then, the organic layer extracted with ethyl acetate was dried over anhydrous magnesium sulfate, concentrated, and the resulting residue was purified by gel column chromatography to obtain 1-(trans-methyl imino-N-oxy)-6-(2-morpholine-4-ylethoxy)-3-phenyl-1H-indene-2-carboxylate isopropyl amide (3.8 g, yield 38%).

Preparation of Compound of Formula (I) According to Reaction Scheme (IV)

Example 5

Preparation of 1-(trans-methylimino-N-oxy)-6-(3-phenylpropyloxy)-3-phenyl-1H-indene-2-carboxylate ethyl ester [No. 9 compound of Table 1]

(Step 1) Preparation of 3'-(3-phenylpropyloxy)acetophenone [compound of formula (IX)]

3'-Hydroxyacetophenone (6.81 g, 50 mmol) and 1-bromo-3-phenyl propane (11.95 g, 60 mmol) were dissolved in dimethylformamide (70 ml). Then, potassium carbonate (15 g) and sodium iodide (0.5 g) were added thereto and the mixture was allowed to react for 7 hours at 80° C. Ethyl acetate (300 ml) and purified water (200 ml) were further added to the reaction mixture prior to stirring for 30 min. The organic layer extracted with ethyl acetate was dried over anhydrous magnesium sulfate, concentrated, and the resulting residue was purified by silica gel column chromatography (ethyl acetate:hexane=1:5) to obtain the title compound (12.0 g, yield 94.2%) as a gel.

$^1$H-NMR (200 MHz, CDCl$_3$): δ 7.47-7.55 (2H, m), 7.36 (1H, t, J=8.0 Hz), 7.27-7.30 (2H, m), 7.18-7.22 (3H, m), 7.13 (1H, dd, J=9.2, 2.8 Hz), 4.01 (2H, t, J=6.2 Hz), 2.82 (2H, t, J=8.0 Hz), 2.59 (3H, s), 2.13 (2H, m).

(Step 2) Preparation of 3'-(3-phenylpropyloxy)benzoylacetate ethyl ester [compound of formula (IX)]

3'-(3-Phenylpropyloxy)acetophenone (12.7 g, 50 mmol) obtained in (Step 1) of Example 5 and diethyl carbonate (7.1 g, 60 mmol) were dissolved in toluene (120 ml). While maintaining a temperature of 80~90° C., sodium hydride (2.6 g) was added dropwise thereto. At the same temperature, the reaction mixture was reacted for 2 hours followed by neutralizing with acetic acid. The organic layer extracted with purified water (200 ml) and ethyl acetate (200 ml) was dried over anhydrous magnesium sulfate, concentrated, and the resulting residue was purified by silica gel column chromatography (ethyl acetate:hexane=1:8) to obtain the title compound (8.4 g, yield 51.5%) as a gel.

$^1$H-NMR (200 MHz, CDCl$_3$): δ 7.47-7.55 (2H, m), 7.36 (1H, t, J=8.0 Hz), 7.27-7.30 (2H, m), 7.18-7.22 (3H, m), 7.13 (1H, dd, J=9.2, 2.8 Hz), 4.22 (2H, q, J=7.2 Hz), 4.01 (2H, t, J=6.2 Hz), 2.82 (2H, t, J=8.0 Hz), 2.13 (2H, m), 1.26 (3H, t, J=7.2 Hz).

(Step 3) Preparation of 2-benzoyl-3-{3'-(3-phenylpropyloxy)phenyl}-3-oxo-propionate ethyl ester [compound of chemical formula (XIV)]

3'-(3-Phenylpropyloxy)benzoylacetate ethyl ester (8.2 g, 25.2 mmol) obtained in (Step 2) of Example 5 and sodium hydride (1.1 g, 27.7 mmol) were added to methylene chloride (150 ml) and the reaction mixture was stirred for 1 hour at room temperature. Then, benzoyl chloride (3.65 g, 26.0 mmol) was added thereto and the mixture was further stirred for 2 hours at room temperature. The resultant was washed with purified water (200 ml), dried over anhydrous magnesium sulfate, concentrated, and the resulting residue was purified by silica gel column chromatography (ethyl acetate:hexane=1:8) to obtain the title compound (7.4 g, yield 68.5%) as a gel.

(Step 4) Preparation of 3-phenyl-6-(3-phenylpropyloxy)-1-oxo-1H-indene-2-carboxylate ethyl ester [compound of formula (II)]

2-Benzoyl-3-{3'-(3-phenylpropyloxy)phenyl}-3-oxo-propionate ethyl ester (6.4 g, 14.8 mmol) obtained in (Step 3) of Example 5 and methane sulfonic acid (15 g) were dissolved in methylene chloride (150 my) and the mixture was stirred for 2 hours at room temperature. Then, additional methylene chloride (150 ml) and saturated ammonium chloride (200 ml) were added thereto and the mixture was further stirred for 30 min. The extracted methylene chloride layer was dried over anhydrous magnesium sulfate, concentrated, and the resulting residue was purified by silica gel column chromatography (ethyl acetate:hexane=1:5) to obtain the title compound (3.4 g, yield 55.5%) as a gel.

$^1$H-NMR (200 MHz, CDCl$_3$): δ 7.51 (5H, s), 7.17-7.29 (6H, m), 7.06 (1H, d, J=8.1 Hz), 6.80 (1H, dd, J=8.1, 2.4 Hz), 4.18 (2H, q, J=7.1 Hz), 4.01° (2H, t, J=6.3 Hz), 2.81 (2H, t, J=7.3 Hz), 2.12-2.16 (2H, m), 1.16 (3H, t, J=7.1 Hz).

(Step 5) Preparation of 1-(trans-methylimino-N-oxy)-6-(3-phenyl propyloxy)-3-phenyl-1H-indene-2-carboxylate ethyl ester [No. 9 compound of Table (IX)] (reaction scheme (I))

3-Phenyl-6-(3-phenylpropyloxy)-1-oxo-1H-indene-2-carboxylate ethyl ester (2.0 g) obtained in (Step 4) of Example 5 and N-methylhydroxyl amine.hydrochloric acid (2.0 g) were dissolved in ethanol (30 ml). 2,6-Lutidine (2.4 g) was added thereto and the mixture was stirred for 60 hours. Then, the reaction mixture was concentrated, extracted with water (100 ml) and ethyl acetate (100 ml), washed three times with water. The extract was dried over anhydrous magnesium sulfate, concentrated, and the resulting residue was purified by silica gel column chromatography (ethyl acetate:hexane=1:4) to obtain the title compound (120 mg, yield 5.6%, mp 95-97° C.) as a gel.

Preparation of Compound of Formula 1 According to Reaction Scheme (V)

Example 6

Preparation of 1-(trans-methylimino-N-oxy)-3-phenyl-6-(3-phenylpropoxy)-1H-indene-2-carbonitrile [No. 75 compound of Table 1]

(Step 1) Preparation of 3-phenyl-6-(3-phenylpropoxy)indene-1-one[compound of formula (XV)]

3-Phenyl-1-[3-(3-phenylpropoxy)phenyl]propenone (20 g, 58.406 mmol) and polyphosphonic acid (200 g) were mixed and stirred for 6 hours at 45° C. The mixture was washed with water and extracted with ethyl acetate. The extract was dried over anhydrous magnesium sulfate, concentrated, and the resulting residue was purified by column chromatography (ethyl acetate:hexane=1:5) to obtain 3-phenyl-6-(3-phenylpropoxy)indane-1-one (17.9 g, yield 81%) as a white solid.

$^1$H NMR (300 MHz, CDCl$_3$): δ 7.36-7.09 (m, 13H), 4.52 (dd, J=7.8, 3.6 Hz, 1H), 4.01 (t, J=6.3 Hz, 2H), 3.25 (dd, J=19.3, 7.7 Hz, 1H), 2.81 (t, J=7.1 Hz, 2H), 2.68 (dd, J=19.3, 3.6 Hz, 1H), 2.14 (m, 2H).

(Step 2) Preparation of 2-bromo-3-phenyl-6-(3-phenylpropoxy)indane-1-one [compound of formula (XVI)]

3-Phenyl-6-(3-phenylpropoxy)indene-1-one (200 mg, 0.586 mmol) was dissolved in carbon tetrachloride, and N-bromosuccinimide (313 mg, 1.75 mmol) and 2,2'-azobisisobutyronitrile (9.7 mg) were added thereto. Then, the mixture was refluxed for 1 hour under a 375 W tungsten lamp. After the reaction was completed, saturated sodium chloride was added thereto and extracted with dichloromethane. The extract was dried over anhydrous magnesium sulfate, concentrated, and the resulting residue was purified by column chromatography (ethyl acetate:hexane=1:5) to obtain title compound (147 mg, yield 60%) as a red solid.

¹H NMR (300 MHz, CDCl₃): δ 7.69-7.16 (m, 11H), 7.02 (d, J=8.2 Hz, 1H), 6.74 (dd, J=8.2, 2.3 Hz, 1H), 3.97 (t, J=6.4 Hz, 2H), 2.81 (t, J=6.3 Hz, 2H), 2.11 (m, 2H).

(Step 3) Preparation of 1-oxo-3-phenyl-6-(3-phenylpropoxy)-1H-indene-2-carbonitrile [compound of formula (II)]

2-Bromo-3-phenyl-6-(3-phenylpropoxy)indene-1-one (1.0 g, 2.3 mmol) was dissolved in N,N-dimethylformamide (10 ml). Copper (I) cyanide (617 mg, 6.9 mmol) was added thereto and the mixture was stirred for 3 hours at 150° C. The mixture was cooled, and saturated ammonium chloride was added thereto. The organic layer was extracted with ethyl acetate, dried over anhydrous magnesium sulfate, concentrated, and the resulting residue was purified by column chromatography (ethyl acetate:hexane=1:3) to obtain the title compound (700 mg, yield 80%) as a red solid.

¹H NMR (200 MHz, CDCl₃): δ 7.83-7.18 (m, 12H), 6.89 (dd, J=8.2, J=2.3 Hz, 1H), 4.02 (t, J=6.5 Hz, 2H), 2.81 (t, J=6.3 Hz, 2H), 2.13 (m, 2H).

(Step 4) Preparation of 1-hydroxyimino-3-phenyl-6-(3-phenyl propoxy)-1H-indene-2-carbonitrile (cis, trans compound) [compound of formula (III)] (reaction scheme (I))

1-Oxo-3-phenyl-6-(3-phenylpropoxy)-1H-indene-2-carbonitrile (200 mg, 0.547 mmol) was dissolved in ethanol. Hydroxy amine.hydrochloric acid (114 mg, 1.64 mmol) and pyridine (173 mg, 2.18 mmol) were added thereto and the mixture was stirred for 4 hours at 70° C. The organic layer extracted with ethyl acetate was washed with distilled water, dried over anhydrous magnesium sulfate, concentrated, and the resulting residue was purified by column chromatography (ethyl acetate:hexane=1:2) to obtain trails 1-hydroxy imino-3-phenyl-6-(3-phenylpropyloxy)-1H-indene-2-carbonitrile (95 mg, yield 45%) as a red solid, ¹H NMR (300 MHz, CDCl₃): δ 9.21 (brs, 1H), 7.94 (d, J=2.3 Hz, 1H), 7.74-7.71 (m, 2H), 7.56-7.54 (m, 3H), 7.43 (d, J=8.4 Hz, 1H), 7.32-7.20 (m, 5H), 6.96 (dd, J=8.4, 2.3 Hz, 1H), 4.05 (t, J=6.3 Hz, 2H), 2.83 (t, J=6.3 Hz, 2H), 2.14 (m, 2H);

and cis-isomer (5 mg, yield 2%) as a yellow solid.

¹H NMR (300 MHz, CDCl₃): δ 9.71 (brs, 1H), 7.96 (d, J=2.3 Hz, 1H), 7.74-7.71 (m, 2H), 7.56-7.54 (m, 3H), 7.43 (d, J=8.3 Hz, 1H), 7.36-7.20 (m, 5H), 6.94 (dd, J=8.3, 2.3 Hz, 1H), 4.03 (t, J=6.3 Hz, 2H), 2.81 (t, J=6.3 Hz, 2H), 2.13 (m, 2H).

(Step 5) Preparation of 1-(trans-methylimino-N-oxy)-3-phenyl-6-(3-phenylpropoxy)-1H-indene-2-carbonitrile [No. 75 compound of Table 1] (reaction scheme (I))

Trans-1-hydroxyimino-3-phenyl-6-(3-phenylpropoxy)-1H-indene-2-carbonitrile (90 mg, 0.23 mmol) was dissolved in N,N-dimethylformamide. Methyl iodide (134 mg, 0.94 mmol) and potassium carbonate (98 mg, 0.71 mmol) were added thereto and the mixture was stirred for 10 min at room temperature. After the reaction was completed, the reaction mixture was cooled, and saturated ammonium chloride was added thereto. The organic layer extracted with ethyl acetate was dried over anhydrous magnesium sulfate, concentrated, and the resulting residue was purified by column chromatography (ethyl acetate:hexane=1:2) to obtain the title compound (11 mg, yield 12%) as a red solid, ¹H NMR (300 MHz, CDCl₃): δ 8.29 (d, J=2.3 Hz, 1H), 7.72-7.55 (m, 5H), 7.44 (d, J=8.3 Hz, 1H), 7.31-7.17 (m, 5H), 6.96 (dd, J=8.3, 2.3 Hz, 1H), 4.47 (s, 3H), 4.08 (t, J=6.2 Hz, 2H), 2.83 (t, J=6.2 Hz, 2H), 2.12 (m, 2H);

and trans-1-methoxyimino-3-phenyl-6-(3-phenylpropoxy)-1H-indene-2-carbonitrile (69 mg, yield 74%).

Preparation of Compound of Formula (I) According to Reaction Scheme (VII)

Example 7

Preparation of 1-(trans-methylimino-N-oxy)-6-(morpholine-4-ylmethyl)-3-phenyl-1H-indene-2-carboxylic ethyl ester [No. 77 compound of Table 1]

(Step 1) Preparation of 3-oxo-3-m-tolylpropionate ethyl ester

Sodium hydride (3.1 g, 77.1 mmol) and diethyl carbonate were combined with 3-methylacetophenone (4.5 g, 33.54 mmol). The mixture was stirred for 2 hours at 80° C. After the reaction was completed, ice water and acetic acid were added thereto. Then, the mixture was extracted with ethyl acetate/saturated sodium chloride. The extract was dried over anhydrous magnesium sulfate, concentrated, and the resulting residue was purified by column chromatography to obtain 3-oxo-3-m-tolylpropionate ethyl ester (5.8 g, yield 84%).

¹H NMR (200 MHz, CDCl₃): δ 7.83-7.63 (m, 2H), 7.42-7.28 (m, 2H), 4.27-4.18 (m, 2H), 3.97 (s, 2H), 2.40 (s, 3H), 1.36-1.23 (m, 3H).

(Step 2) Preparation of 2-(3-methyl benzoyl)-3-phenylacrylate ethyl ester

3-Oxo-3-m-tolylpropionate ethyl ester (1 g, 4.84 mmol) was dissolved in benzene, and benzaldehyde (0.51 g, 4.84 mmol), acetic acid (0.15 g, 2.49 mmol) and piperidine (0.06 g, 0.8 mmol) were added thereto. The mixture was refluxed for 4 hours. After the reaction was completed, the organic layer extracted with ethyl acetate/saturated sodium chloride/sodium bicarbonate was dried over anhydrous magnesium sulfate, concentrated, and the resulting residue was purified by column chromatography to obtain 2-(3-methylbenzoyl)-3-phenylacrylate ethyl ester (1 g, yield 70%).

¹H NMR (200 MHz, CDCl₃): δ 7.98 (s, 1H), 7.86-7.73 (m, 2H), 7.35-7.21 (m, 7H), 4.26-4.19 (m, 2H), 2.39 (s, 3H), 1.20-1.16 (m, 3H).

(Step 3) Preparation of 5-methyl-3-oxo-1-phenylindane-2-carboxylate ethyl ester 2-(3-Methylbenzoyl)-3-phenylacrylate ethyl ester (1 g, 3.39 mmol) was dissolved in dichloromethane. Methanesulfonic acid (5.22 g, 54.35 mmol) was added thereto and the mixture was stirred for 3 hours at room temperature. After the reaction was completed, the mixture was cooled to 0° C. followed by neutralizing with sodium bicarbonate. Then, the separated organic layer extracted with dichloromethane was dried over anhydrous magnesium sulfate, concentrated, and the resulting residue was purified by column chromatography (ethyl acetate:hexane=1:9) to obtain 5-methyl-3-oxo-1-phenyl-indene-2-carboxylate ethyl ester (273 mg, yield 27%).

¹H NMR (200 MHz, CDCl₃): δ 7.73-7.61 (m, 1H), 7.48-7.04 (m, 7H), 4.98-4.94 (m, 1H), 4.29-4.22 (m, 2H), 3.67-3.60 (m, 1H), 2.41 (s, 3H) 1.33-1.13 (m, 3H).

(Step 4) Preparation of 6-methyl-1-oxo-3-phenyl-1H-indene-2-carboxylate ethyl ester Phenylselenyl chloride (72 mg, 0.37 mmol) was dissolved in dichloromethane. The mixture was cooled to 0° C., combined with pyridine (32 mg, 1.2 mmol), and stirred for about 20 min. The mixture containing 5-methyl-3-oxo-1-phenylindane-2-carboxyl acid ethyl ester (100 mg, 0.34 mmol) dissolved in methane was further added followed by stirring for 2 hours at room temperature. After the reaction was completed, 10% hydrochloric acid (5 mg) was added into the mixture prior to cooling to 0° C. After adding 30% hydrogen peroxide (1 ml) and water (5 ml), the separated organic layer extracted with dichloromethane was dried over anhydrous magnesium sulfate, concentrated, and the resulting residue was purified by column chromatography (ethyl acetate:hexane=1:7) to obtain 6-methyl-1-oxo-3-phenyl-1H-indene-2-carboxylate ethyl ester (51 mg, yield 51%).

$^1$H NMR (200 MHz, CDCl$_3$): δ 7.51-7.04 (m, 8H), 4.24-4.12 (m, 2H), 2.39 (s, 3H), 1.25-1.12 (m, 3H).

(Step 5) Preparation of 6-bromomethyl-1-oxo-3-phenyl-1H-indene-2-carboxylate ethyl ester [compound of formula (XIX)]

6-Methyl-1-oxo-3-phenyl-1H-indene-2-carboxylate ethyl ester (3 g, 10.3 mmol) was dissolved in carbon tetrachloride, and N-bromosuccinimide (2 g, 11.4 mmol) and 2,2'-azobisisobutyronitrile (500 mg, 3.09 mmol) were added thereto. Then, the mixture was refluxed for 3 hours under a 375 W tungsten lamp. After the reaction is completed, the organic layer was extracted with dichloromethane/saturated sodium chloride, dried over anhydrous magnesium sulfate, concentrated, and the resulting residue was purified by column chromatography to obtain 6-bromomethyl-1-oxo-3-phenyl-1H-indene-2-carboxylate ethyl ester (1.4 g, yield 36.7%) as yellow oil.

$^1$H NMR (200 MHz, CDCl$_3$): δ 7.79-7.16 (m, 8H), 4.50 (s, 2H), 4.26 (q, J=7.1 Hz, 2H), 1.16 (t, J=7.1 Hz, 3H).

(Step 6) Preparation of 6-(morpholine-4-ylmethyl)-1-oxo-3-phenyl-1H-indene-2-carboxylate ethyl ester [compound of formula (XIX)]

6-Bromomethyl-1-oxo-3-phenyl-1H-indene-2-carboxylate ethyl ester (1.1 g, 2.96 mmol) was dissolved in N,N-dimethylformamide. Pyridine (264 μl, 3.26 mmol) and morpholine (284 μl, 3.26 mmol) were added thereto and the mixture was stirred for 2 hours. After the reaction was completed, the organic layer was extracted with ethyl acetate/ammonium chloride/saturated sodium chloride, dried over anhydrous magnesium sulfate, concentrated, and the resulting residue was purified by column chromatography to obtain 180 mg of 6-(morpholine-4-yl methyl)-1-oxo-3-phenyl-1H-indene-2-carboxylate ethyl ester (180 mg, yield 16.1%) as red oil.

$^1$H NMR (200 MHz, CDCl$_3$): δ 7.61-7.11 (m, 8H), 4.19 (q, J=7.1 Hz, 2H), 3.70 (t, J=4.8 Hz, 4H), 3.51 (s, 2H), 2.44 (t, J=4.8 Hz, 4H), 1.15 (t, J=7.1 Hz, 3H).

(Step 7) Preparation of 1-(trans-methylimino-N-oxy)-6-(morpholine-4-ylmethyl)-3-phenyl-1H-indene-2-carboxylate ethyl ester [No. 77 compound of Table 1] (reaction scheme (I))

6-(Morpholine-4-ylmethyl)-1-oxo-3-phenyl-1H-indene-2-carboxylate ethyl ester (110 mg, 0.29 mmol) was dissolved in N-methylhydroxyl amine.hydrochloride (73 mg, 0.87 mmol), and 2,6-lutidine (34 μl, 0.87 mmol) were added thereto. The mixture was reacted for 3 days at 70° C. After the reaction was completed, ethanol was half concentrated, and the organic layer was extracted with ethyl acetate/saturated sodium chloride. The extract was dried over anhydrous magnesium sulfate, concentrated, and the resulting residue was purified by column chromatography to obtain 1-(trans-methylimino-N-oxy)-6-(morpholine-4-ylmethyl)-3-phenyl-1H-indene-2-carboxylate ethyl ester (5.3 mg, yield 4.5%).

Preparation of Compound of Chemical Formula (I) According to Reaction Scheme (II)

Example 8

Preparation of 1-(trans-methylimino-N-oxy)-6-(3-phenyl-propyloxy-3-phenyl-1H-indene-2-carboxylate cyclohexyl amide [No. 39 compound of Table 1]

(Step 1) Preparation of 3-phenyl-6-(3-phenylpropyloxy)-1-oxo-1H-indene-2-carboxylate methyl ester 3-Phenyl-6-(3-phenylpropyloxy)-1-oxo-1H-indene-2-carboxylate ethyl ester (1.65 g, 4.0 mmol) prepared in (Step 5) of Example 1 was dissolved in methanol (160 ml) and p-toluene sulfonic acid (228 mg, 1.2 mmol) was added thereto. The mixture was reacted for 1 hour at 70° C., and then washed with brine. The organic layer was extracted with ethyl acetate, dried over anhydrous sulfonate sulfate, concentrated, and the resulting residue was purified by silica gel column chromatography (ethyl acetate:hexane=1:9) to obtain the title compound (yield 75.3%) as a red solid.

$^1$H NMR (200 MHz, CDCl$_3$): δ 7.43 (s, 5H), 7.27-6.77 (m, 7H), 3.92 (t, J=6.3 Hz, 2H), 3.65 (s, 3H), 2.73 (t, J=7.1 Hz, 2H), 2.03 (p, J=6.5 Hz, 2H).

(Step 2) Preparation of 3-phenyl-6-(3-phenylpropyloxy)-1-oxo-1H-indene-2-carboxylate Tribromoborone-dimethyl sulfide complex (1.94 ml, 9.03 mmol) was suspended in 1,2-dichloroethane (15 ml), and 3-phenyl-6-(3-phenylpropyloxy)-1-oxo-1H-indene-2-carboxylate methyl ester (1.2 g, 3.0 mmol) dissolved in 1,2-dichloroethane (10 ml) was added thereto. The mixture was stirred for 2 hours at 90° C. followed by cooling to room temperature. After adding sodium bicarbonate, the resulting solution was acidified to pH 2.0 with 6N-hydrochloric acid solution, and then washed with brine. The organic layer was extracted with dichloromethane, dried over anhydrous sulfonate sulfate, concentrated, and the resulting residue was purified by silica gel column chromatography (ethyl acetate:hexane=3:7~5:5) to obtain the title compound (yield 75.3%) as a red solid.

$^1$H NMR (200 MHz, CDCl$_3$): δ 7.69-6.82 (m, 13H), 4.03 (t, J=6.3 Hz, 2H), 2.83 (t, J=7.1 Hz, 2H), 2.14 (p, J=6.5 Hz, 2H);

EI-MS m/z (relative intensity): 381 (M-3, 6.92), 148 (7.91), 117 (6.47), 64 (7.69), 44 (100).

(Step 3) Preparation of 3-phenyl-6-(3-phenylpropyloxy)-1-oxo-1H-indene-2-carboxylate cyclohexylamide 3-Phenyl-6-(3-phenylpropyloxy)-1-oxo-1H-indene-2-carboxylate (200 mg, 0.52 mmol) was dissolved in dichloromethane (10 ml). Triethylamine (240 μl, 1.72 mmol) and cyclohexylamine (59 μl, 0.52 mmol) were added thereto at 10° C. Then, after adding bis(2-oxo-3-oxazolidinyl)phosphinic chloride (137 mg, 0.52 mmol), the reaction mixture was stirred for about 20 min at room temperature followed by additional 1 hour at 10° C. After the water was added thereto to complete the reaction, pH was adjusted to 1~1.5 with 4N hydrochloric acid. The mixture was washed with brine, and extracted with dichloromethane. The extract was dried over anhydrous sulfonate sulfate, concentrated, and the resulting residue was purified by column chromatography (ethyl acetate:hexane=1:9~2:8) to obtain the title compound (yield 59.8%) as a red solid.

$^1$H NMR (200 MHz, CDCl$_3$): δ 7.68-6.80 (m, 13H), 3.98 (t, J=6.3 Hz, 2H), 3.87 (m, 1H), 2.81 (t, J=7.1 Hz, 2H), 2.11 (p, J=6.5 Hz, 2H), 1.80-1.20 (m, 10H);

EI-MS m/z (relative intensity): 467 (M$^+$, 4.81), 382 (14.64), 248 (53.46), 164 (13.54), 90 (100).

(Step 4) Preparation of 1-(trans-methylimino-N-oxy)-6-(3-phenylpropyloxy)-3-phenyl-1H-indene-2-carboxylate cyclohexyl amide [No. 39 compound of Table 1] (reaction scheme (I))

3-Phenyl-6-(3-phenylpropyloxy)-1-oxo-1H-indene-2-carboxylate cyclohexylamide (50 mg, 0.11 mmol) was dissolved in ethanol and N-methyl hydroxyl amine.hydrochloride (27 mg, 0.33 mmol), and 2,6-lutidine (38 µl, 0.33 mmol) were added thereto. The mixture was reacted for 3 days at 70° C. After the reaction was completed, ethanol was half concentrated, and the organic layer was extracted with ethyl acetate/saturated sodium chloride. The extract was dried over anhydrous magnesium sulfate, concentrated, and the resulting residue was purified by column chromatography to obtain 1-(trans-methyl imino-N-oxy)-6-(3-phenylpropyloxy)-3-phenyl-1H-indene-2-carboxylate cyclohexyl amide (13.1 mg, yield 24%) as a red solid.

Example 9

Preparation of 1-(trans-methylimino-N-oxy)-3-phenyl-5-(2-pyridine-2-ylethoxy)-1H-indene-2-carboxylate isopropyl amide [No. 99 compound of Table 1]

(Step 1) Preparation of acetate 2-isopropyl carbamoyl-1-oxo-3-phenyl-1H-indene-5-yl ester Phenylselenyl chloride (5.4 g, 28.2 mmol) was dissolved in dichloromethane (CH$_2$Cl$_2$, 100 ml). The mixture was cooled with ice water, and pyridine (2.45 g, 31 mmol) was added dropwise thereto followed by stirring for about 20 min while maintaining the temperature. 2-Isopropyl carbamoyl-1-oxo-3-phenyl indene-5-yl ester acetate (9.0 g, 25.6 mmol) dissolved in dichloromethane (150 ml) was added dropwise thereto and the mixture was stirred for 3 hours at room temperature. After the reaction was completed, 2N-hydrochloric acid was added into the mixture prior to cooling to 0° C. After adding excess 30% hydrogen peroxide (H$_2$O$_2$) and sodium bicarbonate, the separated organic layer was extracted with dichloromethane and concentrated. The resulting solid residue was dissolved in excess ethyl acetate (300 ml), and washed with diluted hydrochloric acid. The extract was dried over anhydrous magnesium sulfate, concentrated, and the resulting residue was recrystallized in ethyl acetate to obtain the title compound (7.6 g, yield 85%) as a yellow solid.

$^1$H NMR (300 MHz, CDCl$_3$): δ 7.74 (brd, J=7.5 Hz, 1H), 7.57-7.48 (m, 6H), 7.08 (dd, J=7.8, 1.8 Hz, 1H), 6.83 (d, J=1.8 Hz, 1H), 4.16 (m, 1H), 2.27 (s, 3H), 1.20 (d, J=6.6 Hz, 6H).

Mass spectrum m/e (relative intensity): 349 (M$^+$, 3), 291 (3), 249 (6), 163 (8), 58 (48), 43 (100).

(Step 2) Preparation of 5-hydroxy-1-(trans-methylimino-N-oxy)-3-phenyl-1H-indene-2-carboxylate isopropyl amide 2-Isopropylcarbamoyl-1-oxo-3-phenyl-1H-indene-5-yl ester acetate (6.26 g, 17.9 mmol) was dissolved in ethanol (200 ml). N-methylhydroxylamine hydrochloride (4.52 g, 53.7 mmol) and 2,6-lutidine (5.75 g, 53.7 mmol) were added thereto and the mixture was stirred for 40 hours at 75° C. in a pressure reactor. Ethanol was removed under reduced pressure, and the resulting residue was extracted with ethyl acetate. After washing with diluted hydrochloric acid solution, the organic layer was dried over anhydrous magnesium sulfate, concentrated, and the resulting residue was purified by column chromatography to obtain the title compound (3.1 g, yield 51%).

$^1$H NMR (300 MHz, DMSO-d$_6$): δ 9.91 (s, 1H), 8.54 (d, J=7.9 Hz, 1H), 8.29 (d, J=8.1 Hz, 1H), 7.50-7.43 (m, 5H), 6.72-6.69 (m, 2H), 4.01 (s, 3H), 3.89 (m, 1H), 0.93 (d, J=6.6 Hz, 6H).

(Step 3) Preparation of 1-(trans-methylimino-N-oxy)-3-phenyl-5-(2-pyridine-2-ylethoxy)-1H-indene-2-carboxylate isopropyl amide 5-Hydroxy-1-(trans-methylimino-N-oxy)-3-phenyl-1H-indene-2-carboxylate isopropyl amide (3.77 g, 11.2 mmol) was dissolved in tetrahydrofuran:benzene (300 ml:100 ml). Then, 2-(2-pyridyl)ethanol (1.93 g, 15.7 mmol) and triphenylphosphine (4.13 g, 15.57 mmol) were added thereto. Diisopropyl azodicarboxylate (3.14 g, 15.7 mmol) was added dropwise to the mixture followed by stirring for 2 hours at room temperature when the temperature was adjusted to 0° C. The mixture was washed with brine and extracted with ethyl acetate. The extract was dried over anhydrous magnesium sulfate, concentrated, and the resulting residue was purified by column chromatography to obtain the title compound (3.36 g, yield 68%) as a yellow solid.

Isomer Transformation Between Cis and Trans

Example 10

Transformation of 1-(trans-methylimino-N-oxy)-6-(2-morpholine-4-ylethoxy)-3-phenyl-1H-indene-2-carboxylate ethyl ester [No. 33 compound of Table 1] to cis-isomer (10-1) Base Reaction 50 mg of 1-(trans-methylimino-N-oxy)-6-(2-morpholine-4-ylethoxy)-3-phenyl-1H-indene-2-carboxylate ethyl ester was dissolved in tetrahydrofuran:methanol (10 ml:10 ml) and 3 equivalents of lithium hydroxide was added thereto. After reacting for 2 days at room temperature, the concentrated mixture was washed with saturated sodium chloride and extracted with dichloromethane. The organic layer was dried over anhydrous magnesium sulfate, the concentrated, and the resulting residue was purified by column chromatography to obtain 1-(cis-methylimino-N-oxy)-6-(2-morpholine-4-ylethoxy)-3-phenyl-1H-indene-2-carboxylate ethyl ester (yield 10%).

(10-2) Photochemical Reaction 50 mg of 1-(trans-methylimino-N-oxy)-6-(2-morpholine-4-ylethoxy)-3-phenyl-1H-indene-2-carboxylate ethyl ester was dissolved in ethanol (30 ml) and excess lithium chloride was added thereto, followed by subjecting the UV irradiation at 250 nm. After reacting for 12 hours, the solution was analyzed by HPLC to determine that 25% of 1-(cis-methylimino-N-oxy)-6-(2-morpholine-4-ylethoxy)-3-phenyl-1H-indene-2-carboxylate ethyl ester was produced.

Formulation Example 1

Preparation of Syrup

A syrup containing the hydrochloride of the compound of Example 2 was prepared using the ingredients shown in Table 2 by dissolving hydrochloride of 1-(methyl imino-N-oxy)-6-(2-morpholine-4-yl ethoxy)-3-phenyl-1H-indene-2-carboxylate ethyl ester, saccharine, and sugar in warm water, cooling, and adding other ingredients thereto to a volume of 100 ml.

TABLE 2

| Ingredients | Content |
| --- | --- |
| Hydrochloride of 1-(methylimino-N-oxy)-6-(2-morpholine-4-yl-ethoxy)-3-phenyl-1H-indene-2-carboxylate ethyl ester | 2 g |
| Saccharine | 0.8 g |
| Sugar | 25.4 g |
| Glycerin | 8.0 g |
| Flavoring | 0.04 g |
| Ethanol | 4.0 g |
| Sorbic Acid | 0.4 g |
| Distilled Water | Fixed amount |

Formulation Example 2

Preparation of a Tablet

A tablet containing the hydrochloride of the compound of Example 2 was prepared with the ingredients shown in Table 3 by mixing hydrochloride of 1-(methylimino-N-oxy)-6-(2-morpholine-4-yl-ethoxy)-3-phenyl-1H-indene-2-carboxylate ethyl ester with lactose, potato starch and colloidal silica and adding a 10% gelatin solution thereto. Then the mixture was crushed, sieved through a 14 mesh and dried. Finally the remaining ingredients were added thereto and tableting was performed.

TABLE 3

| Ingredients | Content |
| --- | --- |
| Hydrochloride of 1-(methylimino-N-oxy)-6-(2-morpholine-4-yl-ethoxy)-3-phenyl-1H-indene-2-carboxylate ethyl ester | 250 g |
| Lactose | 175.9 g |
| Potato Starch | 180 g |
| Colloidal Silica | 32 g |
| 10% gelatin Solution | 25 g |
| Potato Starch | 160 g |
| Talc | 50 g |
| Magneisum Stearate | 5 g |

Formulation Example 3

Preparation of an Injection Liquid

The hydrochloride of 1-(methylimino-N-oxy)-6-(2-morpholine-4-yl-ethoxy)-3-phenyl-1H-indene-2-carboxylate ethyl ester, sodium chloride and ascorbic acid were dissolved in distilled water in amounts as shown in Table 4 and sterilized.

TABLE 4

| Ingredients | Content |
| --- | --- |
| Hydrochloride of 1-methylimino-N-oxy)-6-(2-morpholine-4-yl-ethoxy)-3-phenyl-1H-indene-2-carboxylate ethyl ester | 1 g |
| Sodium Chloride | 0.6 g |
| Ascorbic Acid | 0.1 g |
| Distilled Water | Fixed amount |

Test Example 1

PPARγ Activation Test

The activity for PPARγ activation was examined as follows.

The vector fused with the ligand binding domain of a human PPARγ gene and the DNA binding site of a yeast GAL-4 gene, and luciferase reporter vector were simultaneously transfected in NIH/3T3 cell. The cells were cultured for 24 hrs. The solution containing the cells at a concentration of $2 \times 10^4$ cells/well was placed on a 96-well plate. Then, each of the test compounds of the present invention or the control group without test compounds was added thereto. After incubating for 24 hrs, the cells were subjected to lysis. The luciferase activity of the resultant was then measured, and the activation activity of the test compound was expressed as $EC_{50}$ (the concentration at which 50% of the maximum activation was observed) to compute the activation intensities of the test compounds and the comparative compound, rosiglitazone, relative to PPARγ. The results are shown in Table 5. Rosiglitazone having the formula (XX) was prepared according to the method described in *J. Med. Chem.* 1994, 37, 3997.

TABLE 5

| No. of Compound of Table 1 | $EC_{50}$(nM) |
| --- | --- |
| 8 | 25 |
| 9 | 40 |
| 10 | 200 |
| 11 | 40 |
| 13 | 150 |
| 15 | 150 |
| 25 | 50 |
| 33 | 15 |
| 34 | 70 |
| 36 | 28 |
| 38 | 170 |
| 39 | 45 |
| 41 | 12 |
| 42 | 80 |
| 43 | 80 |
| 45 | 15 |
| 48 | 10 |
| 50 | 200 |
| 68 | 10 |
| 73 | 110 |
| 75 | 95 |
| 77 | 170 |
| 78 | 15 |
| 79 | 20 |
| 80 | 100 |
| 81 | 45 |

TABLE 5-continued

| No. of Compound of Table 1 | EC$_{50}$(nM) |
|---|---|
| 94 | 80 |
| Rosiglitazone | 320 |

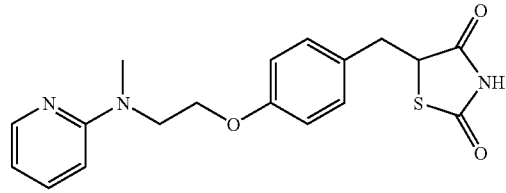
(XX)

As shown in Table 5, the inventive compounds exhibited superior PPARγ activation activities over the comparative compound, rosiglitazone.

Test Example 2

Effectiveness in Lowering Blood Glucose Level

The effectiveness in lowering blood glucose levels of the inventive compound was examined using ob/ob mice (male, 8-9 weeks old), a type 2 diabetes model animal which expresses signs of hyperglycemia and hyperinsulinemia, and bred at in-house facilities of Korea Research Institute of Chemical Technology.

The hydrochloric acid salt of 1-hydroxy-6-(2-morpholine-4-yl-ethoxy)-1,3-diphenyl-1H-indene-2-carboxylic acid ethyl ester prepared in Example 8 was suspended in saline/ 0.2% Tween 80. The resulting solution was intraperitoneally administered to the mice at a dose of 50 mg/kg, once a day for 5 days, or orally administered to the mice, at a dose of 100 mg/kg, twice a day for 14 days. Days 1, 3 and 5 were selected for intraperitoneal administration, and days 5, 10 and 14, for oral administration, to collect blood samples for measuring the blood glucose levels. The extent of inhibition of the inventive compound relative to the control (saline-0.2% Tween 80 in the absence of the compound) is shown in Table 6. Upon the completion of the oral administration for 14 days, the mice were fasted for 16 hrs to perform OGTT (Oral Glucose Tolerance Test) to determine the changes in insulin sensitivity induced by the oral administration. After administrating glucose to the mice at a dose of 2 g/kg orally, blood samples were collected at 0, 15, 30 60 and 120 minutes to measure blood glucose levels. The change in the total amount of blood glucose was computed over the 120-minute period to assess the extent of enhancing glucose clearance rates by compound treatment. The results are shown in Table 6, as % inhibition of total amount of blood glucose by the compound treatment relative to the untreated group.

TABLE 6

| Classification | % Inhibition |
|---|---|
| Intraperitoneal Administration (50 mg/kg/day) | 32.0 |
| Oral Administration (100 mg/kg/day) | 23.7 |
| Oral Glucose Tolerance Test (Blood Glucose) | 10.2 |

Moreover, C57/BL6J mice (male, 4 weeks old) which received high fat diet (60% fat) for 10-11 weeks and showed hyperglycemia and insulin resistance were chosen to carry out similar experiments (oral administration for 14 days but once a day) as described above. The extents of suppression of blood glucose and insulin levels were measured as mentioned above. The results are shown in Table 7. To check possible adverse side effects caused by the administration of the compound, the weight, heart weight and liver weight of each mouse were measured. GPT and GOT values were also calculated by employing a kit available in the market. The results are listed in Table 8.

TABLE 7

| Classification | % Inhibition (%) |
|---|---|
| Blood glucose concentration | 30.0 |
| Blood insulin concentration | 44.6 |
| Oral Glucose Tolerance Test | 23.8 (Glucose)/56.2 (Insulin) |

TABLE 8

| | Weight (g) | Heart Weight (g) | Liver Weight (g) | GPT/GOT (karmen) |
|---|---|---|---|---|
| Standard (High fat diet) | 38 ± 2.8 | 0.142 ± 0.006 | 1.56 ± 0.13 | 91 ± 32/ 67 ± 17 |
| Compound of the present invention | 35 ± 1.1 | 0.123 ± 0.007 | 1.06 ± 0.17 | 29 ± 3.2/ 39 ± 7.8 |
| Rosiglitazone | 39 ± 1.6 | 0.140 ± 0.009 | 1.56 ± 0.18 | 85 ± 12/ 70 ± 8.2 |

As shown in Tables 6, 7, and 8, the inventive compound has an excellent effect in lowering both blood glucose and insulin levels, when it is administered by either orally or intraperitoneally with no side effects such as weight gain, hepatotoxicity or cardiotoxicity.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

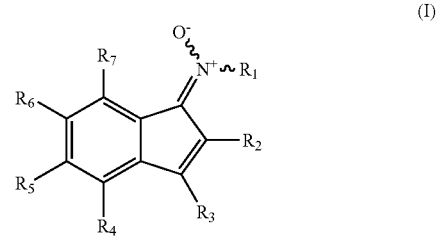
(I)

wherein,

R$_1$ is C$_{1-6}$ alkyl, C$_{1-6}$ alkenyl, or C$_{3-6}$ cycloalkyl, each of which is unsubstituted or substituted with one or more phenyl groups;

$R_2$ is H, CN, $CO_2R^a$, $CH_2CO_2R^a$, $CONR^bR^c$,

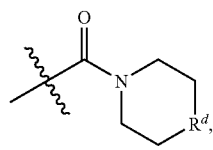

or phenyl;
$R_3$ is $C_{1-6}$ alkyl, $C_{3-6}$ cycloalkyl, naphthyl, phenyl,

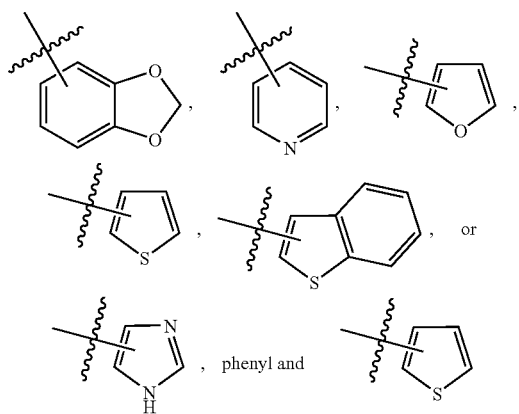

being each unsubstituted or substituted with one or more substituents selected from the group consisting of halogen, CN, $NH_2$, $NO_2$, $OR^a$, phenyloxy, $C_{1-6}$ alkyl, and $C_{3-6}$ cycloalkyl; and $R_4$, $R_5$, $R_6$, and $R_7$ are each independently H, OH, $OSO_2CH_3$, $O(CH_2)_mR^e$, $CH_2R^f$, $OCOCH_2OR^g$, $OCH_2CH_2OR^g$, $OCH_2CH=CHR^g$, or $R_5$ and $R_6$ together form $OCH_2O$;

in which $R^a$ is H, $C_{1-6}$ alkyl, or $C_{3-6}$ cycloalkyl, $C_{1-6}$ alkyl and $C_{3-6}$ cycloalkyl being each unsubstituted or substituted with one or more halogens;

$R^b$ and $R^c$ are each independently H, $C_{1-6}$ alkyl, or $C_{3-6}$ cycloalkyl;

$R^d$ is O, S, or $NR^a$;

$R^e$ is H, halogen, $C_{3-6}$ cycloalkyl, naphthyl,

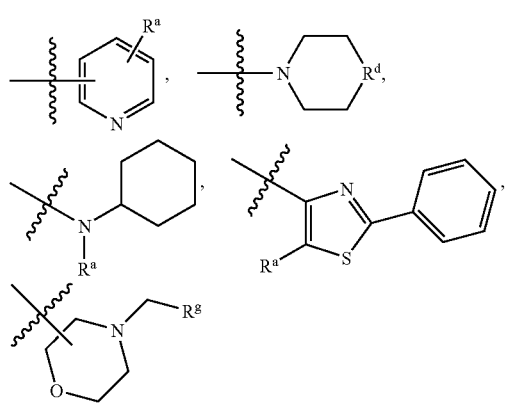

or phenyl, phenyl being unsubstituted or substituted with one or more substituents selected from the group consisting of halogen, CN, $NH_2$, $NO_2$, $OR^a$, $CF_3$, and $COOR^a$;

$R^f$ is $OCH_2CH_2R^g$ or

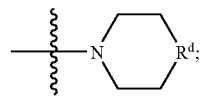

$R^g$ is phenyl, which is unsubstituted or substituted with one or more substituents selected from the group consisting of halogen, CN, $NH_2$, $NO_2$, and $OR^a$; and m is an integer in the range of 1 to 5.

2. The compound of claim 1, wherein $R_1$ is $C_{1-6}$ alkyl, which is unsubstituted or substituted with a phenyl group; $R_2$ is H, CN, $CO_2R^a$, $CH_2CO_2R^a$, $CONR^bR^c$, or phenyl; $R_3$ is $C_{1-6}$ alkyl, $C_{3-6}$ cycloalkyl, phenyl,

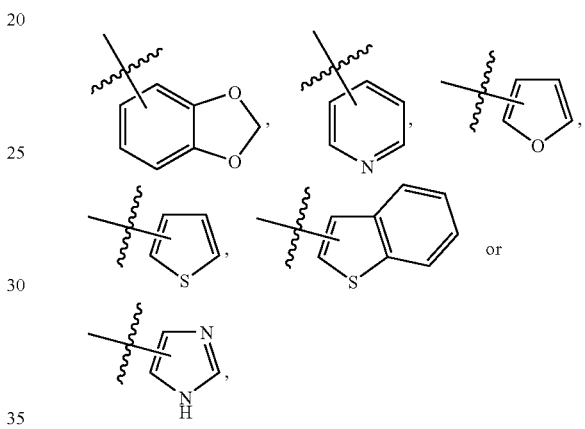

phenyl being unsubstituted or substituted with one or more substituents selected from the group consisting of halogen, $C_{1-6}$ alkyl, and $C_{3-6}$ cycloalkyl; $R_4$ and $R_7$ are H; $R_5$ and $R_6$ are each independently OH, $OSO_2CH_3$, $O(CH_2)_mR^e$, $CH_2R^f$, $OCOCH_2OR^g$, $OCH_2CH_2OR^g$, or $OCH_2CH=CHR^g$, or together form $OCH_2O$; $R^a$ is H or $C_{1-6}$ alkyl; $R^d$ is O or $NCH_3$; $R^e$ is H, halogen, $C_{3-6}$ cycloalkyl, naphthyl,

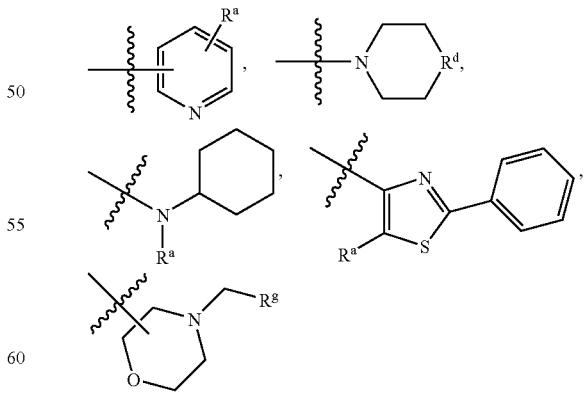

or phenyl, phenyl being unsubstituted or substituted with one or more substituents selected from the group consisting of halogen, OH, methoxy, $CF_3$, and $COOR^a$; $R^f$ is $OCH_2CH_2R^g$ or

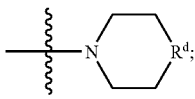

and R$^g$ is phenyl.

3. The compound of claim 2, wherein R$_1$ is CH$_3$; R$_2$ is H, CN, CO$_2$R$^a$, or CONR$^b$R$^c$; R$_3$ is C$_{1-6}$ alkyl, phenyl,

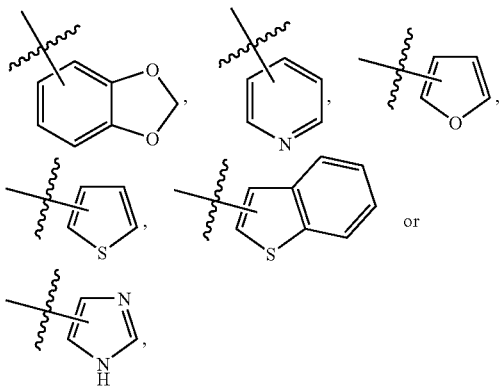

phenyl being unsubstituted or substituted with one or more halogens or C$_{1-6}$ alkyl groups; and R$_5$ and R$_6$ are each independently O(CH$_2$)$_m$R$^e$ or CH$_2$R$^f$, or together form OCH$_2$O.

4. A compound selected from the group consisting of:
1) 6-methoxy-1-(trans-methylimino-N-oxy)-3-phenyl-1H-indene-2-carboxylate ethyl ester
2) 1-(trans-isopropylimino-N-oxy)-6-methoxy-3-phenyl-1H-indene-2-carboxylate ethyl ester
3) 1-(trans-benzylimino-N-oxy)-6-methoxy-3-phenyl-1H-indene-2-carboxylate ethyl ester
4) 1-(trans-ethylimino-N-oxy)-6-methoxy-3-phenyl-1H-indene-2-carboxylate ethyl ester
5) 6-methoxy-1-(trans-phenylpropylimino-N-oxy)-3-phenyl-1H-indene-2-carboxylate ethyl ester
6) 6-methoxy-1-(trans-(2-methylbutenylimino)-N-oxy)-3-phenyl-1H-indene-2-carboxylate ethyl ester
7) 1-(trans-isobutylimino-N-oxy)-6-methoxy-3-phenyl-1H-indene-2-carboxylate ethyl ester
8) 1-(trans-methylimino-N-oxy)-6-(2-morphorline-4-ylethoxy)-3-phenyl-1H-indene-2-carboxylate ethyl ester
9) 1-(trans-methylimino-N-oxy)-3-phenyl-6-(3-phenylpropoxy)-1H-indene-2-carboxylate ethyl ester
10) 1-(trans-methylimino-N-oxy)-6-phenetyloxy-3-phenyl-1H-indene-2-carboxylate ethyl ester
11) 3-furan-3-yl-1-(trans-methylimino-N-oxy)-6-(3-phenylpropoxy)-1H-indene-2-carboxylate ethyl ester
12) 6-hydroxy-1-(trans-methylimino-N-oxy)-3-phenyl-1H-indene-2-carboxylate ethyl ester
13) 1-(cis-methylimino-N-oxy)-3-phenyl-6-(3-phenylpropoxy)-1H-indene-2-carboxylate ethyl ester
14) 3-(trans-methylimino-N-oxy)-1-phenyl-3H-indene-5-ol
15) 1-(trans-methylimino-N-oxy)-3-phenyl-6-(5-phenylpentyloxy)-1H-indene-2-carboxylate ethyl ester
16) 1-(cis-methylimino-N-oxy)-3-phenyl-6-(5-phenylpentyloxy)-1H-indene-2-carboxylate ethyl ester
17) 6-[2-(4-chlorophenoxy)acetoxy]-1-(trans-methylimino-N-oxy)-3-phenyl-1H-indene-2-carboxylate ethyl ester
18) 6-[2-(4-chlorophenoxy)ethoxy]-1-(trans-methylimino-N-oxy)-3-phenyl-1H-indene-2-carboxylate ethyl ester
19) 1-(trans-methylimino-N-oxy)-6-(naphthalene-2-ylmethoxy)-3-phenyl-1H-inden e-2-carboxylate ethyl ester
20) methyl-[3-phenyl-6-(3-phenylpropoxy)indene-1-ylidene]amine-N-oxide
21) 1-(trans-methylimino-N-oxy)-6-[2-(5-methyl-2-phenylthiazol-4-yl)ethoxy]-3-phenyl-1H-indene-2-carboxylate ethyl ester
22) 1-(trans-methylimino-N-oxy)-3-phenyl-6-(3-phenylpropoxy)-1H-indene-2-carboxylate ethyl ester
23) 6-[2-(4-hydroxyphenyl)ethoxy]-1-(trans-methylimino-N-oxy)-3-phenyl-1H-indene-2-carboxylate ethyl ester
24) 6-(2-adaman-1-ylethoxy)-1-(trans-methylimino-N-oxy)-3-phenyl-1H-indene-2-carboxylate ethyl ester
25) 6-(2-cyclohexylethoxy)-1-(trans-methylimino-N-oxy)-3-phenyl-1H-indene-2-carboxylate ethyl ester
26) 1-(trans-methylimino-N-oxy)-3-phenyl-6-(3-phenylprophenoxy)-1H-indene-2-carboxylate ethyl ester
27) 6-[2-(2-fluorophenyl)ethoxy]-1-(trans-methylimino-N-oxy)-3-phenyl-1H-indene-2-carboxylate ethyl ester
28) 6-[2-(3-fluorophenyl)ethoxy]-1-(trans-methylimino-N-oxy)-3-phenyl-1H-indene-2-carboxylate ethyl ester
29) 6-[2-(4-fluorophenyl)ethoxy]-1-(trans-methylimino-N-oxy)-3-phenyl-1H-indene-2-carboxylate ethyl ester
30) 1-(trans-methylimino-N-oxy)-3-phenyl-6-[2-(3-trifluoromethylphenyl)ethoxy]-1H-indene-2-carboxylate ethyl ester
31) 6-(4-methoxycarbonylbenzyloxy)-1-(trans-methylimino-N-oxy)-3-phenyl-1H-indene-2-carboxylate ethyl ester
32) 1-(trans-methylimino-N-oxy)-3-phenyl-6-(3-phenylpropoxy)-1H-indene-2-carboxylate ethyl amide
33) 1-(trans-methylimino-N-oxy)-6-(2-morpholine-4-ylethoxy)-3-phenyl-1H-indene-2-carboxylate ethyl ester
34) 6-[2-(cyclohexylmethylamino)ethoxy]-1-(trans-methylimino-N-oxy)-3-phenyl-1H-indene-2-carboxylate ethyl ester
35) 3-(2-fluorophenyl)-6-methoxy-1-(trans-methylimino-N-oxy)-1H-indene-2-carboxylate ethyl ester
36) 1-(trans-methylimino-N-oxy)-6-[2-(4-methylpiperazine-1-yl)ethoxy]-3-phenyl-1H-indene-2-carboxylate ethyl ester
37) (2,3-diphenyl indene-1-yl lidene)methylamine-N-oxide
38) 1-(trans-methylimino-N-oxy)-3-phenyl-6-(3-phenylpropoxy)-1H-indene-2-carboxylate isopropyl amide
39) 1-(trans-methylimino-N-oxy)-3-phenyl-6-(3-phenylpropoxy)-1H-indene-2-carboxylate cyclohexyl amide
40) [1-(trans-methylimino-N-oxy)-3-phenyl-6-(3-phenylpropoxy)-1H-indene-2-yl]morpholine-4-yl-methanone
41) 1-(trans-methylimino-N-oxy)-6-(2-morpholine-4-ylethoxy)-3-phenyl-1H-indene-2-carboxylate cyclohexyl amide
42) 1-(trans-methylimino-N-oxy)-3-phenyl-5-(3-phenylpropoxy)-1H-indene-2-carboxylate ethyl ester
43) 1-(trans-methylimino-N-oxy)-6-phenethyloxymethyl-3-phenyl-1H-indene-2-carboxylate ethyl ester
44) (6-methoxy-3-phenylindene-1-yllidene)methylamine-N-oxide 45) 1-(cis-methylimino-N-oxy)-6-(2-morpholine-4-ylethoxy)-3-phenyl-1H-indene-2-carboxylate ethyl ester
46) 6-(2-bromoethoxy)-1-(trans-methylimino-N-oxy)-3-phenyl-1H-indene-2-carboxylate ethyl ester
47) 1-(trans-methylimino-N-oxy)-6-(2-morpholine-4-ylethoxy)-3-phenyl-1H-indene-2-carboxylate tert-buthyl ester
48) 1-(trans-methylimino-N-oxy)-5,6-methylenedioxy-1-oxo-3-phenyl-1H-indene-2-carboxylate ethyl ester
49) 4-[2-isopropylcarbamoyl-3-(trans-methylimino-N-oxy)-1-phenyl-3H-indene-5-yl-oxylmethyl]benzoate methyl ester
50) 1-(trans-methylimino-N-oxy)-6-(2-morpholine-4-ylethoxy)-3-phenyl-1H-indene-2-carboxylate isopropyl amide
51) 1-(trans-methylimino-N-oxy)-6-(2-morpholine-4-ylethoxy)-3-phenyl-1H-indene-2-carboxylate cyclopropyl amide
52) 3-(3-fluorophenyl)-1-(trans-methylimino-N-oxy)-6-(2-morpholine-4-ylethoxy)-1H-indene-2-carboxylate isopropyl amide
53) (6-methoxy-1-(trans-methylimino-N-oxy)-3-phenyl-1H-indene-2-yl)acetate ethyl ester
54) (6-methoxy-1-(cis-methylimino-N-oxy)-3-phenyl-1H-indene-2-yl)acetate ethyl ester
55) 5-[2-(5-ethylpyridine-2-yl)ethoxy]-1-(trans-methylimino-N-oxy)-3-phenyl-1H-indene-2-carboxylate isopropyl amide
56) 1-(trans-methylimino-N-oxy)-6-(3-phenylpropoxy)-3-p-tolyl-1H-indene-2-carboxylate ethyl ester
57) 1-(trans-methylimino-N-oxy)-6-(3-phenylpropoxy)-3-thiophene-2-yl-1H-indene-2-carboxylate ethyl ester
58) 3-(4-chlorophenyl)-1-(trans-methylimino-N-oxy)-6-(3-phenylpropoxy)-1H-indene-2-carboxylate ethyl ester
59) 3-(5-chlorothiophene-2-yl)-1-(trans-methylimino-N-oxy)-6-(3-phenyl propoxy)-1H-indene-2-carboxylate ethyl ester
60) 1-(trans-methylimino-N-oxy)-6-(3-phenylpropoxy)-3-m-tolyl-1H-indene-2-carboxylate ethyl ester
61) 1-(trans-methylimino-N-oxy)-3-(4-phenoxyphenyl)-6-(3-phenylpropoxy)-1H-indene-2-carboxylate ethyl ester
62) 3-benzo-[1,3]-dioxol-5-yl-1-(trans-methylimino-N-oxy)-6-(3-phenyl propoxy)-1H-indene-2-carboxylate ethyl ester
63) methyl-[6-(3-phenylpropoxy)-3-pyridine-2-yl-indene-1-yllindene]-amine-N-oxide
64) 3-furan-2-yl-1-(trans-methylimino-N-oxy)-6-(3-phenylpropoxy)-1H-indene-2-carboxylate ethyl ester
65) 3-ethyl-1-(trans-methylimino-N-oxy)-6-(3-phenylpropoxy)-1H-indene-2-carboxylate ethyl ester
66) 3-methyl-1-(trans-methylimino-N-oxy)-6-(3-phenylpropoxy)-1H-indene-2-carboxylate ethyl ester
67) 1-(trans-methylimino-N-oxy)-6-(3-phenylpropoxy)-3-thiophene-3-yl-1H-indene-2-carboxylate ethyl ester
68) 3-cyclopropyl-1-(trans-methylimino-N-oxy)-6-(3-phenylpropoxy)-1H-indene-2-carboxylate ethyl ester
69) 1-(trans-methylimino-N-oxy)-6-(2-morpholine-4-ylethoxy)-3-thiophene-3-yl-1H-indene-2-carboxylate ethyl ester
70) 3-benzo-[b]-thiophene-3-yl-1-(trans-methylimino-N-oxy)-6-(3-phenyl propoxy)-1H-indene-2-carboxylate ethyl ester
71) 3-(1H-imidazole-4-yl)-1-(trans-methylimino-N-oxy)-6-(3-phenylpropoxy)-1H-indene-2-carboxylate ethyl ester
72) 3-(1-ethylpropyl)-1-(trans-methylimino-N-oxy)-6-(3-phenylpropoxy)-1H-indene-2-carboxylate ethyl ester
73) 1-(trans-methylimino-N-oxy)-3-phenyl-6-(3-phenylpropoxy)-1H-indene-2-carboxylate amide
74) 6-(4-benzylmorpholine-2-ylmethoxy)-1-(trans-methylimino-N-oxy)-3-phenyl-1H-indene-2-carboxylate isopropyl amide
75) 1-(trans-methylimino-N-oxy)-3-phenyl-6-(3-phenylpropoxy)-1H-indene-2-carbonitrile
76) 1-(trans-methylimino-N-oxy)-5,6-methylenedioxy-1-oxo-3-phenyl-1H-phenyl-2-carboxylate isopropyl amide
77) 1-(trans-methylimino-N-oxy)-6-morpholine-4-ylmethyl-3-phenyl-1H-indene-2-carboxylate ethyl ester
78) 1-(trans-methylimino-N-oxy)-3-phenyl-6-(2-pyridine-2-ylethoxy)-1H-indene-2-carboxylate ethyl ester
79) 6-[2-(5-ethylpyridine-2-yl)ethoxy]-1-(trans-methylimino-N-oxy)-3-phenyl-1H-indene-2-carboxylate ethyl ester
80) 1-(trans-methylimino-N-oxy)-3-phenyl-6-(2-pyridine-2-ylethoxy)-1H-indene-2-carboxylate isopropyl amide
81) 6-[2-(5-ethylpyridine-2-yl)ethoxy]-1-(trans-methylimino-N-oxy)-3-phenyl-1H-indene-2-carboxylate isopropyl amide
82) methyl-[6-(2-morpholine-4-ylethoxy)-3-phenylindene-1-yllidene]amine-N-oxide
83) 5,6-bis-methanesulfonyloxy-1-(trans-methylimino-N-oxy)-3-phenyl-1H-indene-2-carboxylate ethyl ester
84) 1-(trans-methylimino-N-oxy)-6-(2-morpholine-4-ylethoxy)-3-phenyl-1H-indene-2-carboxylate isobutyl ester
85) 1-(trans-methylimino-N-oxy)-6-(2-morpholine-4-ylethoxy)-3-phenyl-1H-indene-2-carboxylate methyl ester
86) 1-(cis-methylimino-N-oxy)-6-(2-morpholine-4-ylethoxy)-3-phenyl-1H-indene-2-carboxylate methyl ester
87) 1-(trans-methylimino-N-oxy)-6-(2-morpholine-4-ylethoxy)-3-phenyl-1H-indene-2-carboxylate propyl ester
88) 3-(4-fluorophenyl)-1-(trans-methylimino-N-oxy)-6-(2-morpholine-4-ylethoxy)-1H-indene-2-carboxylate ethyl ester
89) 1-(trans-methylimino-N-oxy)-3-phenyl-6-(pyridine-2-ylmethoxy)-1H-indene-2-carboxylate ethyl ester
90) 1-(trans-methylimino-N-oxy)-3-phenyl-6-(pyridine-2-yloxy)-1H-indene-2-carboxylate ethyl ester
91) 6-(3-methoxybenzyloxy)-1-(trans-methylimino-N-oxy)-3-phenyl-1H-indene-2-carboxylate ethyl ester
92) 1-(trans-methylimino-N-oxy)-6-(2-morpholine-4-ylethoxy)-3-thiophene-3-yl-1H-indene-2-carboxylate isopropyl amide
93) 3-(1-ethylpropyl)-1-(trans-methylimino-N-oxy)-6-(2-morpholine-4-yl ethoxy)-1H-indene-2-carboxylate ethyl ester
94) 3-benzo-[b]-thiophene-3-yl-1-(trans-methylimino-N-oxy)-6-(2-morpholine-4-ylethoxy)-1H-indene-2-carboxylate isopropyl amide
95) 3-(4-fluorophenyl)-1-(trans-methylimino-N-oxy)-6-(2-morpholine-4-ylethoxy)-1H-indene-2-carboxylate isopropyl amide 96) 3-(1-ethylpropyl)-1-(trans-methylimino-N-oxy)-6-(2-morpholine-4-ylethoxy)-1H-indene-2-carboxylate isopropyl amide
97) 1-(trans-methylimino-N-oxy)-6-(2-morpholine-4-ylethoxy)-3-(2,4,6-trimethyl phenyl)-1H-indene-2-carboxylate ethyl ester
98) 3-(2,6-dimethylphenyl)-1-(trans-methylimino-N-oxy)-6-(2-morpholine-4-ylethoxy)-1H-indene-2-carboxylate ethyl ester
99) 1-(trans-methylimino-N-oxy)-3-phenyl-5-(2-pyridine-2-ylethoxy)-1H-indene-2-carboxylate isopropyl amide
100) 1-(trans-methylimino-N-oxy)-5-(2-morpholine-4-ylethoxy)-3-phenyl-1H-indene-2-carboxylate isopropyl amide
101) 1-(cis-methylimino-N-oxy)-6-(2-morpholine-4-ylethoxy)-3-phenyl-1H-indene-2-carboxylate isopropyl ester
102) 3-(3-fluorophenyl)-1-(trans-methylimino-N-oxy)-6-(2-pyridine-2-ylethoxy)-1H-indene-2-carboxylate isopropyl amide
103) 6-[2-(5-ethylpyridine-2-yl)ethoxy]-3-(3-fluorophenyl)-1-(trans-methylimino-N-oxy)-1H-indene-2-carboxylate isopropyl amide
104) 3-(4-cyanophenyl)-6-(2-morpholine-4-ylethoxy)-1-(trans-methylimino-N-oxy)-1H-indene-2-carboxylate ethyl ester, and
105) 1-(trans-methylimino-N-oxy)-3-phenyl-6-(2-pyridine-2-ylethoxy)-1H-indene-2-carboxylate isopropyl ester.

5. A process for preparing the compound of formula (I) which comprises the step of subjecting an indenone compound of formula (II) to a condensation reaction with $R_1NHOH$ to obtain a compound of formula (I); or comprises the steps of subjecting an indenone compound of formula (II) to a condensation reaction with $NH_2OH$ to obtain a compound of formula (III), and conducting a reaction of the compound of formula (III) with $R_1X$ to obtain a compound of formula (I):

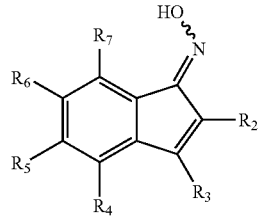
(I)

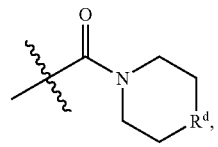
(II)

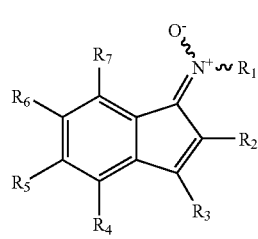
(III)

wherein,
X is halogen;
$R_1$ is $C_{1-6}$ alkyl, $C_{1-6}$ alkenyl, or $C_{3-6}$ cycloalkyl, each of which is unsubstituted or substituted with one or more phenyl groups;
$R_2$ is H, CN, $CO_2R^a$, $CH_2CO_2R^a$, $CONR^bR^c$,

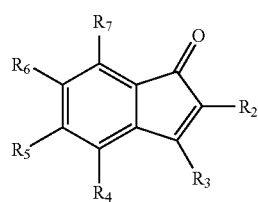

or phenyl;
$R_3$ is $C_{1-6}$ alkyl, $C_{3-6}$ cycloalkyl, naphthyl, phenyl,

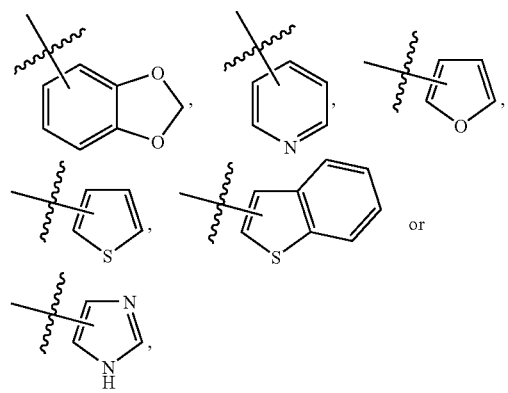

phenyl and

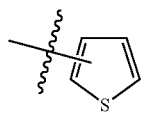

being each unsubstituted or substituted with one or more substituents selected from the group consisting of halogen, CN, $NH_2$, $NO_2$, $OR^a$, phenyloxy, $C_{1-6}$ alkyl, and $C_{3-6}$ cycloalkyl; and
$R_4$, $R_5$, $R_6$, and $R_7$ are each independently H, OH, $OSO_2CH_3$, $O(CH_2)_mR^e$, $CH_2R^f$, $OCOCH_2OR^g$, $OCH_2CH_2OR^g$, $OCH_2CH=CHR^g$, $R_5$ and $R_6$ together form $OCH_2O$;
in which $R^a$ is H, $C_{1-6}$ alkyl, or $C_{3-6}$ cycloalkyl, $C_{1-6}$ alkyl and $C_{3-6}$ cycloalkyl being each unsubstituted or substituted with one or more halogens;

$R^b$ and $R^c$ are each independently H, $C_{1-6}$ alkyl, or $C_{3-6}$ cycloalkyl;

$R^d$ is O, S, or $NR^a$;

$R^e$ is H, halogen, $C_{3-6}$ cycloalkyl, naphthyl,

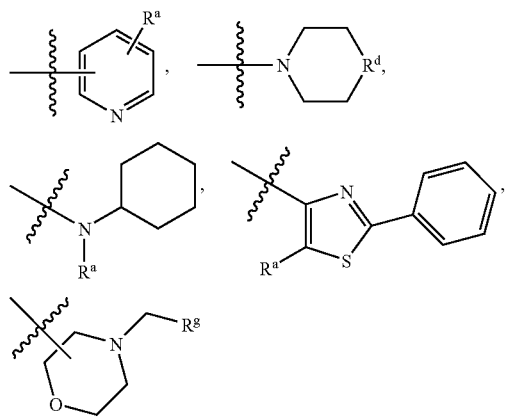

or phenyl, phenyl being unsubstituted or substituted with one or more substituents selected from the group consisting of halogen, CN, $NH_2$, $NO_2$, $OR^a$, $CF_3$, and $COOR^a$;

$R^f$ is $OCH_2CH_2R^g$ or

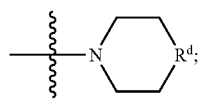

$R^g$ is phenyl, which is unsubstituted or substituted with one or more substituents selected from the group consisting of halogen, CN, $NH_2$, $NO_2$, and $OR^a$; and m is an integer in the range of 1 to 5.

6. The process of claim 5, wherein the indenone compound of formula (II) is prepared by a process comprising the steps of:

1) reacting compounds of formula (V) and (VI) to obtain a compound of formula (VII);
2) subjecting the compound of formula (VII) to cyclization to obtain a compound of formula (VIII); and
3) subjecting the compound of formula (VIII) to oxidation, (V)

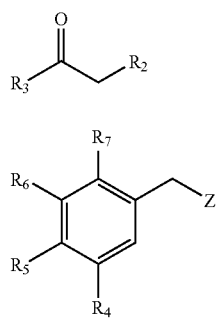

(VI)

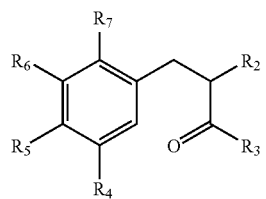

(VII)

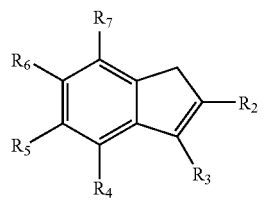

(VIII)

-continued wherein, $R_2$ to $R_7$ have the same meanings as defined in claim 5, and Z is halogen or activated leaving group.

7. The process of claim 5, wherein the indenone compound of formula (II) is prepared by a process comprising the steps of:

1) reacting compounds of formula (IX) and (X) to obtain a compound of formula (XI);
2) subjecting the compound of formula (XI) to cyclization to obtain a compound of formula (XII); and
3) subjecting the compound of formula (XII) to oxidation, (IX)

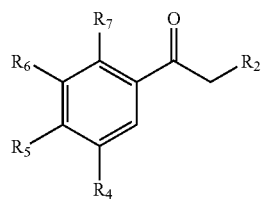

(X)

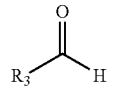

(XI)

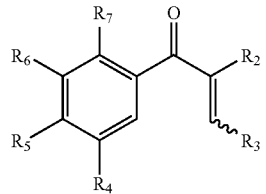

(XII)

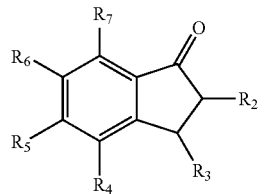

wherein,

R₂ to R₇ have the same meanings as defined in claim 5.

8. The process of claim 5, wherein the indenone compound of formula (II) is prepared by a process comprising the steps of:
1) reacting compounds of formula (IX) and (XIII) to obtain a compound of formula (XIV); and
2) subjecting the compound of formula (XIV) to cyclization,

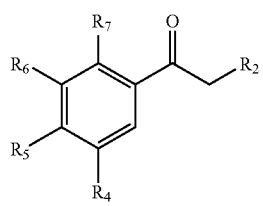

(IX)

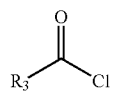

(XIII)

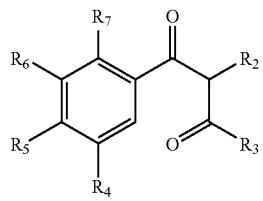

(XIV)

wherein,

R₂ to R₇ have the same meanings as defined in claim 5.

9. The process of claim 5, wherein the indenone compound of formula (II) is prepared by a process comprising the steps of:
1) subjecting a compound of formula (XV) to bromination obtain a compound of formula (XVI); and
2) subjecting the compound of formula (XVI) to a carbon-carbon coupling reaction in the presence of a metal catalyst, or to a substitution reaction using a nucleophile,

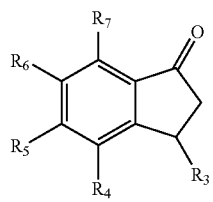

(XV)

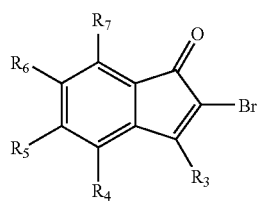

(XVI)

wherein,

R₃ to R₇ have the same meanings as defined in claim 5.

10. The process of claim 5, wherein the indenone compound of formula (II) is prepared by a process comprising the steps of:
1) subjecting a compound of formula (XVII) to bromination to obtain a compound of formula (XVIII); and
2) subjecting the compound of formula (XVIII) to a carbon-carbon coupling reaction in the presence of a metal catalyst, or to a substitution reaction using a nucleophile,

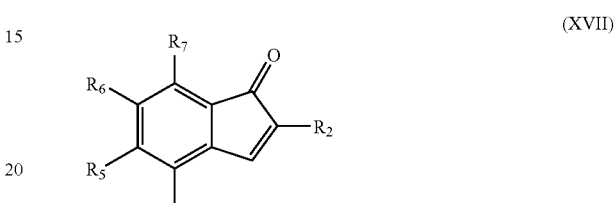

(XVII)

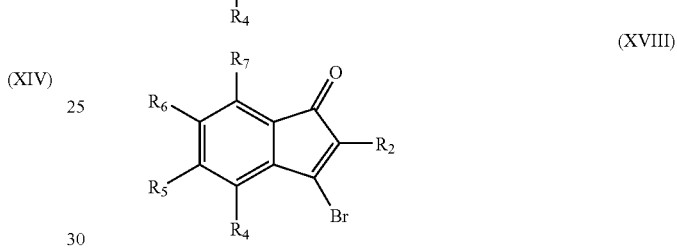

(XVIII)

wherein,

R₂ and R₄ to R₇ have the same meanings defined in claim 5.

11. The process of claim 5, wherein the indenone compound of formula (II) is prepared by subjecting a compound of formula (XIX) to an acylation reaction, a halogenation reaction followed by a substitution reaction by a nucleophile, or a carbon-carbon coupling reaction in the presence of a metal catalyst,

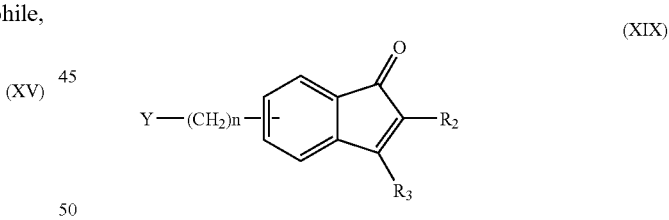

(XIX)

wherein,

R₂ and R₃ have the same meanings defined in claim 5, Y is hydroxy, thiol, amino C₁₋₆ alkyl or halogen, and n is an integer in the range of 0 to 5.

12. A pharmaceutical composition for activating the activities of peroxisome proliferator activated receptor gamma sub type comprising the compound or salt defined in claim 1 as an active ingredient together with a pharmaceutically acceptable carrier.

* * * * *